(12) United States Patent
Baron et al.

(10) Patent No.: US 8,389,472 B2
(45) Date of Patent: Mar. 5, 2013

(54) EXENDIN-4 TO TREAT NONALCOHOLIC STEATOHEPATITIS AND NONALCOHOLIC FATTY LIVER DISEASE

(75) Inventors: Alain D. Baron, San Diego, CA (US); Dennis Kim, San Diego, CA (US); David G. Maggs, San Diego, CA (US); Matthew Wintle, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 943 days.

(21) Appl. No.: 12/063,712

(22) PCT Filed: Aug. 21, 2006

(86) PCT No.: PCT/US2006/032661
§ 371 (c)(1),
(2), (4) Date: Mar. 16, 2009

(87) PCT Pub. No.: WO2007/022518
PCT Pub. Date: Feb. 22, 2007

(65) Prior Publication Data
US 2009/0312246 A1     Dec. 17, 2009

Related U.S. Application Data

(60) Provisional application No. 60/709,647, filed on Aug. 19, 2005, provisional application No. 60/709,604, filed on Aug. 19, 2005, provisional application No. 60/779,216, filed on Mar. 3, 2006.

(51) Int. Cl.
*A61K 38/26* (2006.01)
*A61K 38/00* (2006.01)
*A61K 38/16* (2006.01)
*A61K 39/00* (2006.01)

(52) U.S. Cl. ...... 514/7.2; 514/7.4; 514/21.3; 424/185.1; 424/198.1; 530/300; 530/324

(58) Field of Classification Search ........................ None
See application file for complete search history.

(56) References Cited

U.S. PATENT DOCUMENTS 5,424,286 A    6/1995   Eng
7,138,375 B2 *   11/2006   Beeley et al. .................. 514/5.8

FOREIGN PATENT DOCUMENTS

WO      WO98/30231     7/1998

OTHER PUBLICATIONS

Nielsen (2005) Drug Discovery Today, vol. 10, No. 10, 703-710.*
Buse et al. (2004), Diabetes Care 27: 2628-2635.*
George et al. Frontmatter, in Fatty Liver Disease: NASH and Related Disorders (2004), Chapter 15, 181-193.*
Xiaokun, Ding; "Glucagon-like Protein-1 (GLP-1_Receptor Agonist, Reduces Hepatic Steatosis and Lipid Peroxidation in OB/OB Mice", Database Biosis [Online]; Biosciences Information Service, PA, US; Apr. 2004.
Lavine, Joel E., et al., "Effect of Vitamin E orMetformin for Treatment of Nonalcoholic Fatty Liver Disease in Children and Adolescents, The TONIC Randomized Controlled Trial", JAMA, Apr. 27, 2011, vol. 305, No. 16, pp. 1659-1668.
Marchesini, Giulio, et al., "Association of Nonalcoholic Fatty Liver Disease with Insulin Resistance", The American Journal of Medicine, Nov. 1999, vol. 107, pp. 450-455.
Marchesini, Giulio, et al., "Nonalcoholic Fatty Liver, Steatohepatitis, and the Metabolic Syndrome", Hepatology, vol. 37, No. 4, 2003, pp. 917-923.
Sanyal, Arun J., "AGA Technical Review on Nonalcoholic Fatty Liver Disease", Gastroenterology, 2002, vol. 123, pp. 1705-1725.
Sanyal, Arun J., "Pioglitazone, Vitamin E, or Placebo for Nonalcholic Steatohepatitis", New England Journal of Medicine, vol. 362;18, May 6, 2010, pp. 1675-1685.

* cited by examiner

*Primary Examiner* — Christine J Saoud
*Assistant Examiner* — Jegatheesan Seharaseyon
(74) *Attorney, Agent, or Firm* — Womble Carlyle Sandridge & Rice LLP

(57) ABSTRACT

The present invention relates generally to the novel use of incretin compounds (ICs) and amylinomimetic compounds to treat, prevent, or ameliorate a variety of metabolic conditions or diseases.

16 Claims, 8 Drawing Sheets

Figure 5

A
Weight Change by 2-Year Weight Change Quartiles
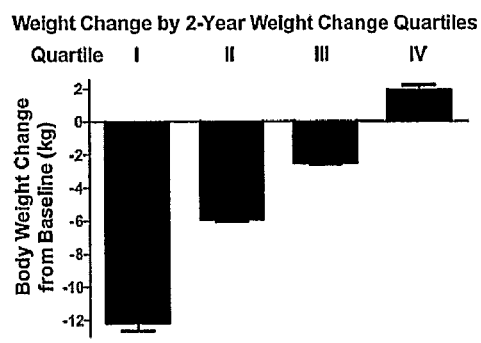

B
ALT Change by 2-Year Weight Change Quartiles
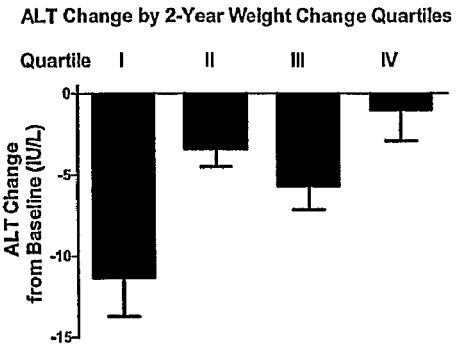

C
AST Change by 2-Year Weight Change Quartiles
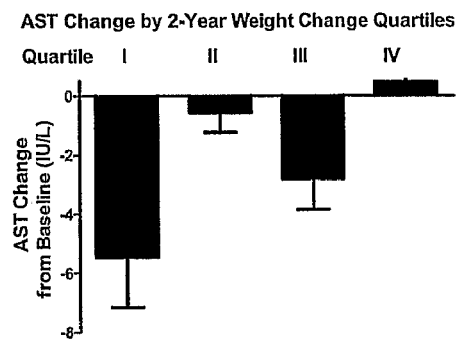

D
$HbA_{1c}$ Change by 2-Year Weight Change Quartiles
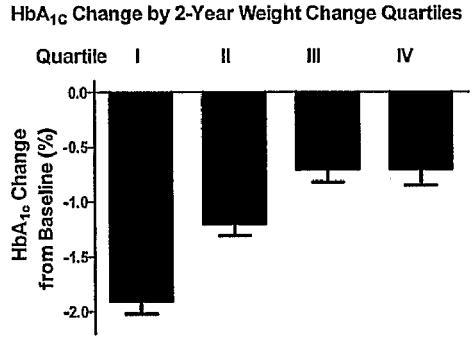

E
Weight Change by 2-Year $HbA_{1c}$ Change Quartiles
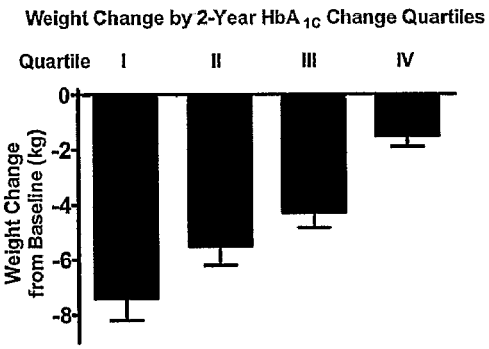

F
ALT Change by 2-Year $HbA_{1c}$ Change Quartiles
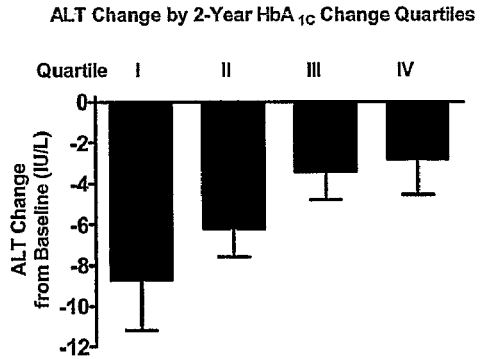

G
AST Change by 2-Year $HbA_{1c}$ Change Quartiles
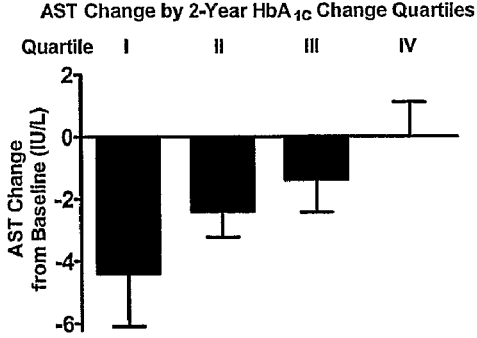

H
$HbA_{1c}$ Change by 2-Year $HbA_{1c}$ Change Quartiles
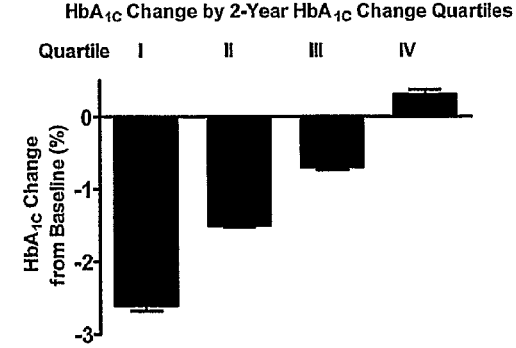

Figure 7
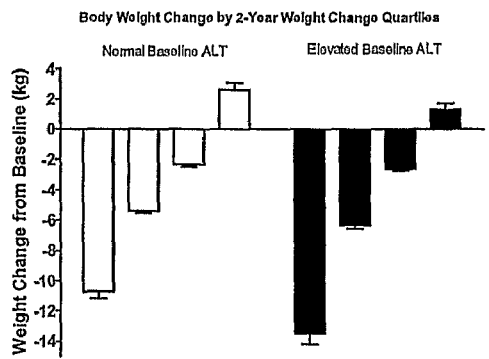
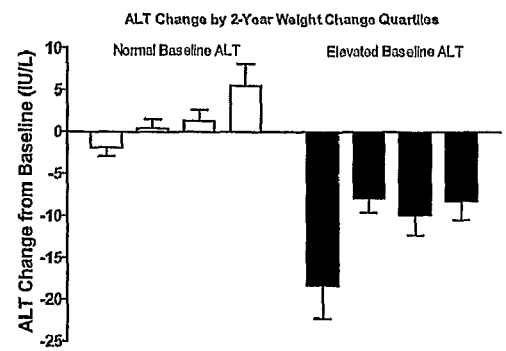
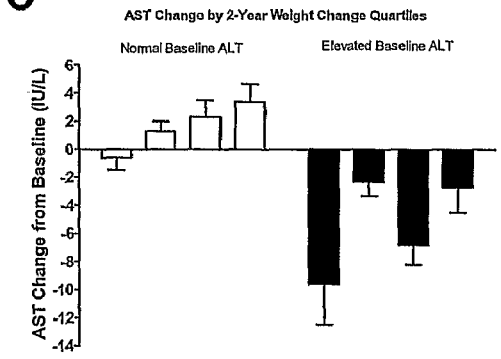
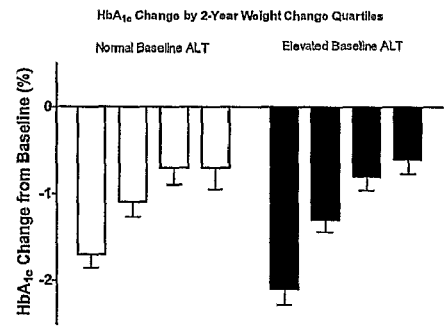
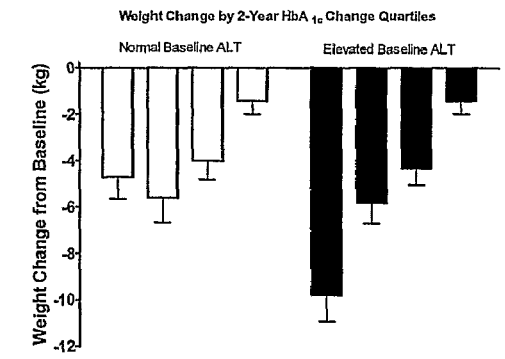
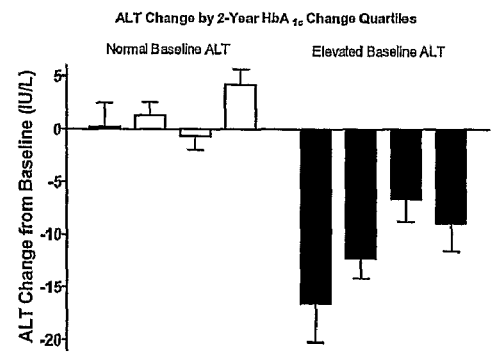
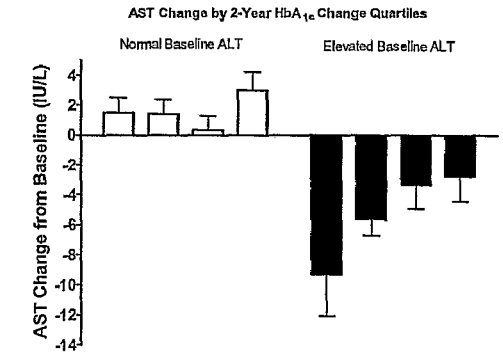
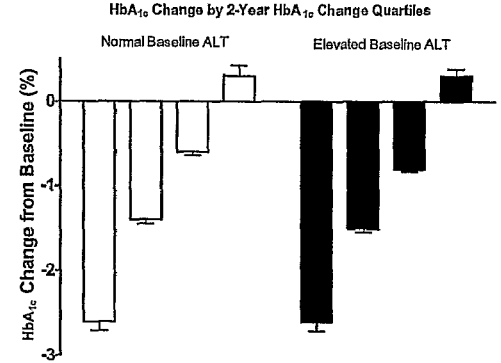

```
                        SEQUENCE LISTING

<160> NUMBER OF SEQ ID NOS: 48

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)
<223> OTHER INFORMATION: Lys, Ala, Ser, or absent
<220> FEATURE:
<221> NAME/KEY: MOD_RES
<222> LOCATION: (2)
<223> OTHER INFORMATION: amino acid with side chain bonded to side chain
      of amino acid at position (7) to form intramolecular linkage or
      amino acid may be Ala, Ser, Cys, Val, Leu or Ile or
      alkyl, aryl, or aralkyl esters and ethers of Ser or Cys
<220> FEATURE:
<221> NAME/KEY: MOD_RES
<222> LOCATION: (7)
<223> OTHER INFORMATION: amino acid with side chain bonded to side chain
      of amino acid at position (2) to form intramolecular linkage or
      amino acid may be Ala, Ser, Cys, Val, Leu or Ile or
      alkyl, aryl, or aralkyl esters and ethers of Ser or Cys
<220> FEATURE:
<221> NAME/KEY: VARIANT
<222> LOCATION: (13)
<223> OTHER INFORMATION: Ala, Ser or Thr
<220> FEATURE:
<221> NAME/KEY: VARIANT
<222> LOCATION: (17)
<223> OTHER INFORMATION: Val, Leu or Ile
<220> FEATURE:
<221> NAME/KEY: VARIANT
<222> LOCATION: (18)
<223> OTHER INFORMATION: His or Arg
<220> FEATURE:
<221> NAME/KEY: VARIANT
<222> LOCATION: (19)
<223> OTHER INFORMATION: Ser or Thr
<220> FEATURE:
<221> NAME/KEY: VARIANT
<222> LOCATION: (20)
<223> OTHER INFORMATION: Ser, Thr, Gln or Asn
<220> FEATURE:
<221> NAME/KEY: VARIANT
<222> LOCATION: (21)
<223> OTHER INFORMATION: Asn, Gln or His
```

```
<220> FEATURE:
<221> NAME/KEY: VARIANT
<222> LOCATION: (23)
<223> OTHER INFORMATION: Phe, Leu or Tyr
<220> FEATURE:
<221> NAME/KEY: VARIANT
<222> LOCATION: (25)
<223> OTHER INFORMATION: Ala or Pro
<220> FEATURE:
<221> NAME/KEY: VARIANT
<222> LOCATION: (26)
<223> OTHER INFORMATION: Ile, Val, Ala or Leu
<220> FEATURE:
<221> NAME/KEY: VARIANT
<222> LOCATION: (28)
<223> OTHER INFORMATION: Ser, Pro, Leu, Ile or Thr
<220> FEATURE:
<221> NAME/KEY: VARIANT
<222> LOCATION: (29)
<223> OTHER INFORMATION: Ser, Pro or Thr
<220> FEATURE:
<221> NAME/KEY: VARIANT
<222> LOCATION: (31)
<223> OTHER INFORMATION: Asn, Asp or Gln

<400> SEQUENCE: 2

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)
<223> OTHER INFORMATION: Lys, Arg or absent
<220> FEATURE:
<221> NAME/KEY: VARIANT
<222> LOCATION: (2)
<223> OTHER INFORMATION: Cys or absent
<220> FEATURE:
<221> NAME/KEY: VARIANT
<222> LOCATION: (3)
<223> OTHER INFORMATION: Asn, Gln or Asp
<220> FEATURE:
<221> NAME/KEY: VARIANT
<222> LOCATION: (4)
<223> OTHER INFORMATION: Thr, Ser, Met, Val, Leu or Ile
<220> FEATURE:
<221> NAME/KEY: VARIANT
<222> LOCATION: (5)
<223> OTHER INFORMATION: Ala or Val
<220> FEATURE:
<221> NAME/KEY: VARIANT
<222> LOCATION: (6)
<223> OTHER INFORMATION: Thr or Ser
<220> FEATURE:
<221> NAME/KEY: VARIANT
<222> LOCATION: (7)
<223> OTHER INFORMATION: Cys or Ala
<220> FEATURE:
<221> NAME/KEY: VARIANT
<222> LOCATION: (8)...(9)
<223> OTHER INFORMATION: Ala-Thr, Ala-Ser, Ser-Met, Glu-Thr or Val-Thr
<220> FEATURE:
<221> NAME/KEY: VARIANT
<222> LOCATION: (10)
<223> OTHER INFORMATION: Gln, Ala or Asn
```

```
<220> FEATURE:
<221> NAME/KEY: VARIANT
<222> LOCATION: (11)..(13)
<223> OTHER INFORMATION: Arg-Leu-Ala, His-Leu-Ala, Arg-Ile-Ala,
      Lys-Ile-Ala, Arg-Met-Ala, His-Met-Ala,
      Lys-Met-Ala or Arg-Leu-Thr
<220> FEATURE:
<221> NAME/KEY: VARIANT
<222> LOCATION: (14)
<223> OTHER INFORMATION: Asn, Ala or Gln
<220> FEATURE:
<221> NAME/KEY: VARIANT
<222> LOCATION: (15)..(16)
<223> OTHER INFORMATION: Phe-Leu, Phe-Ile, Phe-Met, Tyr-Leu,
      Tyr-Ile, Tyr-Met, Trp-Met or Tr-pIle
<220> FEATURE:
<221> NAME/KEY: VARIANT
<222> LOCATION: (17)
<223> OTHER INFORMATION: Val, Ala, Ile, Met, Leu, Pentyl Gly or t-butyl
      Gly
<220> FEATURE:
<221> NAME/KEY: VARIANT
<222> LOCATION: (18)..(22)
<223> OTHER INFORMATION: any one of SEQ ID NOS 5-15, Arg-Ser,
      Lys-Ser, His-Ser, Arg-Thr, Pro-Ser or
      Arg

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)
<223> OTHER INFORMATION: Asn, Gln or Asp
<220> FEATURE:
<221> NAME/KEY: VARIANT
<222> LOCATION: (2)
<223> OTHER INFORMATION: Thr, Ser, Met, Val, Leu or Ile
<220> FEATURE:
<221> NAME/KEY: VARIANT
<222> LOCATION: (3)
<223> OTHER INFORMATION: Ala or Val
<220> FEATURE:
<221> NAME/KEY: VARIANT
<222> LOCATION: (4)
<223> OTHER INFORMATION: Thr or Ser

<400> SEQUENCE: 4

Xaa Xaa Xaa Xaa
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Ser Gly Tyr
1               5
```

```
<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ser Ser Gly Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ser Ser Gly Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Ser Ser Gly Tyr
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Arg Gly Tyr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Thr Ser Gly Tyr
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Arg Ala Ser Gly Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ser Ser Gly Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Ala Gly Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Ser Ala Gly Tyr
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Gly Tyr
1

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)
<223> OTHER INFORMATION: Ala, Cys, homoCys, Asp, Glu, Phe, Ile, Leu,
      Lys, homoLys, Arg, homoArg, Ser, Hse, Thr, Gly, Gln, Asn,
      Met, Tyr, Trp, Phe, Hyp, His, Val or absent
```

```
<220> FEATURE:
<221> NAME/KEY: VARIANT
<222> LOCATION: (2)
<223> OTHER INFORMATION: amino acid with side chain bonded to side chain
      of amino acid at position (7) to form intramolecular;
      linkage; or the amino acid is Ser, Asp, Glu, Lys,
      Orn, or Cys
<220> FEATURE:
<221> NAME/KEY: VARIANT
<222> LOCATION: (3)
<223> OTHER INFORMATION: Ala, Asp, Glu, Asn, Gln, Gly, Val, Arg, Lys,
      HomoLys, HomoArg, His, Ile, Leu, Met or absent
<220> FEATURE:
<221> NAME/KEY: VARIANT
<222> LOCATION: (4)
<223> OTHER INFORMATION: Ala, Ile, Leu, Ser, Hse, Thr, Val, Met or
      absent
<220> FEATURE:
<221> NAME/KEY: VARIANT
<222> LOCATION: (5)
<223> OTHER INFORMATION: Ala, Ser, Thr, Hse, Tyr, Val, Ile, Leu or Met
<220> FEATURE:
<221> NAME/KEY: VARIANT
<222> LOCATION: (6)
<223> OTHER INFORMATION: Thr, Ala, Ser, Hse, Tyr, Val, Ile, Leu or Met
<220> FEATURE:
<221> NAME/KEY: VARIANT
<222> LOCATION: (7)
<223> OTHER INFORMATION: amino acid with side chain bonded to side chain
      of amino acid at position (2) to form intramolecular;
      linkage; or the amino acid is Ser, Asp, Glu, Lys,
      Orn, or Cys
<220> FEATURE:
<221> NAME/KEY: VARIANT
<222> LOCATION: (8)
<223> OTHER INFORMATION: Ala, Val, Ile, Leu, Phe or Met
<220> FEATURE:
<221> NAME/KEY: VARIANT
<222> LOCATION: (9)
<223> OTHER INFORMATION: Leu, Thr, Ser, Hse, Val, Ile or Met
<220> FEATURE:
<221> NAME/KEY: VARIANT
<222> LOCATION: (10)
<223> OTHER INFORMATION: Gly, His, Gln, Lys, Arg, Asn, homoLys or
      homoArg
<220> FEATURE:
<221> NAME/KEY: VARIANT
<222> LOCATION: (11)
<223> OTHER INFORMATION: Lys, Arg, Gln, Asn, homoLys, homoArg or His
<220> FEATURE:
<221> NAME/KEY: VARIANT
<222> LOCATION: (12)
<223> OTHER INFORMATION: Leu, Ile, Val, Phe, Met, Trp or Tyr
<220> FEATURE:
<221> NAME/KEY: VARIANT
<222> LOCATION: (13)
<223> OTHER INFORMATION: Ala, Phe, Tyr, Asn, Gln, Ser, Hse or Thr
<220> FEATURE:
<221> NAME/KEY: VARIANT
<222> LOCATION: (14)
<223> OTHER INFORMATION: Ala, Asp, Glu, Gly, Asn, Lys, Gln, Arg, His,
      homoArg or homoLys
<220> FEATURE:
<221> NAME/KEY: VARIANT
<222> LOCATION: (15)
<223> OTHER INFORMATION: Ala, Asp, Glu, Phe, Leu, Ser, Tyr, Ile, Val or
      Met
<220> FEATURE:
<221> NAME/KEY: VARIANT
<222> LOCATION: (16)
<223> OTHER INFORMATION: Leu, Phe, Met, Val, Tyr or Ile
<220> FEATURE:
<221> NAME/KEY: VARIANT
<222> LOCATION: (17)
<223> OTHER INFORMATION: His, Gln, Asn, Ser, Hse, Thr or Val
<220> FEATURE:
<221> NAME/KEY: VARIANT
<222> LOCATION: (18)
<223> OTHER INFORMATION: Lys, homoLys, Arg, homoArg, His, Cit or Orn
```

```
<220> FEATURE:
<221> NAME/KEY: VARIANT
<222> LOCATION: (19)
<223> OTHER INFORMATION: Phe, Leu, Ser, Hse, Val, Ile, Thr or absent
<220> FEATURE:
<221> NAME/KEY: VARIANT
<222> LOCATION: (20)
<223> OTHER INFORMATION: His, Arg, Lys, homoArg, homoLys, Asn, Gln or
      absent
<220> FEATURE:
<221> NAME/KEY: VARIANT
<222> LOCATION: (21)
<223> OTHER INFORMATION: Thr, Ser, Hse, Val, Ile, Leu, Gln, Asn or
      absent
<220> FEATURE:
<221> NAME/KEY: VARIANT
<222> LOCATION: (22)
<223> OTHER INFORMATION: Phe, Leu, Met, Val, Tyr or Ile
<220> FEATURE:
<221> NAME/KEY: VARIANT
<222> LOCATION: (23)
<223> OTHER INFORMATION: Pro or Hyp
<220> FEATURE:
<221> NAME/KEY: VARIANT
<222> LOCATION: (24)
<223> OTHER INFORMATION: Pro, Hyp, Arg, Lys, homoArg, homoLys or His
<220> FEATURE:
<221> NAME/KEY: MOD_RES
<222> LOCATION: (25)
<223> OTHER INFORMATION: Thr, Ser, Hse, Val, Ile, Leu, Phe or Tyr
<220> FEATURE:
<221> NAME/KEY: VARIANT
<222> LOCATION: (26)
<223> OTHER INFORMATION: Asn, Gln, Asp or Glu
<220> FEATURE:
<221> NAME/KEY: VARIANT
<222> LOCATION: (27)
<223> OTHER INFORMATION: Thr, Val, Ser, Phe, Ile or Leu
<220> FEATURE:
<221> NAME/KEY: VARIANT
<222> LOCATION: (28)
<223> OTHER INFORMATION: Gly or Ala
<220> FEATURE:
<221> NAME/KEY: VARIANT
<222> LOCATION: (29)
<223> OTHER INFORMATION: Ser, Hse, Thr, Val, Ile, Leu or Tyr
<220> FEATURE:
<221> NAME/KEY: VARIANT
<222> LOCATION: (30)
<223> OTHER INFORMATION: Glu, Gly, Lys, Asn, Asp, Arg, homoArg, HomoLys,
      His or Gln
<220> FEATURE:
<221> NAME/KEY: VARIANT
<222> LOCATION: (31)
<223> OTHER INFORMATION: Ala, Thr, Ser, Hse, Val, Ile, Leu, Phe or Tyr
<220> FEATURE:
<221> NAME/KEY: VARIANT
<222> LOCATION: (32)
<223> OTHER INFORMATION: Phe, Pro, Tyr, Hse, Ser, Thr or Hyp

<400> SEQUENCE: 16

Xaa Xaa Xaa Xaa Xaa Xaa Tyr Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 17
<211> LENGTH: 32
<212> TYPE: PRT
<213> ORGANISM: Salmo salar
```

```
<400> SEQUENCE: 17

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Ser Glu Gly Thr Phe Thr Ser Asp
1               5

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Leu Gln Gln Trp Gln Lys Leu Leu Gln Lys Leu Lys Gln
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Leu Gln Gln Leu Gln Lys Leu Leu Gln Lys Leu Lys Gln Tyr
1               5                   10                  15

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: VARIANT
<222> LOCATION: (1)..(2)
<223> OTHER INFORMATION: Leu-Leu, Val-Leu, Ile-Leu, Ala-Thr,
      tert-Leu-Leu, Nle-Leu, or an N-acylated derivative thereof; or SEQ
      ID NO 23
<220> FEATURE:
<221> NAME/KEY: VARIANT
<222> LOCATION: (3)
<223> OTHER INFORMATION: Gly, Glu, Asn, or Aib
<220> FEATURE:
<221> NAME/KEY: VARIANT
<222> LOCATION: (4)
<223> OTHER INFORMATION: Arg, Orn, Lys, or epsilon-amidated derivatives
      thereof
<220> FEATURE:
<221> NAME/KEY: VARIANT
<222> LOCATION: (5)..(6)
<223> OTHER INFORMATION: Ser-Gln, Thr-Gln, Ala-Asn, or Thr-Asn
<220> FEATURE:
<221> NAME/KEY: VARIANT
<222> LOCATION: (7)
<223> OTHER INFORMATION: His, Aib, Ile, Leu, or Val
<220> FEATURE:
<221> NAME/KEY: VARIANT
<222> LOCATION: (8)
<223> OTHER INFORMATION: Gly, Glu, Asn or Aib
<220> FEATURE:
<221> NAME/KEY: VARIANT
<222> LOCATION: (9)
<223> OTHER INFORMATION: Arg, Orn, Lys or epsilon-amidated derivatives
      thereof
<220> FEATURE:
<221> NAME/KEY: VARIANT
<222> LOCATION: (11)..(12)
<223> OTHER INFORMATION: Ser-Gln, Thr-Gln, Ala-Asn or Thr-Asn
<220> FEATURE:
<221> NAME/KEY: VARIANT
<222> LOCATION: (15)
<223> OTHER INFORMATION: His, Aib, Ile, Leu or Val
<220> FEATURE:
<221> NAME/KEY: VARIANT
<222> LOCATION: (16)
<223> OTHER INFORMATION: Arg, Orn, Lys or epsilon-amidated derivatives
      thereof
<220> FEATURE:
<221> NAME/KEY: VARIANT
<222> LOCATION: (25)..(30)
<223> OTHER INFORMATION: SEQ ID NO 24, 25, 26, or 27

<400> SEQUENCE: 22

Xaa Xaa Xaa Xaa Xaa Xaa Xaa Xaa Xaa Leu Xaa Xaa Glu Leu Xaa
1               5                   10                  15

Xaa Leu Gln Thr Tyr Pro Arg Thr Asn Xaa Xaa Xaa Xaa Xaa Xaa
            20                  25                  30

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Ala, Ser, Cys or Thr

<400> SEQUENCE: 23

Ser Thr Xaa Val Leu
1               5
```

```
<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Gly Ser Asn Thr Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Gly Ser Gly Thr Pro
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Gly Ser Asn Thr Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Gly Ser Gly Thr Pro
1               5

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 29
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)
<223> OTHER INFORMATION: His, Arg or Tyr
<220> FEATURE:
<221> NAME/KEY: VARIANT
<222> LOCATION: (2)
<223> OTHER INFORMATION: Ser, Gly, Ala or Thr
<220> FEATURE:
<221> NAME/KEY: VARIANT
<222> LOCATION: (3)
<223> OTHER INFORMATION: Asp or Glu
<220> FEATURE:
<221> NAME/KEY: VARIANT
<222> LOCATION: (6)
<223> OTHER INFORMATION: Phe, Tyr or naphthylalanine
<220> FEATURE:
<221> NAME/KEY: VARIANT
<222> LOCATION: (7)
<223> OTHER INFORMATION: Thr or Ser
<220> FEATURE:
<221> NAME/KEY: VARIANT
<222> LOCATION: (8)
<223> OTHER INFORMATION: Ser or Thr
<220> FEATURE:
<221> NAME/KEY: VARIANT
<222> LOCATION: (9)
<223> OTHER INFORMATION: Asp or Glu
<220> FEATURE:
<221> NAME/KEY: VARIANT
<222> LOCATION: (10)
<223> OTHER INFORMATION: Leu, Ile, Val, pentylglycine or Met
<220> FEATURE:
<221> NAME/KEY: VARIANT
<222> LOCATION: (14)
<223> OTHER INFORMATION: Leu, Ile, pentylglycine, Val or Met
<220> FEATURE:
<221> NAME/KEY: VARIANT
<222> LOCATION: (22)
<223> OTHER INFORMATION: Phe, Tyr or naphthylalanine
<220> FEATURE:
<221> NAME/KEY: VARIANT
<222> LOCATION: (23)
<223> OTHER INFORMATION: Ile, Val, Leu, pentylglycine, tert-butylglycine
      or Met
```

```
<220> FEATURE:
<221> NAME/KEY: VARIANT
<222> LOCATION: (24)
<223> OTHER INFORMATION: Glu or Asp
<220> FEATURE:
<221> NAME/KEY: VARIANT
<222> LOCATION: (25)
<223> OTHER INFORMATION: Trp, Phe, Tyr or naphthylalanine
<220> FEATURE:
<221> NAME/KEY: VARIANT
<222> LOCATION: (31)
<223> OTHER INFORMATION: Pro, homoPro, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)
<223> OTHER INFORMATION: Pro, homoPro, 3Hyp, 4Hyp, thioproline,
      N-alkylglycine, N-alkylpentylglycine or N-alkylalanine
<220> FEATURE:
<221> NAME/KEY: VARIANT
<222> LOCATION: (37)
<223> OTHER INFORMATION: Pro, homoPro, 3Hyp, 4Hyp, thioproline,
      N-alkylglycine, N-alkylpentylglycine or N-alkylalanine
<220> FEATURE:
<221> NAME/KEY: VARIANT
<222> LOCATION: (38)
<223> OTHER INFORMATION: Pro, homoPro, 3Hyp, 4Hyp, thioproline,
      N-alkylglycine, N-alkylpentylglycine or N-alkylalanine
<220> FEATURE:
<221> NAME/KEY: VARIANT
<222> LOCATION: (39)
<223> OTHER INFORMATION: Ser, Thr or Tyr

<400> SEQUENCE: 35

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
            35

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine

<400> SEQUENCE: 36

Gly Gly Xaa Ser Ser
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine
```

```
<400> SEQUENCE: 37

Gly Gly Xaa Ser Ser Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine

<400> SEQUENCE: 38

Gly Gly Xaa Ser Ser Gly Ala
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (8)
<223> OTHER INFORMATION: Pro, homoproline, 3Hyp, 4Hyp, thioproline,
      N-alkylglycine, N-alkylpentylglycine or N-alkylalanine

<400> SEQUENCE: 39

Gly Gly Xaa Ser Ser Gly Ala Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (8)..(9)
<223> OTHER INFORMATION: Pro, homoproline, 3Hyp, 4Hyp, thioproline,
      N-alkylglycine, N-alkylpentylglycine or N-alkylalanine

<400> SEQUENCE: 40

Gly Gly Xaa Ser Ser Gly Ala Xaa Xaa
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (8)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (9)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (10)
<223> OTHER INFORMATION: Pro, homoproline, 3Hyp, 4Hyp, thioproline,
      N-alkylglycine, N-alkylpentylglycine or N-alkylalanine

<400> SEQUENCE: 41

Gly Gly Xaa Ser Ser Gly Ala Xaa Xaa Xaa
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, thioproline or
      N-methylalanine

<400> SEQUENCE: 42

Gly Gly Xaa Ser Ser
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, thioproline or
      N-methylalanine

<400> SEQUENCE: 43

Gly Gly Xaa Ser Ser Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, thioproline or
      N-methylalanine
```

```
<400> SEQUENCE: 44

Gly Gly Xaa Ser Ser Gly Ala
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, thioproline or
      N-methylalanine
<220> FEATURE:
<221> NAME/KEY: VARIANT
<222> LOCATION: (8)
<223> OTHER INFORMATION: Pro, homoproline, thioproline or
      N-methylalanine

<400> SEQUENCE: 45

Gly Gly Xaa Ser Ser Gly Ala Xaa
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, thioproline or
      N-methylalanine
<220> FEATURE:
<221> NAME/KEY: VARIANT
<222> LOCATION: (8)
<223> OTHER INFORMATION: Pro, homoproline, thioproline or
      N-methylalanine
<220> FEATURE:
<221> NAME/KEY: VARIANT
<222> LOCATION: (9)
<223> OTHER INFORMATION: Pro, homoproline, thioproline or
      N-methylalanine

<400> SEQUENCE: 46

Gly Gly Xaa Ser Ser Gly Ala Xaa Xaa
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, thioproline or
      N-methylalanine
<220> FEATURE:
<221> NAME/KEY: VARIANT
<222> LOCATION: (8)
<223> OTHER INFORMATION: Pro, homoproline, thioproline or
      N-methylalanine
```

```
-continued

<220> FEATURE:
<221> NAME/KEY: VARIANT
<222> LOCATION: (9)
<223> OTHER INFORMATION: Pro, homoproline, thioproline or
      N-methylalanine
<220> FEATURE:
<221> NAME/KEY: VARIANT
<222> LOCATION: (10)
<223> OTHER INFORMATION: Pro, homoproline, thioproline or
      N-methylalanine

<400> SEQUENCE: 47

Gly Gly Xaa Ser Ser Gly Ala Xaa Xaa Xaa
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (3)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (8)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (9)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (10)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (11)
<223> OTHER INFORMATION: Ser, Thr, Lys or Ala

<400> SEQUENCE: 48

Gly Gly Xaa Ser Ser Gly Ala Xaa Xaa Xaa Xaa
1               5                   10
```

EXENDIN-4 TO TREAT NONALCOHOLIC STEATOHEPATITIS AND NONALCOHOLIC FATTY LIVER DISEASE

RELATED APPLICATIONS

This application claims priority under §371 to PCT/US2006/032661 filed Aug. 21, 2006, which claims priority to U.S. Provisional Application No. 60/709,647 filed Aug. 19, 2005, U.S. Provisional Application No. 60/709,604 filed Aug. 19, 2005, and U.S. Provisional Application No. 60/779,216 filed Mar. 3, 2006, and this application also claims priority to PCT/US2006/032354 filed Aug. 18, 2006; each of the applications referred to herein are incorporated by reference in their entirety.

FIELD OF THE INVENTION

The present invention relates generally to the use of compounds referred to as incretin compounds (ICs) such as GLP-1, GIP, exendin, and agonists and analogs thereof, and amylin and amylinomimetics, for the treatment of metabolic diseases and disorders. More specifically the present invention relates to novel approaches to treating Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X).

BACKGROUND OF THE INVENTION

Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X) are conditions that can lead to diabetes or are themselves debilitating conditions.

Acute clinical management of these diseases and conditions, which may be complicated by hyperglycemia, can be especially challenging and often confusing for those not skilled in pharmacotherapy related to diabetes. Oral agents are often contraindicated (e.g., prior to surgery) or ineffective in some situations and, when needed, initiation of insulin therapy is difficult and cumbersome, given the required diabetes education, frequent glucose monitoring, and frequent regimen/dose titration. Further complicating the use of insulin is the potential for hypoglycemic episodes, perhaps the most significant hurdle to initiation of insulin therapy.

The need exists for methods to further address these conditions. Described herein are methods and compositions for meeting this need.

SUMMARY OF THE INVENTION

The present invention relates generally to the use of an incretin compound (IC) and/or an amylinomimetic, to treat, prevent or ameliorate metabolic diseases or disorders as described herein. Such metabolic diseases and conditions include Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X).

An "IC" as used herein refers to any compound that 1) can mimic an effect of an incretin hormone (incretin mimetic) or can bind to and activate a GLP-1 and/or GIP receptor. Further the IC can have a biological property of an incretin hormone, with the ability to stimulate release of insulin or to promote regeneration of beta cells or differentiation of cells into insulin-secreting cells, being activities of particular interest. These IC properties can be measured by assays known in the art and the assays herein described. Exemplary ICs include GLP-1, GIP, exendins (e.g. exendin-4), and an agonist, analog agonist and derivative agonist thereof. Exendin-4 peptides include: exendin-4, exendin-4(1-27), exendin-4(1-28), 14Leu,25Phe-exendin-4(1-28), and 5Ala,14Leu,25Phe-exendin-4(1-28). Also useful are exendin(7-15) and its Ser2 analog, HSEGTFTSD. In one embodiment the IC is exenatide (BYETTA®; Amylin Pharmaceuticals, Eli Lilly and Company).

In general, amylinomimetics are amylin and its agonists, analog agonists, and derivative agonists, which are recognized as compounds which, by directly or indirectly interacting or binding with one or more receptors, mimics an action of amylin. Exemplary amylinomimetics include pramlintide or amylin/sCT/amylin hybrids. Amylin peptides that exhibit at least one hormonal activity include amylin, amylin fragments such as amylin(1-17), amylin (1-16), amylin(1-15), and amylin(1-7), and amylin analogs such as pramlintide, 2Ala-h-amylin, 2,7Ala-h-amylin, and fragments thereof. Calcitonin peptides that exhibit at least one hormonal activity are sCT (salmon calcitonin), sCT fragments such as sCT (8-10), sCT (8-27), and, and calcitonin analogs such as 11,18Arg-sCT, 18Arg-sCT, 14Glu,18Arg-sCT, 14Glu,11, 18Arg-sCT, and fragments thereof. Amylin/sCT combinations useful in connection with the present invention include those disclosed in PCT/US2005/004631, which is herein incorporated by reference. Of particular interest is hAmylin (1-7)-11,18Arg-sCT (8-27)-Amylin (33-37), and analogs thereof.

In another aspect, the present invention relates to methods for using IC or amylinomimetic for the treatment of conditions associated with a metabolic disease or disorder as described herein. In another aspect, the present invention relates to methods of delaying or preventing conditions that result from a metabolic disease or disorder as described herein. Conditions associated with or resulting from a metabolic disease or disorder as described herein that can benefit from the methods of the invention include Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X).

In one embodiment a method for preventing, delaying, attenuating, or ameliorating a metabolic disease or disorder as described herein in a subject in need or desirous thereof is provided. The method comprises administering to the subject an amount of at least one IC and/or amylinomimetic effective to prevent or ameliorate a metabolic disease or disorder as described herein.

In one embodiment a long-acting release formulation of an IC and/or amylinomimetic is provided and used to treat, prevent or ameliorate a metabolic disease or condition described herein. In this regard, incorporated by reference in their entirety for the compositions, formulas and long-acting release formulations therein are commonly-owned U.S. Provisional Application 60/709,604, U.S. Provisional Application 60/779,216 and PCT international application PCT/US06/32354 Aug. 18, 2006.

In one embodiment the IC and/or amylinomimetic effects a beneficial change in alanine aminotransferase (ALT) in a subject in need thereof. Subjects having an initially high baseline ALT level as described herein are particularly benefited. In another embodiment the IC and/or amylinomimetic effects a beneficial change in aspartate aminotransferase (AST) levels in a subject in need thereof. In a further embodiment the subject is also suffering from diabetes. In one embodiment the IC or amylinomimetic is acutely administered to the subject. In another embodiment the IC or amylinomimetic is chronically administered to the subject. In any of the embodiments herein the at least one IC and/or amylinomimetic is provided as a long-acting release (LAR) composition. In addition the compositions can be parenterally administered to the subject.

BRIEF DESCRIPTION OF THE DRAWINGS

FIG. 5. (A-D) Body weight, ALT, AST, and $HbA_{1c}$ change from baseline stratified by 2-year weight-change quartiles. (E-H) Body weight, ALT, AST, and $HbA_{1c}$ change from baseline stratified by 2-year $HbA_{1c}$-change quartiles. Mean±SEM. N=283

FIG. 7. (A-D) Body weight, ALT, AST, and $HbA_{1c}$ change from baseline stratified by baseline ALT (Female ≦19 IU/L; Male ≦30 IU/L) and 2-year weight-change quartiles. (E-H) Body weight, ALT, AST, and $HbA_{1c}$ change from baseline stratified by baseline ALT (Female ≦19 IU/L; Male ≦30 IU/L) and 2-year $HbA_{1c}$-change quartiles. Mean+SEM. N=283

DETAILED DESCRIPTION OF THE INVENTION

Figure 1:
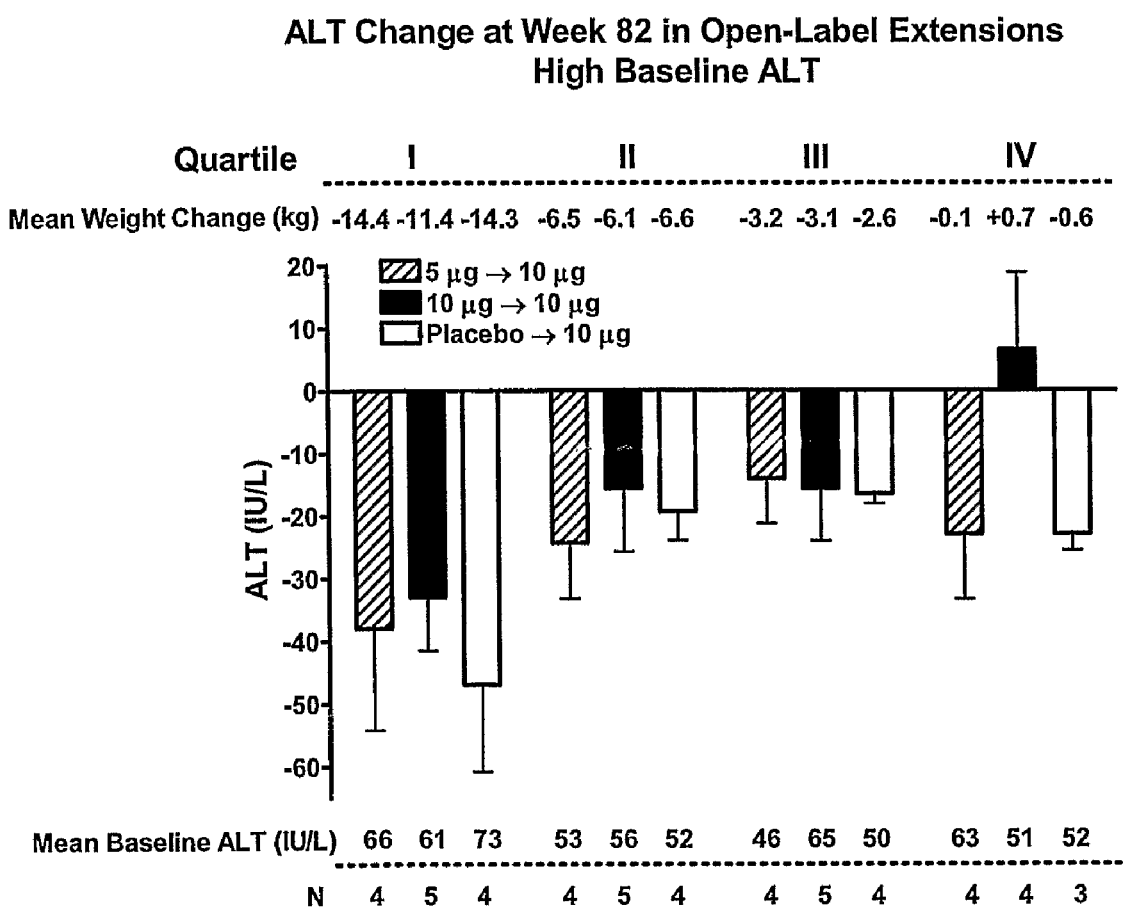
FIG. 1 depicts the effect of an IC on the change in alanine aminotransferase (ALT) level at week 82 in an open-label extension study, in subjects initially having a high baseline ALT level.

The present invention provides methods and compounds for clinical situations or conditions where hyperglycemia is an important factor, often in the absence of overt diabetes. Such situations include the metabolic diseases and conditions described herein. These metabolic diseases and conditions include Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X). The present invention is based on the discovery that the use of an incretin compound (IC) and/or an amylinomimetic is useful to treat, prevent or ameliorate such metabolic diseases or disorders as described herein.

An "IC" as used herein refers to any compound that 1) can mimic an effect of an incretin hormone (incretin mimetic) or can bind to and activate a GLP-1 and/or GIP receptor. Further the IC can have a biological property of an incretin hormone, with the ability to stimulate release of insulin or to promote regeneration of beta cells or differentiation of cells into insulin-secreting cells, being activities of particular interest. These IC properties can be measured by assays known in the art and the assays herein described. Exemplary ICs include GLP-1, GIP, exendins (e.g. exendin-4), and an agonist, analog agonist and derivative agonist thereof. Exendin-4 peptides include: exendin-4, exendin-4(1-27), exendin-4(1-28), 14Leu,25Phe-exendin-4(1-28), and 5Ala,14Leu,25Phe-exendin-4(1-28). Also useful are exendin(7-15) and its Ser2 analog, HSEGTFTSD. In one embodiment, the IC is exenatide (BYETTA®; Amylin Pharmaceuticals, Inc. San Diego, Calif., and Eli Lilly and Company). Useful polypeptide compounds having incretin and/or amylinomimetic activities include those disclosed in PCT/US05/04178, PCT international application PCT/US2006/031724 entitled "Hybrid Polypeptides with Selectable Properties" filed Aug. 11, 2006, and U.S. patent application Ser. No. 11/206,903 filed Aug. 17, 2005, and the GIP compounds disclosed in PCT/US06/005020 and U.S. patent application Ser. No. 11/507,081 filed Aug. 17, 2006.

In general, amylinomimetics are amylin and its agonists, analog agonists, and derivative agonists, which are recognized as compounds which, by directly or indirectly interacting or binding with one or more receptors, mimics an action of amylin. Exemplary amylinomimetics include pramlintide or amylin/sCT/amylin hybrids. Amylin peptides that exhibit at least one hormonal activity include amylin, amylin fragments such as amylin(1-17), amylin (1-16), amylin(1-15), and amylin(1-7), and amylin analogs such as pramlintide, 2Ala-h-amylin, 2,7Ala-h-amylin, and fragments thereof. Calcitonin peptides that exhibit at least one hormonal activity are sCT (salmon calcitonin), sCT fragments such as sCT (8-10), sCT (8-27), and, and calcitonin analogs such as 11,18Arg-sCT, 18Arg-sCT, 14Glu,18Arg-sCT, 14Glu,11,18Arg-sCT, and fragments thereof. Amylin/sCT combinations useful in connection with the present invention include those disclosed in PCT/US2005/004631 entitled "Amylin Family Agonist," which is herein incorporated by reference. Of particular interest is hAmylin(1-7)-11,18Arg-sCT (8-27)-Amylin(33-37), and analogs thereof.

In another aspect, the present invention relates to methods for using IC or amylinomimetic for the treatment of conditions associated with a metabolic disease or disorder as described herein. In another aspect, the present invention relates to methods of delaying or preventing conditions that result from a metabolic disease or disorder as described herein. Conditions associated with or resulting from a metabolic disease or disorder as described herein that can benefit from the methods of the invention include Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X).

In one embodiment a method for preventing, delaying, attenuating, or ameliorating a metabolic disease or disorder as described herein in a subject in need or desirous thereof is provided. The method comprises administering to the subject an amount of at least one IC and/or amylinomimetic effective to prevent or ameliorate a metabolic disease or disorder as described herein.

In one embodiment a long-acting release formulation of an IC and/or amylinomimetic is provided and used to treat, prevent or ameliorate a metabolic disease or condition described herein. In this regard is incorporated by reference in its entirety for the compositions, formulas and long-acting release formulations therein is commonly-owned U.S. Provisional Application U.S. Provisional Application 60/709,604, U.S. Provisional Application 60/779,216 and PCT international application PCT/US06/32354 filed Aug. 18, 2006

In one embodiment the IC and/or amylinomimetic effects a beneficial change in alanine aminotransferase (ALT) in a subject in need thereof. Subjects having an initially having a high baseline ALT level as described herein are particularly benefited. In another embodiment the IC and/or amylinomimetic effects a beneficial change in aspartate aminotransferase (AST) levels in a subject in need thereof. In a further embodiment the subject is also suffering from diabetes. In one embodiment the IC or amylinomimetic is acutely administered to the subject. In another embodiment the IC or amylinomimetic is chronically administered to the subject. In any of the embodiments herein the at least one IC and/or amylinomimetic is provided as a long-acting release (LAR) composition. In addition the compositions can be parenterally administered to the subject.

Acute clinical management of hyperglycemia, which is often associated with these conditions, can be especially challenging and often confusing for those not skilled in diabetes pharmacotherapy. Oral agents are often contraindicated (e.g., prior to surgery) or ineffective in some situations and, when needed, initiation of insulin therapy is difficult and cumbersome, given the required diabetes education, frequent glucose monitoring, and frequent regimen/dose titration. Further complicating the use of insulin is the potential for hypoglycemic episodes, perhaps the most significant hurdle to initiation of insulin therapy.

Pharmacotherapeutic agents as discussed herein overcome the many physician and subject barriers to achieving ideal glycemic control using insulin in these settings.

An estimated 6 million hospitalizations per year in the US are accompanied by hyperglycemia. Greater than 4.2 million hospitalizations occur annually among persons with diabetes. As many as 1.5 million hospitalized individuals have significant hyperglycemia but no history of diabetes. The degree of hyperglycemia in hospitalized subjects may be an important predictor of morbidity and mortality. It is essential to identify hyperglycemia at the time of hospital admission and to implement therapy to achieve blood glucose concentrations as close to normal as possible. However, it is well known that glycemic control in an inpatient setting is currently inadequate. Moreover, inpatient treatment of hyperglycemia is currently fraught with inappropriate dosing of hypoglycemic agents as well as poor monitoring of glucose response, often resulting in erratic glucose control.

It is estimated that 5.3 million Americans have undiagnosed diabetes. As many as one third of the patients who have significant hyperglycemia during a hospital admission do not have any history of diabetes. Given the estimated 10-year delay between the onset of diabetes and the time of diagnosis, there is a high likelihood that subjects exhibiting hyperglycemia without a history of glucose intolerance may indeed have undiagnosed diabetes. The beneficial impact of ameliorating hyperglycemia on improved overall clinical outcomes is realized irrespective of a formal diagnosis of diabetes. When circulating glucose concentrations are elevated, treatment should be initiated to re-establish near normal glycemia. Failure to recognize and to treat hyperglycemia represents a missed opportunity to reduce not only hospital morbidity and mortality, but to also initiate interventions that could delay the long-term complications of diabetes.

Accordingly the present invention generally provides methods for treating, preventing, delaying the onset of, attenuating, or ameliorating a metabolic disease or disorder as described herein, particularly those that may be associated with hyperglycemia. Conditions that can be benefited by the methods of the invention include Steroid Induced Diabetes, Human Immunodeficiency Virus (HIV) Treatment-Induced Diabetes, Latent Autoimmune Diabetes in Adults (LADA), Nonalcoholic Steatohepatitis (NASH) and Nonalcoholic Fatty Liver Disease (NAFLD), Hypoglycemia Unawareness (HA), Restrictive Lung Disease, Diabetes Development in Subjects with Congenital or HIV-Associated Lipoatrophy or "Fat Redistribution Syndrome", and Metabolic Syndrome (Syndrome X).

Steroid Induced Diabetes. Glucocorticoids are well known to affect carbohydrate metabolism. In response to exogenous glucocorticoid administration, increased hepatic glucose production and reduced insulin secretion and insulin-stimulated glucose uptake in peripheral tissues is observed. Furthermore, glucocorticoid treatment alters the proinsulin(PI)/immunoreactive insulin(IRI) ratio. Typical characteristics of the hyperglycemia induced by glucocorticoids in subjects without diabetes include a minimal elevation of fasting blood glucose, exaggerated postprandial hyperglycemia, insensitivity to exogenous insulin, and non-responsiveness to metformin or sulfonylurea therapy.

Glucocorticoids are commonly used in the treatment of several chronic and acute illnesses; such treatments can lead to worsening of pre-existing diabetes or precipitation of (steroid-induced) diabetes. Studies in renal transplant recipients receiving long-term treatment with corticosteroids have shown that steroid-induced diabetes develops in 6% to 25% of patients. In a case-control study of Medicaid patients aged 35 years or older, the relative risk of needing to initiate therapy for the treatment of hyperglycemia while receiving oral glucocorticoids was 2.23 when compared with the risk for non-users. The risk increased with increasing average daily steroid dose.

A study on physician attitudes regarding the treatment of new-onset steroid-induced diabetes showed that 43% of respondents agreed with the use of insulin and 44% with the use of sulfonylurea therapy. Diet therapy alone was ineffective at controlling hyperglycemia occurring following high-dose glucocorticoid administration. High doses of insulin were often required to control glycemia.

If the fasting blood glucose is greater than 200 mg/dL in the setting of glucocorticoid-induced hyperglycemia, it is unlikely that sulfonylurea therapy will be successful. Although there may be a role for metformin or a thiazolidinedione (TZD), not only are data supporting these treatment strategies limited, thiazolidinediones have a slow onset of action and metformin is often ineffective since postprandial rather than fasting hyperglycemia characterizes steroid-induced diabetes. Consequently, insulin use is often necessary in this setting.

Human Immunodeficiency Virus (HIV) Treatment-Induced Diabetes. Shortly after the introduction of human immunodeficiency virus (HIV)-1 protease inhibitors (PIs) into routine clinical use, reports linking PI use with the development of hyperglycemia began to appear. While approximately 1% to 6% of HIV-infected subjects who are treated with PIs will develop diabetes mellitus, a considerably larger proportion will develop insulin resistance and impaired glucose tolerance. Studies have reported a 16% to 46% incidence of impaired glucose tolerance and as high as 61% incidence of clinically significant insulin resistance among subjects treated with PIs.

Diabetes mellitus resulting from treatment with PIs has clinical characteristics similar to type 2 diabetes mellitus. Although the pathogenesis of PI treatment-associated diabetes is not well understood, some studies suggest that inhibition of glucose transport may provide one underlying mechanism. Consistent with worsened insulin resistance, these HIV-infected/PI-treated subjects often manifest hyperlipidemia, specifically hypertriglyceridemia. Moreover, abnormalities have been reported in the proinsulin/insulin ratio, a marker of beta-cell function, in PI-treated subjects with diabetes. The first-phase insulin response to intravenous glucose and the 30-minute insulin response to oral glucose failed to increase among prospectively evaluated nondiabetic subjects who developed insulin resistance while receiving the PI indinavir, indicating that PI use may indeed lead to defects in beta-cell function.

HIV infection often involves multiple organ systems. Furthermore, drug-drug interactions present a significant issue for these subjects, as extensive polypharmacy is a frequently necessity to provide adequate treatment of the disease. For these reasons, metformin and thiazolidinediones are often contraindicated for this subject population. While sulfonylureas and insulin are certainly possible treatment options for HIV-infected/PI-treated subjects who develop diabetes, the shortcomings and the undesired side effects of these medications remain problematic. Exendin-4 may prove to be highly beneficial in this clinical setting.

Latent Autoimmune Diabetes in Adults (LADA). Progressive autoimmune diabetes, also known as latent autoimmune diabetes in adults (LADA), (Latent Autoimmune Diabetes Adult (Zimmet, et al., Diabetes Med. 11:299 (1994)) is thought to be present in approximately 10% of patients diagnosed with type 2 diabetes. LADA patients have circulating antibodies to either islet cell cytoplasmic antigen or, more frequently, glutamic acid decarboxylase. These subjects exhibit clinical features characteristic of both type 1 and type 2 diabetes. Although insulin secretion is better preserved in the slowly progressing than in the rapidly progressing form of autoimmune diabetes, insulin secretion tends to deteriorate with time in LADA subjects.

In one embodiment an IC and/or amylinomimetic is administered to LADA subjects during early stages of the autoimmune beta-cell destruction. In another it is administered to subjects with already advanced autoimmune sequalae.

In one embodiment is combination therapy of an IC or amylinomimetic with a non-thiazolidinediones (non-TZDs) to treat LADA. Examples of non-TZDs include non-TZD agonists of a peroxisome proliferator-activated receptors (PPARs), particularly an alpha PPAR and/or a gamma PPAR. PPAR agonists may include non-TZD agonists of any of the PPAR subunits or combinations thereof. For example, PPAR agonist may include agonists of PPAR-alpha or PPAR-gamma or both. PPARs are members of the nuclear receptor superfamily of ligand-activated transcription factors. Three subtypes of PPARs have been isolated from mouse and human sources, i.e., PPAR alpha, PPAR gamma, and PPAR delta (Wilson et al., Ann. Rev. Bioch. 70:341-367 (2001)). Non-TZD compounds which activate PPARs include, but are not limited to non-TZDs that can activate any combination of the three PPARs (e.g. JTT-501, LSN862, DRF 4832, LM 4156, LY 510929, LY 519818, TY 51501, X 334, tesaglitazar, farglitazar, GW-7282, TAK-559, T-131, RG-12525, LY-510929, LY-519818, BMS-298585, DRF-2725, GW-1536, GI-262570, TZD18 (Merck), DRF-2655, and the like), certain tyrosine-based derivatives (e.g. GW1929, GW7845), phenylacetic acid-based derivatives, phenoxazine phenyl propanoic acid derivatives (e.g. DRF2725, DRF2189), cinammic and dihydrocinammic acid-based derivatives (e.g. tesaglitazar (AZ242)), and 3-phenyl-7-propylbenzisoxazoles (Adams et al., Bioorg. Med. Chem. Lett. 13:931-5(2003)). Although some compounds primarily activate PPAR alpha alone or PPAR delta alone, more commonly such compounds also activate, to least some degree, PPAR gamma. Non-TZD compounds which antagonize the angiotensin II type 1 receptor and also activate PPAR gamma include 2-methyl-2-[4-(2-[5-methyl-2-aryloxazol-4-yl] ethoxy)phenoxy]propionic acid PPAR alpha/gamma agonist derivatives (Brooks et al., J. Med. Chem. 44:2061-4 (2001)) N-(2-Benzoylphenyl)-L-tyrosine PPAR gamma agonists (Henke et al., J. Med. Chem. 41:5020-36 (1998)); dihydrocinnamate PPAR alpha/gamma agonist derivatives (Cronet et al., Structure 9:699-706 (2001)). Another angiotensin II type 1 receptor blocker (ARB) which can be optionally derivatized to also fully or partially activate PPAR gamma are heterocyclic benzimidazoles (U.S. Pat. No. 6,100,252).

Non-TZD compounds, such as those above, can be used in combination with an IC or amylinomimetic to treat and/or prevent the metabolic diseases and disorders as described herein.

Nonalcoholic Steatohepatitis (NASH) and Nonalcoholic Fatty Liver Disease (NAFLD). NASH is now considered to be one of the most common liver diseases in western countries. Fatty infiltration is a typical response of the liver to a wide array of noxious stimuli, including hypoxia, toxins, systemic inflammation, malignancies, and various metabolic derangements. Although NASH itself is generally considered to be a benign condition, it may lead to liver fibrosis, cirrhosis, and ultimately failure. NASH is a subcategory of NAFLD characterized histologically by macrovesicular steatosis, ballooning degeneration, hepatocyte necrosis, fibrosis, occasional Mallory bodies, and infiltration of inflammatory cells (American Gastroenterological Association, Technical review on nonalcoholic fatty liver disease. Gastroenterology 123:1705-1725 (2002)). Although NAFLD and NASH are often asymptomatic, elevated concentrations of serum alanine aminotransferase (ALT), a biochemical marker of liver injury, are indicative of NAFLD, but cannot distinguish between NAFLD and NASH (American Gastroenterological Association, Medical position statement: Nonalcoholic fatty liver disease. Gastroenterology 123:1702-1704 (2002)). Serum concentrations of aspartate aminotransferase (AST) may be higher than ALT, especially in the presence of hepatic cirrhosis, and serum alkaline phosphatase (ALP) concentrations may also be elevated (American Gastroenterological Association, Medical position statement: Nonalcoholic fatty liver disease. Gastroenterology 123:1702-1704 (2002)). However, measures of hepatic functional capacity do not become abnormal until cirrhosis has developed and liver failure is imminent (American Gastroenterological Association, Medical position statement: Nonalcoholic fatty liver disease. Gastroenterology 123:1702-1704 (2002)). In obese T2DM, progressive hepatomegaly due to NAFLD occurs frequently and may be accompanied by right upper quadrant discomfort. NAFLD can cause progressive fibrosis leading to cirrhosis and its complications, including portal hypertension and liver failure (American Gastroenterological Association, Medical position statement: Nonalcoholic fatty liver disease. Gastroenterology 123:1702-1704 (2002)). In addition, NASH is associated with decreased insulin-mediated suppression of lipolysis and the resulting elevation in serum free fatty acid concentrations that contribute to impaired pancreatic β-cell function and increased cardiovascular morbidity and mortality (Yki-Järvinen et al., Curr. Molec. Med. 5:287-295 (2005); American Gastroenterological Association, Medical position statement: Nonalcoholic fatty liver disease. Gastroenterology 123:1702-1704 (2002); Raz et al., Diabetes/Metab. Res. Rev. 21:3-14 (2005)).

Fatty liver is most prevalent in individuals who are obese or who have diabetes, although the reason for this is unclear. Because of the interdependence of glucose, insulin, and free fatty acids in energy homeostasis/fluxes, it is difficult to determine the primacy of any one factor. However, relative insulin deficiency in type 2 diabetes, glucose toxicity, and increased hepatic free fatty acid burden through elevated delivery from intra-abdominal adipose tissue via the portal vein, have all been implicated as possible causes. It has been hypothesized that eating behavior is the key factor driving the metabolic syndrome of obesity with its many corollaries, including NASH. Treatments aimed at decreasing food intake and increasing the number of small meals, as has already been demonstrated in type 2 diabetes, should effectively treat and prevent NASH. Drugs that promote insulin secretion and weight loss, and delay gastric emptying are also effective at improving glucose tolerance and thus may improve fatty liver with its attendant hyperinsulinemia. While more research is needed to elucidate the pathophysiology and possible therapeutic approaches suitable for NASH, us of an IC or amylinomimetic, such as exendin, exendin analog agonist, exendin derivative agonist, particularly exenatide, appears to be well suited as a treatment modality for this condition. Biguanides or thiazolidinediones, although reported to reverse insulin resistance to varying degrees, is relatively or absolutely contraindicated in those subjects with existing liver abnormalities.

Hypoglycemia Unawareness (HU). The Diabetes Control and Complications Trial (DCCT), a ten-year study completed in mid-1993, demonstrated that tight or "intensive" control of blood glucose levels—i.e. frequent self-monitoring of glucose levels and maintenance of these levels as close as possible to those in nondiabetics, significantly reduces diabetes-associated complications, such as retinopathy, nephropathy and neuropathy (DCCT Research Group 1993). As defined in the DCCT, "intensive" control meant that the diabetic subject followed a strict regimen, including controlling glucose tightly by three or more daily insulin injections or by means of an insulin pump. Intensive control was distinguished from a more moderate regimen termed "conventional" control, which included only one or two injections of insulin a day and less frequent monitoring of blood glucose concentration. The DCCT showed that the frequency of health complications was 40-75% lower for persons in the intensive control group than for those in the conventional treatment group (DCCT Research Group 1993). It has since become a central doctrine of diabetic management that the intensive control of hyperglycemia is critical to effective retardation or delay in the appearance or progression of the late complications of the disease.

Diabetic patients are taught to recognize the signs of impending hypoglycemia and insulin shock (e.g., headache, hunger, nervousness, irritability, diaphoresis, thready pulse, tremors and slurred speech). Hypoglycemia can be seen in both subsets of diabetics (IDDM and NIDDM) and is caused by either too much insulin or inadequate caloric intake (CDC Guide). However, it was also found in the DCCT that subjects in the intensive treatment group more often suffered from seizures or coma or required another person's assistance to recover from hypoglycemia than did subjects treated less intensively. The chief adverse complication associated with intensive therapy was 3-fold increase in the incidence of severe hypoglycemia, defined as the need for assistance from others, as compared to diabetics undertaking conventional therapy (DCCT Research Group 1993).

This observation is attributed to the unusual and interesting feature of the brain that, while like other organs systems in its reliance on blood glucose concentration for function, the brain differs from other organs in that it does not need insulin to utilize glucose. Boyle et al. (N. Engl. J. Med. 333(26): 1726-31 (1995)) have reported that hypoglycemia is likely to lead to a reversible, maladaptive central nervous system tolerance to subnormal plasma glucose concentrations. Specifically, certain autonomic portions of the brain adapt physiologically, learning to tolerate low blood glucose levels. By contrast, the rest of the brain, and in particular the cognitive portions, do not possess this capacity. Defective glucose counterregulation can occur even after only a single recent episode of hypoglycemia. Subjects who experience repeated episodes of hypoglycemia often lose their capacity to recognize the symptoms typically associated with hypoglycemia or impending insulin shock, a condition called "hypoglycemia unawareness". Because the patient doesn't appreciate his or her own status, blood glucose levels can then fall so low that serious neurological problems ensue, including coma and seizure.

Thus, the danger in maintaining artificially a subject's blood glucose within the narrow, normal range (the essence of intensive control prescribed according to the DCCT) is that such regimens can induce recurrent low blood-glucose levels, raising the threat of seizure or a coma with little or no warning. Tight control of the blood glucose levels poses a difficult dilemma. Specifically, while tight control of blood glucose levels appears to be required to control hyperglycemia-associated pathology, in practice the subject often overcorrects, thereby inducing repeated episodes of hypoglycemia, giving rise to "hypoglycemia unawareness".

Enhancing response of counterregulatory hormones during episodes of hypoglycemia unawareness effects type 1 diabetics most dramatically. However, it also effects type 2 diabetics that are faced with hypoglycemia. Counterregulatory hormones counter insulin to maintain glucose levels. Both ICs and amylinomimetics can reduce or inhibit glucagon secretion. Glucagon is a counterregulatory hormone. However, glucagon is unchanged during Hypoglycemia Unawareness. CCK and catecholamine are increased during counterregulatory hormone response (CRH).

IC or amylinomimetics can provide a more robust CRH response allowing faster or better recovery from HU. An IC and/or amylinomimetic can smooth glucose dips throughout the day, e.g. "smoothing" the 7-point glucose curve. Subjects with type I diabetes having impaired hypoglycemic awareness will exhibit an improve state by increasing CRH response. Consequently, the method of the invention allows for the subject to lead a more normal life wherein the risk of complications from hypoglycemia such as coma or seizure related to hypoglycemia unawareness is reduced. The invention finds particular utility in the treatment of subjects suffering from insulin-dependent diabetes mellitus and having a history of episodic unawareness of hypoglycemia. The method finds utility in treating a subject having insulin-dependent diabetes mellitus and insulin-associated abnormal central nervous system tolerance to subnormal plasma glucose concentration. Thus, the method is useful for reducing hypoglycemia-associated neurological complications in a subject suffering from insulin-dependent diabetes mellitus or non-insulin-dependent diabetes mellitus.

Restrictive Lung Disease. GLP1 receptor has been localized in the lung. An GLP-1 or exendin compound will improve elasticity of lung or delay rigidity. In yet another embodiment an increase in pulmonary function is achieved.

High levels of the GLP-1 receptor and of its own messenger RNA (mRNA) have been found in rat lung. These receptors have been detected in the submucosal glands of the trachea and the smooth muscle of the pulmonary arteries, where ligands produce increases in mucous secretion and pulmonary smooth muscle relaxation, respectively. In addition, in situ hybridization experiments have identified GLP-1 receptor mRNA in cells morphologically considered type II pneumocytes that are involved in the synthesis and secretion of pulmonary surfactant in alveolar regions. Surfactant is a complex mixture of lipids and proteins that reduces the tension at the air-alveolar interface in the lung and provides for alveolar stability.

Sarcoidosis is a systemic granulomatous disease that frequently involves the lung. Although classically thought of as a restrictive lung disease, airway obstruction has become a recognized feature of the disease in the past years. Sarcoidosis can affect the airway at any level and when the involvement includes small airways, it can resemble more common obstructive airway diseases, such as asthma and chronic bronchitis. Pulmonary function testing and high-resolution computerized tomography of the chest are two important tools to evaluate the presence and extent of airway obstruction in sarcoidosis. Pharmacologic options for the treatment of obstructive sarcoidosis are, in large part, not supported by large, randomized clinical trials. In severe cases of bronchostenosis owing to sarcoidosis granuloma or extrinsic compression from intrathoracic lymphadenopathy, interventional bronchoscopy has successfully been performed, although repeated procedures are usually required. Lung transplantation is an ultimate option in selected subjects with late-stage fibrotic disease. Accordingly, in one embodiment sarcoidosis is an metabolic disease treatable as discussed herein.

Metabolic Syndrome X. Metabolic Syndrome X is characterized by insulin resistance, dyslipidemia, hypertension, and visceral distribution of adipose tissue, and plays a pivotal role in the pathophysiology of type 2 diabetes. It has also been found to be strongly correlated with NASH (nonalcoholic steatohepatitis), fibrosis, and cirrhosis of the liver.

The section headings are used herein for organizational purposes only, and are not to be construed as in any way limiting the subject matter described.

A. Exemplary Methods

In an aspect of the present invention, a metabolic disease or disorder as described herein is prevented, delayed, attenuated, or ameliorated by the administration of an IC or amylinomimetic. In the context of the present invention, prevention or amelioration of a metabolic disease or disorder as described herein can include a reduction of a metabolic disease or disorder as described herein by any amount.

In an embodiment, a metabolic disease or disorder as described herein is ameliorated or reduced to an amount that is less than about 1%, 2%, 5%, 10%, 20%, 30%, 40%, 50%, 60%, 70%, 80%, or 90% of the amount of a metabolic disease or disorder as described herein in the absence of administering an IC or amylinomimetic. In another embodiment, a metabolic disease or disorder as described herein can be slightly reduced, moderately reduced, substantially reduced, or substantially eliminated, as compared to the occurrence of a metabolic disease or disorder as described herein in the absence of administering an IC or amylinomimetic. As used herein, a slight reduction of a metabolic disease or disorder as described herein refers to a metabolic disease or disorder as described herein that is decreased by about 25% or less as compared with a metabolic disease or disorder as described herein in the absence of administering an IC or amylinomimetic. A moderate reduction in a metabolic disease or disorder as described herein refers to a metabolic disease or disorder as described herein that decreased by about 50% or less as compared with a metabolic disease or disorder as described herein in the absence of administering an IC or amylinomimetic. A substantial reduction in a metabolic disease or disorder as described herein refers to a metabolic disease or disorder as described herein that decreased by about 80% or less as compared with a metabolic disease or disorder as described herein in the absence of administering an IC or amylinomimetic. A substantial elimination of a metabolic disease or disorder as described herein refers to a metabolic disease or disorder as described herein that is decreased by about 80% or more as compared with a metabolic disease or disorder as described herein in the absence of administering an IC or amylinomimetic.

In order to assess the degree to which a metabolic disease or disorder as described herein is treated, prevented, ameliorated, attenuated or delayed, any means available to the skilled worker in the art can be employed. For example, a metabolic disease or disorder as described herein can be assessed by analyses including but not limited to non-invasive examination of the relevant organ, tissue or cell, or measurement of an chemical or biochemical marker.

In one embodiment, the methods of the present invention contemplate administering to a subject an amount of one or more IC and/or amylinomimetics effective in treating, preventing, delaying, attenuating or ameliorating a metabolic disease or disorder as described herein.

A "subject" may include any mammal, including humans. A "subject" may also include domesticated animals (e.g., dogs, cats, horses), as well as other valuable animals. Subject of the invention may have at least one of the metabolic diseases or conditions described herein. Subjects who may benefit from the methods of the invention may be overweight or obese; however, they may also be lean. They may have a metabolic disorder or condition in addition to a one of those described herein. Subject of the invention can be of any age. Accordingly, these disorders can be found in young adults and adults (defined herein as those aged 65 or under) as well as infants, children, adolescents, and the elderly (defined herein as over the age of 65). In fact, certain segments of the population may be particularly prone to having a particular condition, such as eating disorders in adolescents and young adults.

In an embodiment of the present invention, subjects that may be benefited by administration of an IC or amylinomimetic to treat, prevent, ameliorate, attenuate, or delay a metabolic disease or disorder as described herein, can be ascertained by the clinician in light of conditions and risk factors related to the subject. In one embodiment of the present invention, subjects may be in need of treatment, prevention, amelioration, attenuation, or delay of a metabolic disease or disorder as described herein. In another embodiment, the subject may be desirous of treating, preventing, ameliorating, attenuating or delaying a metabolic disease or disorder as described herein. Subjects include those who have experienced, are experiencing or are at risk to experience a condition associated with a metabolic disease or disorder as described herein.

In accordance with the methods of the present invention, an IC or amylinomimetic may be administered in any manner known in the art that renders an IC or amylinomimetic biologically available to the subject in an effective amount. For example, the IC or amylinomimetic may be administered to a subject via any central or peripheral route known in the art including, but not limited to: oral, parenteral, transdermal, transmucosal, or pulmonary routes. In one embodiment is parenteral administration. Exemplary routes of administration include oral, ocular, rectal, buccal, topical, nasal, ophthalmic, subcutaneous, intramuscular, intravenous, intracerebral, transdermal, and pulmonary. A particularly useful route of administration is subcutaneous. Further, the IC or amylinomimetic can be administered to a sample via pouring, pipetting, immersing, injecting, infusing, perfusing, or any other means known in the art. Determination of the appropriate administration method is usually made upon consideration of the condition (e.g., disease or disorder) to be treated, the stage of the condition (e.g., disease or disorder), the comfort of the subject, and other factors known to those of skill in the art.

Administration by the methods of the present invention can be intermittent or continuous, both on an acute and/or chronic basis. One mode of administration of an IC or amylinomimetic is continuous. Continuous intravenous or subcutaneous infusion, and continuous transcutaneous infusion are exemplary embodiments of administration for use in the methods of the present invention. Subcutaneous infusions, both acute and chronic, are particularly useful embodiments of continuous administration. Another exemplary mode of administration is intermittent subcutaneous injection. In another exemplary mode of administration, the IC or amylinomimetic is formulated for extended or sustained release. Exemplary formulations are reported for example in WO2005000222, US20040228833, US20040208929, US 20050031549, and US20050002927, the entireties of which are incorporated herein by reference In one embodiment, administration of an IC or amylinomimetic to prevent or delay a metabolic disease or disorder as described herein can be a prophylactic treatment, beginning concurrently with the diagnosis of conditions (e.g., disease or disorder) which places a subject at risk of a metabolic disease or disorder as described herein. In the alternative, administration of an IC or amylinomimetic to treat, prevent, ameliorate, attenuate, or delay a metabolic disease or disorder as described herein can occur subsequent to occurrence of an insult or symptoms associated with a metabolic disease or disorder as described herein. In certain embodiments, methods of the invention comprise administering an IC or amylinomimetic for more than 1 week, 2 weeks, 3 weeks, 1 month, 2 months, 3 months, 6 months, 1 year, or 2 years after the start of the IC or amylinomimetic treatment. In certain embodiments, treatment with an IC or amylinomimetic may continue for the duration of the condition, or for the life of the subject.

The term "effective amount" refers to an amount of a pharmaceutical agent used to treat, ameliorate, prevent, or eliminate the identified condition (e.g., disease or disorder), or to exhibit a detectable therapeutic or preventative effect. The effect can be detected by, for example, chemical or biochemical markers, antigen levels, relevant organ, tissue or cell function (e.g. liver and liver markers for NASH or NAFLD), physical measurements of the relevant organ, tissue or cell, or time to a measurable event, such as morbidity or mortality. Therapeutic effects include preventing or reducing the risk of or lessening the severity of a metabolic disease or condition or a symptom associated therewith. Further therapeutic effects include reduction in a subject's physical symptom(s) known to relevant to the condition or disease. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician.

For any IC or amylinomimetic, the effective amount can be estimated initially either in cell culture assays, e.g. in animal models, such as rat or mouse models. An animal model may also be used to determine the appropriate concentration range and route of administration. Such information can then be used to determine useful doses and routes for administration in humans.

Efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are useful. The data obtained from cell culture assays and animal studies may be used in formulating a range of doses for human use. The dosage contained in such compositions is in some embodiments within a range of circulating concentrations that include an $ED_{50}$ with little or no toxicity. The dosage may vary within this range depending upon the dosage form employed, sensitivity of the subject, and the route of administration.

More specifically, the concentration-biological effect relationships observed with regard to IC or amylinomimetic employed in the methods of the present invention indicate an initial target plasma concentration as discussed herein. In one embodiment an initial target plasma concentration can range from about 5 pM to about 400 pM, even from about 20 pM to about 200 pM, and even from about 80 pM to about 100 pM. To achieve such plasma concentrations in the methods of the present invention, an IC or amylinomimetic can be administered at doses that vary as discussed herein. In one embodiment it can be from about 0.25 pmol/kg/min to about 10 nmol/kg/min, and even about 0.45 pmol/kg/min to about 4.5 nmol/kg/min, depending upon the route of administration. Guidance as to particular dosages and methods of delivery is generally available to practitioners in the art and is provided herein.

In general, for continuous subcutaneous infusion, the dose can be as discussed herein. In one embodiment a dose can be in the range of about 0.2 pmol/kg/min to about 35 pmol/kg/min, or from about 0.3 pmol/kg/min to about 30 pmol/kg/min, or in some embodiments from about 0.45 pmol/kg/min to about 25 pmol/kg/min. For acute subcutaneous infusion, the dose will generally be in the range of about 2.5 pmol/kg/min to about 7 nmol/kg/min, or from about 3.5 pmol/kg/min to about 6 pmol/kg/min, or in some embodiments from about 5 pmol/kg/min to about 4.5 nmol/kg/min. Exemplary treatment regimens include, but are not limited to, administration via injection to achieve a dose of from about 0.1 µg/kg to about 0.5 µg/kg or from about 0.005 µg/kg to about 0.2 µg/kg of the IC or amylinomimetic. Other exemplary treatment regimens include, but are not limited to, administration via injection, e.g., iv or sc, to achieve a dose of from about 1 µg/day to about 1 mg/day, from about 100 ug/day to 800 ug/day, from about 400 ug/day to about 600 ug/day, or from about 500 µg/day to about 12,000 µg/day of the IC or amylinomimetic in a single or divided dose.

Still other exemplary treatment regimens include, but are not limited to, pulmonary administration to achieve a dose from about 1 µg/day to about 1 mg/day, from about 100 µg/day to about 12,000 µg/day, from about 100 ug/day to 800 ug/day or from about 400 ug/day to about 600 ug/day, of the IC or amylinomimetic in a single or divided dose; nasal administration to achieve a dose from about 10 µg/day to about 12,000 µg/day, from about 100 ug/day to 800 ug/day or from about 400 ug/day to about 600 ug/day, of the IC or amylinomimetic in a single or divided dose; and buccal administration to achieve a dose from about 100 µg/day to about 12,000 µg/day of the IC or amylinomimetic in a single or divided dose.

The exact dosage will be determined by the practitioner, in light of factors related to the subject.

Chronic administration of or treatment with the IC or amylinomimetic for the treatment, prevention, attenuation, delay, or amelioration of a metabolic disease or disorder as described herein may be warranted where no particular transient event or transient condition associated with a metabolic disease or disorder as described herein is identified. Chronic administration includes administration of an IC or amylinomimetic over an indefinite period of time on the basis of a general predisposition to a metabolic disease or disorder as described herein or on the basis of a predisposing condition that is non-transient (e.g., a condition that is non-transient may be unidentified or unamenable to elimination, such as diabetes).

In a further aspect of the present invention, prophylactic and therapeutic methods are provided. Treatment on an acute or chronic basis is contemplated. In addition, treatment on an acute basis may be extended to chronic treatment, if so indicated. Chronic treatment is contemplated as being longer than 2 weeks. In certain embodiments, chronic treatment may be longer than 1 month, 3 months, 6 months, 1 year, 2 years, 5 years, or over a life. In one aspect, the present invention includes a method for the treatment or prevention of a condition associated with a metabolic disease or disorder as described herein in a subject in need thereof. The method generally comprises administering to the subject an amount of an IC or amylinomimetic effective to prevent or ameliorate a metabolic disease or disorder as described herein, wherein the condition associated with remodeling is thereby improved, prevented or delayed. As described herein, administration of an IC or amylinomimetic may be done in any manner and with any IC or amylinomimetic such as GLP-1, GIP, exendin, pramlintide and their analogs and agonists.

In yet another embodiment of the invention, the methods of the present invention further comprise the identification of a subject in need of treatment. Any effective criteria may be used to determine that a subject may benefit from administration of an IC or amylinomimetic. Methods for the diagnosis of the metabolic diseases and conditions herein as well as procedures for the identification of individuals at risk for development of these conditions, are well known to those in the art. Such procedures may include clinical tests, physical examination, personal interviews and assessment of family history.

B. Exemplary Incretin Compounds (ICs)

Examples of incretin mimetics (and ICs) include GLP-1, exendins, GIP, and their analogs and agonists. An agonist of GLP-1 or exendin can be any molecule that has at least one activity or function of GLP-1 or exendin, respectively, as known in the art or herein described. An agonist of GLP-1 or exendin can be any molecule that can bind to a GLP-1 receptor. An agonist may be a peptide or non-peptide, such as a small molecule.

Accordingly, in one embodiment, an IC may be identified by its ability to bind or activate a GLP-1 and/or GIP receptor (e.g., a GLP-1 receptor agonist). A GLP-1 receptor is a cell-surface protein. In this regard, an IC includes any molecule that binds to or activates a GLP-1 receptor.

Generally, GLP-1 receptor agonists can include peptides and small molecules, as known in the art. Exemplary GLP-1 receptor agonists have been described, such as those in Drucker, *Endocrinology* 144(12):5145-5148 (2003); EP 0708179; Hjorth et al., *J. Biol. Chem.* 269(48): 30121-30124 (1994); Siegel et al., Amer. Diabetes Assoc. 57$^{th}$ Scientific Sessions, Boston (1997); Hareter et al., Amer. Diabetes Assoc. 57$^{th}$ Scientific Sessions, Boston (1997); Adelhorst et al., *J. Biol. Chem.* 269(9): 6275-6278 (1994); Deacon et al., 16$^{th}$ International Diabetes Federation Congress Abstracts, *Diabetologia Supplement* (1997); Irwin et al., *Proc. Natl. Acad. Sci. USA.* 94: 7915-7920 (1997); Mosjov, *Int. J Peptide Protein Res.* 40: 333-343 (1992); Göke et al., *Diabetic Medicine* 13: 854-860 (1996). Publications also disclose Black Widow GLP-1 and Ser$^2$ GLP-1. See Holz et al., *Comparative Biochemistry and Physiology, Part B* 121: 177-184 (1998) and Ritzel et al., "A synthetic glucagon-like peptide-1 analog with improved plasma stability," *J. Endocrinol.* 159(1): 93-102 (1998).

In order to determine the ability of a molecule to bind or activate a GIP or GLP-1 receptor, any available means can be used. In one embodiment, GIP or GLP-1 receptor binding or activation can be determined in either an in vitro or an in vivo model. In one embodiment, receptor-binding activity screening procedures may be used, such as for example, providing any cells that express a GLP-1 or a GIP receptor on the surface and measuring specific binding using radioimmunoassay methods. The cells expressing a GLP-1 or a GIP receptor can be naturally occurring or genetically modified. In one aspect, GLP-1 or GIP receptor binding or activation can be determined with the aid of combinatorial chemistry libraries and high throughput screening techniques, as is known in the art.

In one embodiment, ICs include exendin molecules, including exendin-1, exendin-2, exendin-3, exendin-4, and analogs thereof. In one embodiment exendin molecules include exendin-3 and exendin-4, and analogs thereof. Such exendin molecules are generally known in the art and available to the skilled artisan.

By way of background, exendins are peptides that are found in the saliva of the Gila-monster, a lizard endogenous to Arizona, and the Mexican Beaded Lizard. Exendin-3 is present in the saliva of *Heloderma horridum*, and exendin-4 is present in the saliva of *Heloderma suspectum* (Eng, J., et al., *J. Biol. Chem.*, 265:20259-62 (1990); Eng., J., et al., *J. Biol. Chem.*, 267:7402-05 (1992)). The exendins have some sequence similarity to several members of the glucagon-like peptide family, with the highest identity, 53%, being to GLP-1 (Goke, et al., *J. Biol. Chem.*, 268:19650-55 (1993)).

Exendin-4 is a potent agonist at GLP-1 receptors on insulin-secreting TC1 cells, at dispersed acinar cells from guinea pig pancreas, and at parietal cells from stomach; the peptide also stimulates somatostatin release and inhibits gastrin release in isolated stomachs (Goke, et al., *J. Biol. Chem.*, 268:19650-55 (1993); Schepp, et al., *Eur. J. Pharmacol.*, 69:183-91 (1994); Eissele, et al., *Life Sci.*, 55:629-34 (1994)). Exendin-3 and exendin-4 were found to be GLP-1 agonists in stimulating cAMP production in, and amylase release from, pancreatic acinar cells (Malhotra, R., et al., *Regulatory Peptides*, 41:149-56 (1992); Raufman, et al., *J. Biol. Chem.*, 267:21432-37 (1992); Singh, et al., *Regul. Pept.*, 53:47-59 (1994)). The use of the insulinotropic activities of exendin-3 and exendin-4 for the treatment of diabetes mellitus and the prevention of hyperglycemia have been proposed (Eng, U.S. Pat. No. 5,424,286).

Truncated exendin peptides such as exendin[9-39], a carboxyamidated molecule, and fragments 3-39 through 9-39 have been reported to be potent and selective antagonists of GLP-1 (Goke, et al, *J. Biol. Chem.*, 268:19650-55 (1993); Raufman, J. P., et al., *J. Biol. Chem.*, 266:2897-902 (1991); Schepp, W., et al., *Eur. J. Pharm.*, 269:183-91 (1994); Montrose-Rafizadeh, et al., *Diabetes*, 45(Suppl. 2):152A (1996)). Exendin[9-39] blocks endogenous GLP-1 in vivo, resulting in reduced insulin secretion (Wang, et al., *J. Clin. Invest.*, 95:417-21 (1995); D'Alessio, et al., *J. Clin. Invest.*, 97:133-38 (1996)). The receptor apparently responsible for the insulinotropic effect of GLP-1 has been cloned from rat pancreatic islet cells (Thorens, B., *Proc. Natl. Acad. Sci. USA* 89:8641-8645 (1992)). Exendins and exendin[9-39] bind to the cloned GLP-1 receptor (rat pancreatic-cell GLP-1 receptor: Fehmann H C, et al., *Peptides*, 15 (3): 453-6 (1994); human GLP-1 receptor: Thorens B, et al., *Diabetes*, 42 (11): 1678-82 (1993)). In cells transfected with the cloned GLP-1 receptor, exendin-4 is an agonist, i.e., it increases cAMP, while exendin [9-39] is an antagonist, i.e., it blocks the stimulatory actions of exendin-4 and GLP-1. Id.

Certain exendin compounds useful in the present invention include those disclosed in PCT/US98/16387, PCT/US98/24210, and PCT/US98/24273, all of which are herein incorporated by reference in their entireties.

In one embodiment an exendin analog can have one or more amino acid substitutions, deletions, inversion, or additions compared to a native or naturally occurring exendin. Thus, exendin analogs can have an amino acid sequence that has one or more amino acid substitutions, additions or deletions as compared with a naturally occurring exendin, for example, exendin-4. In one embodiment, an exendin analog has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring exendin, such as exendin-4.

More particularly, exendin compounds include exendin peptide analogs in which one or more naturally occurring amino acids are eliminated or replaced with another amino acid(s). In one embodiment exendin compounds are agonist analogs of exendin-4. In addition to exendin-3 [His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser], and exendin-4 [His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser], particularly useful exendin compounds include exendin-4 (1-30) [His Gly Glu Gly Thr Phe Thr Ser Asp Leu Ser Lys Gln Met Glu Glu Glu Ala Val Arg Leu Phe Ile Glu Trp Leu Lys Asn Gly Gly], exendin-4 (1-30) amide [His Gly Glu Gly Thr Phe Thr Ser Asp Leu Ser Lys Gln Met Glu Glu Glu Ala Val Arg Leu Phe Ile Glu Trp Leu Lys Asn Gly Gly-$NH_2$], exendin-4 (1-28) amide [His Gly Glu Gly Thr Phe Thr Ser Asp Leu Ser Lys Gln Met Glu Glu Glu Ala Val Arg Leu Phe Ile Glu Trp Leu Lys Asn-$NH_2$], $^{14}$Leu,$^{25}$Phe exendin-4 [His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-$NH_2$], $^{14}$Leu,$^{25}$Phe exendin-4 (1-28) amide [His Gly Glu Gly Thr Phe Thr Ser Asp Leu Ser Lys Gln Leu Glu Glu Glu Ala Val Arg Leu Phe Ile Glu Phe Leu Lys Asn-$NH_2$], and $^{14}$Leu,$^{22}$Ala,$^{25}$Phe exendin-4 (1-28) amide [His Gly Glu Gly Thr Phe Thr Ser Asp Leu Ser Lys Gln Leu Glu Glu Glu Ala Val Arg Leu Ala Ile Glu Phe Leu Lys Asn-$NH_2$], and those described in International Application No. PCT/US98/16387, filed Aug. 6, 1998, entitled, "Novel Exendin Agonist Compounds," including compounds of the formula (I):

$Xaa_1$ $Xaa_2$ $Xaa_3$ Gly Thr $Xaa_4$ $Xaa_5$ $Xaa_6$ $Xaa_7$ $Xaa_8$
Ser Lys Gln $Xaa_9$ Glu Glu Glu Ala Val Arg Leu
$Xaa_{10}$ $Xaa_{11}$ $Xaa_{12}$ $Xaa_{13}$ Leu Lys Asn Gly Gly $Xaa_{14}$
Ser Ser Gly Ala $Xaa_{15}$ $Xaa_{16}$ $Xaa_{17}$ $Xaa_{18}$-Z wherein $Xaa_1$ is His, Arg or Tyr; $Xaa_2$ is Ser, Gly, Ala or Thr; $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —$NH_2$; with the proviso that the compound is not exendin-3 or exendin-4.

With reference to formula (I), in one embodiment N-alkyl groups for N-alkylglycine, N-alkylpentylglycine and N-alkylalanine include lower alkyl groups of 1 to about 6 carbon atoms, and of 1 to 4 carbon atoms.

In one embodiment exendin compounds of formula (I) include those wherein $Xaa_1$ is His or Tyr. In one embodiment, $Xaa_1$ is His.

In one embodiment are those compounds of formula (I) wherein $Xaa_2$ is Gly.

In one embodiment are those compounds of formula (I) wherein $Xaa_9$ is Leu, pentylglycine, or Met.

In one embodiment compounds of formula (I) include those wherein $Xaa_{13}$ is Trp or Phe.

Also in one embodiment are compounds of formula (I) where $Xaa_4$ is Phe or naphthylalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. In one embodiment N-alkylalanine has a N-alkyl group of 1 to about 6 carbon atoms.

According to one embodiment, compounds of formula (I) include those where $Xaa_{15}$, $Xaa_{16}$ and $Xaa_{17}$ are the same amino acid reside.

In one embodiment are compounds of formula (I) wherein $Xaa_{18}$ is Ser or Tyr, and in one embodiment Ser.

According to one embodiment are compounds of formula (I) wherein $Xaa_1$ is His or Tyr, and in one embodiment His; $Xaa_2$ is Gly; $Xaa_4$ is Phe or naphthylalanine; $Xaa_9$ is Leu, pentylglycine or Met; $Xaa_{10}$ is Phe or naphthylalanine; $Xaa_{11}$ is Ile or Val; $Xaa_{14}$, $Xaa_{15}$, $Xaa_{16}$ and $Xaa_{17}$ are independently selected from Pro, homoproline, thioproline or N-alkylalanine; and $Xaa_{18}$ is Ser or Tyr, and in one embodiment Ser. In one embodiment Z is $-NH_2$.

According to one embodiment, especially useful compounds include those of formula (I) wherein: $Xaa_1$ is His or Arg; $Xaa_2$ is Gly; $Xaa_3$ is Asp or Glu; $Xaa_4$ is Phe or napthylalanine; $Xaa_5$ is Thr or Ser; $Xaa_6$ is Ser or Thr; $Xaa_7$ is Asp or Glu; $Xaa_8$ is Leu or pentylglycine; $Xaa_9$ is Leu or pentylglycine; $Xaa_{10}$ is Phe or naphthylalanine; $Xaa_{11}$ is Ile, Val or t-butyltylglycine; $Xaa_{12}$ is Glu or Asp; $Xaa_{13}$ is Trp or Phe; $Xaa_{14}$, $Xaa_{15}$, $Xaa_{16}$, and $Xaa_{17}$ are independently Pro, homoproline, thioproline, or N-methylalanine; $Xaa_{18}$ is Ser or Tyr: and Z is $-OH$ or $-NH_2$; with the proviso that the compound does not have the formula of either exendin-3 or exendin-4. In one embodiment, Z is $-NH_2$.

According to one embodiment, provided are compounds of formula (I) where $Xaa_9$ is Leu, Ile, Val or pentylglycine, and in one embodiment Leu or pentylglycine, and $Xaa_{13}$ is Phe, Tyr or naphthylalanine, and in one embodiment Phe or naphthylalanine. These compounds will exhibit advantageous duration of action and be less subject to oxidative degradation, both in vitro and in vivo, as well as during synthesis of the compound. Suitable compounds of include compounds described in PCT international application PCT/US98/16387, filed Aug. 6, 1998, entitled "Novel Exendin Agonist Compounds" having the amino acid sequences of SEQ ID NOS:37-40 therein.

With reference to formula (I), preferably Z is $-NH_2$.

Exendin compounds also include compounds of the formula (II):

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein: $Xaa_1$ is His, Arg or Tyr; $Xaa_2$ is Ser, Gly, Ala or Thr; $Xaa_3$ is Ala, Asp or Glu; $Xaa_5$ is Ala or Thr; $Xaa_6$ is Ala, Phe, Tyr or naphthylalanine; $Xaa_7$ is Thr or Ser; $Xaa_8$ is Ala, Ser or Thr; $Xaa_9$ is Asp or Glu; $Xaa_{10}$ is Ala, Leu, Ile, Val, pentylglycine or Met; $Xaa_{11}$ is Ala or Ser; $Xaa_{12}$ is Ala or Lys; $Xaa_{13}$ is Ala or Gln; $Xaa_{14}$ is Ala, Leu, Ile, pentylglycine, Val or Met; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Ala, Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $Xaa_{27}$ is Ala or Lys; $Xaa_{28}$ is Ala or Asn; $Z_1$, is $-OH$, $-NH_2$, Gly-$Z_2$, Gly Gly-$Z_2$, Gly Gly $Xaa_{31}$-$Z_2$, Gly Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$ or Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is $-OH$ or $-NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

With reference to formula (II), in one embodiment N-alkyl groups for N-alkylglycine, N-alkylpentylglycine and N-alkylalanine include lower alkyl groups preferably of 1 to about 6 carbon atoms, and in one embodiment of 1 to 4 carbon atoms.

In one embodiment exendin compounds of formula (II) include those wherein $Xaa_1$ is His or Tyr. In one embodiment $Xaa_1$ is His.

In one embodiment are those compounds of formula (II) wherein $Xaa_2$ is Gly.

In one embodiment are those compounds of formula (II) wherein $Xaa_{14}$ is Leu, pentylglycine or Met.

In one embodiment compounds of formula (II) are those wherein $Xaa_{25}$ is Trp or Phe.

In one embodiment compounds of formula (II) are those where $Xaa_6$ is Phe or naphthylalanine; $Xaa_{22}$ is Phe or naphthylalanine and $Xaa_{23}$ is Ile or Val.

In one embodiment are compounds of formula (II) wherein $Xaa_{31}$, $Xaa_{36}$, $Xaa_{37}$ and $Xaa_{38}$ are independently selected from Pro, homoproline, thioproline and N-alkylalanine.

With reference to formula (II), in some embodiments $Z_1$ is $-NH_2$.

With reference to formula (II), in some embodiments $Z_2$ is $-NH_2$.

According to one aspect, useful are compounds of formula (II) wherein $Xaa_1$ is His or Tyr, and in one embodiment His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. In one embodiment $Z_1$ is $-NH_2$.

According to one embodiment, especially useful compounds include those of formula (II) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or naphthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is $-OH$, $-NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being $-OH$ or $-NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Suitable compounds of include compounds described in PCT international application PCT/US98/16387, filed Aug. 6, 1998, entitled "Novel Exendin Agonist Compounds" having the amino acid sequences of SEQ ID NOS: 40-61 therein.

According to one embodiment, provided are compounds of formula (II) where $Xaa_{14}$ is Leu, Ile, Val or pentylglycine, and in one embodiment Leu or pentylglycine, and $Xaa_{25}$ is Phe, Tyr or naphthylalanine, and in one embodiment Phe or naphthylalanine. These compounds will be less susceptive to oxidative degradation, both in vitro and in vivo, as well as during synthesis of the compound. Especially useful compounds include those set forth in PCT international application PCT/US98/24210, filed Nov. 13, 1998, entitled "Novel Exendin Agonist Compounds" identified therein as compounds 2-23.

Exendin compounds also include compounds of the formula (III):

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein wherein: $Xaa_1$ is His, Arg, Tyr, Ala, Norval, Val, or Norleu; $Xaa_2$ is Ser, Gly, Ala or Thr; $Xaa_3$ is Ala, Asp or Glu; $Xaa_4$ is Ala, Norval, Val, Norleu or Gly; $Xaa_5$ is Ala or Thr; $Xaa_6$ is Ala, Phe, Tyr or naphthylalanine; $Xaa_7$ is Thr or Ser; $Xaa_8$ is Ala, Ser or Thr; $Xaa_9$ is Ala, Norval, Val, Norleu, Asp or Glu; $Xaa_{10}$ is Ala, Leu, Ile, Val, pentylglycine or Met; $Xaa_{11}$ is Ala or Ser; $Xaa_{12}$ is Ala or Lys; $Xaa_{13}$ is Ala or Gln; $Xaa_{14}$ is Ala, Leu, Ile, pentylglycine, Val or Met; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $Xaa_{27}$ is Ala or Lys; $Xaa_{28}$ is Ala or Asn; $Z_1$ is —OH, $NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; wherein $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; $Xaa_{39}$ is Ser, Thr, Lys or Ala; and $Z_2$ is —OH or —$NH_2$; provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

In another aspect, Z, e.g., Z1 or Z2, is one or more additional amino acids that do not change the function of the Exendin as described herein with an —OH or NH2 at the carboxy terminus. In one embodiment additional amino acids are between 2 and 10 additional amino acids, between 3 and 7 additional amino acids, and about 5 additional amino acids.

In another embodiment, ICs include GLP-1 peptides. By way of non-limiting examples, a GLP-1 peptide includes GLP-1 (1-37), GLP-1 (1-36) amide, GLP-1 (7-37), GLP-1 (7-36) amide (known in the art as "GLP-1"), and GLP-1(9-36). Other exemplary GLP-1 peptides include GLP-1 agonists described in WO 03/084563, incorporated herein by reference in its entirety. In one embodiment, a GLP-1 peptide used in the methods of the present invention is a long-acting GLP-1 analog. A long acting analog refers to any GLP-1 peptide that has a longer in vivo half-life than GLP-1. Such long-acting GLP-1 analogs are known in the art and described herein.

An IC also includes any biologically active analogs, including variants and derivatives, of GLP-1 peptides. A biologically active GLP-1 analog, including a variant or derivative thereof, can possess GLP-1 biological activity that is more potent, less potent or equally potent as compared to the biological activity of a native GLP-1. Biologically active GLP-1 analogs also include those molecules that can exhibit GLP-1 activity upon cleavage, translation, or any other processing that occurs upon administration of the GLP-1 analog.

In an embodiment, a GLP-1 analog includes any peptides that are formed by conservative amino acid substitution of a GLP-1 peptide. For example, it is well known in the art that one or more amino acids in a sequence, such as an amino acid sequence for GLP-1, can be substituted with other amino acid(s), the charge and polarity of which are similar to that of the native amino acid. Hydropathic index of amino acids can be considered when making amino acid changes. The importance of the hydropathic amino acid index in conferring interactive biological function on a protein is generally understood in the art (Kyte and Doolittle, *J. Mol. Biol.* 157:105-132 (1982)). It is also understood in the art that the conservative substitution of amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. In making such changes, the substitution of amino acids whose hydrophilicity values are within ±2 is in one embodiment, those that are within ±1 are particularly useful, and those within ±0.5 are even more particularly useful.

Due to the degeneracy of the genetic code, different nucleotide codons can encode a particular amino acid. Accordingly, the present invention contemplates that a nucleic acid molecule encoding a GLP-1 analog can have any codon usage that encodes a GLP-1 analog. A host cell often exhibits a preferred pattern of codon usage. In a one embodiment, the codon usage of a nucleotide sequence encoding a GLP-1 reflects a preferred codon usage for a host in which the GLP-1 analog will be used.

In another embodiment, a GLP-1 analog has an amino acid sequence that has one or more amino acid substitutions, additions or deletions as compared with a GLP-1 peptide, preferably GLP-1. In one embodiment, a GLP-1 analog has an amino acid sequence that has about 30 or less, 25 or less, 20 or less, 15 or less, 10 or less, 5 or less, 4 or less, 3 or less, 2 or less, or 1 or less substitutions, additions, or deletions as compared to a GLP-1 peptide. Various GLP-1 analogs are generally known in the art and are available to the skilled artisan.

In another embodiment, a GLP-1 analog has at least 60%, at least 70%, at least 80%, at least 90% or at least 95% sequence identity with a naturally occurring GLP-1. Identity, as is well understood in the art, is a relationship between two or more polypeptide sequences or two or more polynucleotide sequences, as determined by comparing the sequences. In the art, identity also means the degree of sequence relatedness between polypeptide or polynucleotide sequences, as determined by the match between strings of such sequences. Identity can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math,* 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology,* 12: 76-80 (1994); Birren, et al., *Genome Analysis,* 1: 543-559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.,* 215:403-410 (1990)). The well-known Smith Waterman algorithm can also be used to determine identity.

An IC includes GLP-1 agonists and exendin agonists. The term "agonist" includes analogs. More particularly, as used herein, an "analog" is defined as a molecule having one or more amino acid substitutions, deletions, inversions, or additions compared with a native peptide such as a GLP-1 or exendin. The term "agonist" also includes derivatives. A "derivative" is defined as a molecule having the amino acid sequence of a native peptide or of an analog of the native peptide, but additionally having a chemical modification of one or more of its amino acid side groups, alpha-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine .epsilon.-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is C1-C4 alkyl. Furthermore, one or more side groups, or terminal groups, may be protected by protective groups known to the ordinarily-skilled protein chemist. The alpha-carbon of an amino acid may be mono- or dimethylated.

GLP-1 analogs known in the art include, for example, GLP-1(7-34) and GLP-1(7-35), Gln$^9$-GLP-1(7-37), D-Gln$^9$-GLP-1(7-37), Thr$^{16}$-Lys$^{18}$-GLP-1(7-37), and Lys$^{18}$-GLP-1(7-37). In other embodiments GLP-1 analogs include: Gly$^8$-GLP-1 (7-36)NH$_2$, Gln$^9$-GLP-1 (7-37), D-Gln$^9$-GLP-1 (7-37), acetyl-Lys$^9$-GLP-1(7-37), Thr$^9$-GLP-1(7-37), D-Thr$^9$-GLP-1 (7-37), Asn$^9$-GLP-1 (7-37), D-Asn$^9$-GLP-1 (7-37), Ser$^{22}$-Arg$^{23}$-Arg$^{24}$-Gln$^{26}$-GLP-1(7-37), Thr$^{16}$-Lys$^{18}$-GLP-1(7-37), Lys$^{18}$-GLP-1(7-37), Arg$^{23}$-GLP-1(7-37), Arg$^{24}$-GLP-1(7-37), and the like (see, e.g., WO 91/11457).

Other GLP-1 analogs are disclosed in U.S. Pat. No. 5,545, 618, which is incorporated herein by reference. In one embodiment is a group of GLP-1 analogs and derivatives include those disclosed in U.S. Pat. No. 6,747,006, which is herein incorporated by reference in its entirety. The use in the present invention of a molecule described in U.S. Pat. No. 5,188,666, which is expressly incorporated by reference, is also contemplated. Another group of molecules for use in the present invention includes compounds described in U.S. Pat. No. 5,512,549, which is expressly incorporated herein by reference.

In one embodiment is a group of active compounds for use in the present invention is disclosed in WO 91/11457, and consists essentially of GLP-1(7-34), GLP-1(7-35), GLP-1(7-36), or GLP-1(7-37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36; (b) substitution of an oxidation-resistant amino acid for tryptophan at position 31; (c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26;

(d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, (see, e.g. Mentlein, R., et al., *Eur. J. Biochem.*, 214:829-835 (1993)), administration of GLP-1 analogs and derivatives that are protected from the activity of DPP IV is useful, and the administration of Gly$^8$-GLP-1(7-36)NH$_2$, Val$^8$-GLP-1(7-37)OH, alpha-methyl-Ala$^8$-GLP-1 (7-36)NH$_2$, and Gly$^8$-Gln$^{21}$-GLP-1(7-37)OH, or pharmaceutically-acceptable salts thereof, may be even more useful. Alternatively or additionally, a DPPIV inhibitor may also be administered.

An IC can be obtained from any source. In one embodiment, an IC can be obtained from an organism, such as a mouse, a rat, a lizard, or a human. It is also contemplated herein that an IC can be obtained by any method or combination of methods known to the skilled artisan. In an illustrative embodiment, an IC can be isolated by collection of a secretion, by extraction, by purification, or by any combination such of methods. In another embodiment, an IC can be identified and purified by the use of monoclonal, polyclonal, or any combination of antibodies. Antibodies such as ABGA1178 detect intact, unspliced GLP-1 (1-37) or N-terminally truncated GLP-1 (7-37) or GLP-1. In addition, other antibodies detect at the very end of the C-terminus of the precursor molecule (See e.g. Osrkov et al., *J. Clin. Invest.* 87: 415-423 (1991)).

In another embodiment, an IC can be obtained by any recombinant means. A recombinant IC includes any molecule that is, or results, however indirectly, from human manipulation of a nucleic or amino acid molecule. In one embodiment, a recombinant molecule is a recombinant human peptide.

In another embodiment, the use of DPP IV inhibitors to decrease or eliminate the inactivation of endogenous or exogenous GIP or GLP-1, or analog or agonist is also contemplated. DPP IV inhibitors can be administered alone or in combination with a IC. As such, it is contemplated that active ICs may be increased by the inhibition of DPP IV. Inhibitors of DPP IV are known to the skilled artisan and include, by way of non-limiting example, 2-cyanopyrrolidines. See e.g. Fukushima, H., et al., *Bioorg. Med. Chem. Lett.* 14(22): 6053-6061 (2004). Non-limiting exemplary DPP IV inhibitors include valine-pyrrolidide (Marguet, D., et al., *Proc. Natl. Acad. Sci. USA* 97(12): 6874-6879 (2000)), isoleucine thiazolidide (Pederson, R. A., et al., *Diabetes* 47: 1253-1258 (1998), and NVP-DPP728 (Balkan, B., et al., *Diabetologia* 42(11):1324-1331 (1999)). DPP IV inhibitors including ketopyrrolidines and ketoazetidines have been discussed in the literature (Ferraris, D., et al., *Bioorg. Med. Chem. Lett.* 14(22): 5579-5583 (2004)). Metformin and pioglitazone have been proposed to reduce DPP IV activity in vivo. (Kenhard, J. M., et al., *Biochem. Biophys. Res. Commun.* 324(1):92-97 (2004). Literature reports further describe optimization of a proline derived homophenylalanine 3 to produce a potent DPP IV inhibitor. Edmondson, S. D., et al., Bioorg. Med. Chem. Lett. 14(20): 5151-5155 (2004).

C. Exemplary Amylinomimetic Compounds

Amylin agonists for use in the methods include amylin agonist analogs, examples of which are described in U.S. Pat. No. 5,686,411; U.S. Pat. No. 6,610,824; U.S. Pat. No. 5,998,367; U.S. Pat. No. 6,087,334; and international application, PCT/US2005/004631, all of which are incorporated herein by reference. In certain embodiments, methods of the invention amylin agonists do not include AFP-6 (intermedin) and novel compounds described in U.S. provisional application No. 60/617,468, filed Oct. 8, 2004 and international application publication WO 2006/042242. In certain embodiments, the amylin agonists do not include calcitonin. In certain embodiments, the amylin agonists do not include salmon calcitonin. In other embodiments, the amylin agonists do not include CGRP. In still other embodiments, amylin agonists do not include analogs of CGRP or calcitonin. Accordingly, it is contemplated that methods of the invention may include a proviso that excludes CGRP or AFP-6 or calcitonin, or their analogs.

By "amylin" is meant the human peptide hormone referred to as amylin and secreted from the beta cells of the pancreas, and species variations thereof, as described in U.S. Pat. No. 5,234,906, issued Aug. 10, 1993, for "Hyperglycemic Compositions," the contents of which are hereby incorporated by reference. More particularly, amylin is a 37-amino acid polypeptide hormone normally co-secreted with insulin by pancreatic beta cells in response to nutrient intake (see, e.g. Koda et al., *Lancet* 339:1179-1180, 1992). In this sense, "amylin," "wild-type amylin," and "native amylin," i.e., unmodified amylin, are used interchangeably. Amylin is also sometimes referred to as "IAPP."

By "agonist" is meant a compound which elicits a biological activity of amylin, preferably having a potency better than amylin, or within five orders of magnitude (plus or minus) of potency compared to amylin, in another embodiment 4, 3, 2, or 1 order of magnitude, when evaluated by art-known measures such as receptor binding/competition studies as described herein. Agonists include peptide as well as non-peptide compounds.

In one embodiment, the term refers to a compound which elicits a biological effect similar to that of native amylin, for example a compound (1) having activity in a food intake, gastric emptying, pancreatic secretion, or weight loss assay (international application PCT/US2005/004631, incorporated by reference) similar to native human reference peptide, and/or (2) which binds specifically in a reference receptor assay or in a competitive binding assay with amylin. Exemplary agonists will bind in such assays with an affinity of less than 1 µM, and even further with an affinity of less than 1-5 nM, 500, 100, 50, or 5 pM. Such agonists may comprise a polypeptide comprising an active fragment of amylin or a small chemical molecule. It is, however, contemplated that in certain embodiments of the invention, salmon calcitonin, calcitonin, CGRP, AFP-6, and/or their respective analogs may be in some alternatives excluded from the scope of amylin agonists for use in the methods of the present invention.

Agonists include amylin analogs and amylin derivatives. By "analog" is meant a peptide whose sequence is derived from that of amylin including insertions, substitutions, extensions, and/or deletions, having at least some amino acid identity to amylin or region of an amylin peptide. Analogs may have at least 50 or 55% amino acid sequence identity with a native amylin, or at least 70%, 80%, 90%, or 95% amino acid sequence identity with a native amylin. In one embodiment, such analogs may comprise conservative or non-conservative amino acid substitutions (including non-natural amino acids and L and D forms). Amylin agonist analogs are analogs as herein described and function as an amylin agonist.

A "derivative" is defined as a molecule having the amino acid sequence of a native amylin or analog, but additionally having a chemical modification of one or more of its amino acid side groups, alpha-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled synthetic chemist. The alpha-carbon of an amino acid may be mono- or dimethylated.

Human amylin has the following amino acid sequence: Lys-Cys-Asn-Thr-Ala-Thr-Cys-Ala-Thr-Gln Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO: 1), although the use of amylins from any species is contemplated. Amylin agonists contemplated in the use of the invention include those described in U.S. Pat. Nos. 5,686,411, 6,114,304, and 6,410,511, which are herein incorporated by reference in their entirety. Such compounds include those having amylinomimetic-formula I, A1-X-Asn-Thr-Ala-Thr-Y-Ala-Thr-Gln-Arg-Leu-B1-Asn-Phe-Leu-C1-D1-E1-F1-G1-Asn-H1-Gly-I1-J1-Leu-K1-L1-Thr-M1-Val-Gly-Ser-Asn-Thr-Tyr (SEQ ID NO:2)

wherein $A_1$ is Lys, Ala, Ser or hydrogen;
$B_1$ is Ala, Ser or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ala or Pro;
$J_1$ is Ile, Val, Ala or Leu;
$K_1$ is Ser, Pro, Leu, Ile or Thr;
$L_1$ is Ser, Pro or Thr;
$M_1$ is Asn, Asp, or Gln;
X and Y are independently selected amino acid residues having side chains which are chemically bonded to each other to form an intramolecular linkage.

The C-terminal portion can be amino, alkylamino, dialkylamino, cycloalkylamino, arylamino, aralkylamino, alkyloxy, aryloxy, aralkyloxy or carboxyl.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. In one embodiment alkyl chains include lower alkyl groups having from about 1 to about 6 carbon atoms.

An additional aspect of the present invention is directed to agonist analogues of amylinomimetic-formula I SEQ ID NO:2 which are not bridged, and wherein X and Y are independently selected from Ala, Ser, Cys, Val, Leu and Ile or alkyl, aryl, or aralkyl esters and ethers of Ser or Cys.

Exemplary compounds include, but are not limited to des-$^1$Lys-h-amylin, $^{28}$Pro-h-amylin, $^{25,28,29}$Pro-h-amylin, $^{18}$Arg$^{25,28}$Pro-h-amylin, and des-$^1$Lys$^{18}$Arg$^{25,28}$Pro-h-amylin, which all show amylin activity in vivo in treated test animals. In addition to having activities characteristic of amylin, certain of the compounds of the invention have also been found to possess more desirable solubility and stability characteristics when compared to human amylin. Examples of these compounds include $^{25}$Pro$^{26}$Val$^{28,29}$Pro-h-amylin, $^{25,28,29}$Pro-h-amylin, and $^{18}$Arg$^{25,28}$Pro-h-amylin.

Other compounds include $^{18}$Arg$^{25,28}$Pro-h-amylin, des-$^1$Lys$^{18}$Arg$^{25,28}$Pro-h-amylin, $^{18}$Arg$^{25,28,29}$Pro-h-amylin, des-$^1$Lys$^{18}$Arg$^{25,28,29}$Pro-h-amylin, $^{25,28,29}$Pro-h-amylin, des-$^1$Lys$^{25,23,29}$Pro-h-amylin, $^{25}$Pro$^{26}$Val$^{28,29}$Pro-h-amylin, $^{23}$Leu$^{25}$Pro$^{26}$Val$^{29,29}$Pro-h-amylin, $^{23}$Leu$^{25}$Pro$^{26}$Val$^{28}$Pro-h-amylin, des-$^1$Lys$^{23}$Leu$^{25}$Pro$^{26}$Val$^{28}$Pro-h-amylin, $^{18}$Arg$^{23}$Leu$^{25}$Pro$^{26}$Val.$^{28}$Pro-h-amylin, $^{18}$Arg$^{23}$Leu$^{25,28,29}$Pro-h-amylin, $^{18}$Arg$^{23}$Leu$^{25,28}$Pro-h-amylin, $^{17}$Ile$^{23}$Leu$^{25,28,29}$Pro-h-amylin, $^{17}$Ile$^{25,28,29}$Pro-h-amylin, des-$^1$Lys$^{17}$Ile$^{23}$Leu$^{25,28,29}$Pro-h-amylin, $^{17}$Ile$^{18}$Arg$^{23}$Leu-h-amylin, $^{17}$Ile$^{18}$Arg$^{23}$Leu$^{26}$Val$^{29}$Pro-h-amylin, $^{17}$Ile$^{18}$Arg$^{23}$Leu$^{25}$Pro$^{26}$Val$^{28,29}$Pro-h-amylin, $^{13}$Thr$^{21}$His$^{23}$Leu$^{26}$Ala$^{28}$Leu$^{29}$Pro$^{31}$Asp-h-amylin, $^{13}$Thr$^{21}$His$^{23}$Leu$^{26}$Ala$^{29}$Pro$^{31}$Asp-h-amylin, des-$^1$Lys$^{13}$Thr$^{21}$His$^{23}$Leu$^{26}$Ala$^{2}$Pro$^{31}$Asp-h-amylin, $^{13}$Thr$^{18}$Arg$^{21}$His$^{23}$Leu$^{26}$Ala$^{29}$Pro$^{3}$Asp-h-amylin, $^{13}$Thr$^{18}$Arg$^{21}$His$^{23}$Leu$^{28,29}$Pro$^{31}$Asp-h-amylin, and $^{13}$Thr$^{18}$Arg$^{21}$His$^{23}$Leu$^{25}$Pro$^{26}$Ala$^{28,29}$Pro$^{31}$Asp-h-amylin.

Useful amylin agonists also include analogs of amylinomimetic-formula II, X1-Xaa1-X2-Xaa2-X3-Xaa3-X4-Xaa4-X5-Xaa5-X6 (SEQ ID NO:3) wherein $X_1$ is Lys, Arg or absent;
$X_2$ is Xaa$_6$ Xaa$_7$ Xaa$_8$ Xaa$_9$ (SEQ. ID. NO: 4) or Z-Xaa$_{10}$ Ser Thr, provided that if $X_2$ is Z-Xaa$_{10}$ SerThr, then $X_1$ and Xaa$_1$ are both absent;
$X_3$ is AlaThr, AlaSer, SerMet, GluThr or ValThr;
$X_4$ is ArgLeuAla, HisLeuAla, ArgIleAla, LysIleAla, ArgMetAla, HisMetAla, LysMetAla or ArgLeuThr;
$X_5$ is PheLeu, PheIle, PheMet, TyrLeu, TyrIle, TyrMet, TrpMet, TrpIle or TrpMet;
$X_6$ is ArgSerSerGlyTyr (SEQ ID NO:5), LysSerSerGlyTyr (SEQ ID NO:6), HisSerSerGlyTyr (SEQ ID NO:7), ProSerSerGlyTyr (SEQ ID NO:8), ArgSerArgGlyTyr (SEQ ID NO:9), ArgThrSerGlyTyr (SEQ ID NO: 10), ArgAlaSerGlyTyr (SEQ ID NO: 11), AlaSerSerGlyTyr (SEQ ID NO: 12), ArgSerAlaGlyTyr (SEQ ID NO: 13), HisSerAlaGlyTyr (SEQ ID NO: 14), ArgSerGlyTyr (SEQ ID NO: 15), ArgSer, LysSer, HisSer, ArgThr, ProSer or Arg;
Xaa$_1$ is Cys or absent;
Xaa$_2$ is Cys or Ala;
Xaa$_3$ is Gln, Ala or Asn;
Xaa$_4$ is Asn, Ala or Gln;
Xaa$_5$ is Val, Ala, Ile, Met, Leu, PentylGly, or t-butylGly;
Xaa$_6$ is Asn, Gln or Asp;
Xaa$_7$ is Thr, Ser, Met, Val, Leu or Ile;
Xaa$_8$ is Ala or Val;
Xaa$_9$ is Thr or Ser;
Xaa$_{10}$ is Leu, Val, Met or Ile; and
Z is an alkanoyl group of about 1 to about 8 carbon atoms or absent, and pharmaceutically acceptable salts thereof.

Useful amylin agonists may include analogs of comprising an amino acid sequence of amylinomimetic-formula III, Xaa1-X-Xaa3-Xaa4-Xaa5-Xaa6-Y-Xaa8-Xaa9-Xaa10-Xaa11-Xaa12-Xaa13-Xaa14-Xaa15-Xaa16-Xaa17-Xaa18-Xaa19-Xaa20-Xaa21-Xaa22-Xaa23-Xaa24-Xaa25-Xaa26-Xaa27-Xaa28-Xaa29-Xaa30-Xaa31-Xaa32 (SEQ ID NO: 16) wherein:
Xaa1 is A, C, hC (homoCys), D, E, F, I, L, K, hK (homoLys), R, hR (homoArg), S, Hse(homoSer), T, G, Q, N, M, Y, W, P, Hyp(hydroxyPro), H, V or absent;
Xaa3 is A, D, E, N, Q, G, V, R, K, hK, hR, H, I, L, M, or absent;
Xaa4 is A, I, L, S, Hse, T, V, M, or absent;
Xaa5 is A, S, T, Hse, Y, V, I, L, or M;
Xaa6 is T, A, S, Hse, Y, V, I, L, or M;
Xaa8 is A, V, I, L, F, or M;
Xaa9 is L, T, S, Hse, V, I, or M;
Xaa10 is G, H, Q, K, R, N, hK, or hR;
Xaa11 is K, R, Q, N, hK, hR, or H;
Xaa12 is L, I, V, F, M, W, or Y;
Xaa13 is A, F, Y, N, Q, S, Hse, or T;
Xaa14 is A, D, E, G, N, K, Q, R, H, hR, or hK;
Xaa15 is A, D, E, F, L, S, Y, I, V, or M;
Xaa16 is L, F, M, V, Y, or I;
Xaa17 is H, Q, N, S, Hse, T, or V;
Xaa18 is K, hK, R, hR, H, u (Cit), or n (Orn);
Xaa19 is F, L, S, Hse, V, I, T, or absent;
Xaa20 is H, R, K, hR, hK, N, Q, or absent;
Xaa21 is T, S, Hse, V, I, L, Q, N, or absent;
Xaa22 is F, L, M, V, Y, or I;
Xaa23 is P or Hyp;
Xaa24 is P, Hyp, R, K, hR, hK, or H;
Xaa25 is T, S, Hse, V, I, L, F, or Y;
Xaa26 is N, Q, D, or E;
Xaa27 is T, V, S, F, I, or L;
Xaa28 is G or A;
Xaa29 is S, Hse, T, V, I, L, or Y;
Xaa30 is E, G, K, N, D, R, hR, hK, H, or Q;
Xaa31 is A, T, S, Hse, V, I, L, F, or Y; and
Xaa32 is F, P, Y, Hse, S, T, or Hyp;
wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond. Alkyl chains may include lower alkyl groups having from about 1 to about 6 carbon atoms. In certain embodiments, the intramolecular linkage may be a disulfide, amide, imine, amine, alkyl or alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp. Other embodiments are described in international application, PCT/US2005/004631, filed on Feb. 11, 2005, and incorporated by reference.

Exemplary compounds described with reference to human amylin (SEQ ID NO:1) and salmon calcitonin (sCT) CSNLSTCVLGKLSQELHKLQTYPRTNTGSGTP (SEQ ID NO: 17) with modifications at the position(s) indicated include, (1-7 hAmy)($^{18}$Arg-8-27 sCT)(33-37 hAmy); (1-7 hAmy) ($^{11,18}$Arg$^{22}$Leu-8-27sCT)(33-37 hAmy); (1-7 hAmy) ($^{11,18}$Arg$^{24}$Pro-8-27 sCT)(33-37 hAmy); (1-7 hAmy) ($^{11,18}$Arg-8-24sCT)(30-37 hAmy); (1-7 hAmy)(11Arg, 18Arg-8-21 sCT)(27-37 rAmy); (⁸Val⁹Leu¹⁰Gly-1-15hAmy)(¹⁸Arg-16-27sCT)(31-37hAmy); (1Ala-1-7 hAmy)(¹¹,¹⁸Arg-8-27 sCT)(33-37 hAmy); (³Ala-1-7 hAmy)(¹¹,¹⁸Arg-8-27 sCT)(33-37 hAmy); (⁴Ala-1-7 hAmy)(¹¹,¹⁸Arg-8-27 sCT)(33-37 hAmy); (⁶Ala-1-7 hAmy)(¹¹,¹⁸Arg-8-27 sCT)(33-37 hAmy); (²Ala¹¹,¹⁸Arg-1-27 sCT)(33-37 hAmy); (Isocap-⁷Ala¹¹,¹⁸Arg-5-27 sCT)(33-37 hAmy); (⁴Ala¹¹,¹⁸Arg-1-27 sCT)(33-37 hAmy); (⁵Ala¹¹,¹⁸Arg-1-27 sCT)(33-37 hAmy); (⁶Ala¹¹,¹⁸Arg-1-27 sCT)(33-37 hAmy); (1-7 hAmy)(¹¹Arg-8-27 sCT)(33-37 hAmy); (¹³Ser¹⁴Gln¹⁵Glu-1-16 hAmy)(¹⁷Arg³⁰Asn³²Tyr-17-32 sCT); (³Ala¹¹,¹⁸Arg-1-27 sCT)(33-37 hAmy); (Acetyl-²,⁷Agy¹¹,¹⁸Arg-1-27 sCT)(33-37 hAmy); (Acetyl-²,⁷Agy-1-7 hAmy)(¹¹,¹⁸Arg-8-27 sCT)(33-37 hAmy); (Isocap-⁷Ala¹⁰Aib¹¹Lys(For)¹⁷Aib¹⁸Lys(For)-5-27 sCT)(33-37 hAmy); (Isocap-⁷Ala¹⁰Aib¹¹Lys(For)¹⁷Aib¹⁸Lys(For)-5-24sCT)(30-37 hAmy); ((Isocap-⁷Ala¹⁰Aib¹¹Lys(For)¹⁷Aib¹⁸Lys(For)-5-22 sCT)(²⁸,²⁹Pro-28-37 hAmy); (Isocap-⁷Ala¹⁰Aib¹¹Lys(For)¹⁷Aib¹⁸Lys(For)-5-21 sCT)(²⁸,²⁹Pro-27-37 hAmy); (1-7 hAmy)(LLQQWQKLLQKLKQ (SEQ ID NO:20))(²⁸Pro²⁹Arg³²Thr-27-37 hAmy); (1-7 hAmy)(LLQQLQKLLQKLKQY (SEQ ID NO:21)(²⁸Pro²⁹Arg³²Thr-28-37 hAmy); (⁶Ser-1-7 hAmy)(¹¹,¹⁸Arg-8-27 sCT)(33-37 hAmy); (⁶Val-1-7 hAmy)(¹¹,¹⁸Arg-8-27 sCT)(33-37 hAmy); (1-7 hAmy)(¹¹,¹⁸Arg-8-18 sCT)(²⁸Pro²⁹Arg³²Thr-27-37 hAmy); (1-7 hAmy)(¹¹Arg-8-17 sCT)(²⁸Pro²⁹Arg³²Thr-27-37 hAmy); (1-7 hAmy)(¹¹Arg-8-16 sCT)(²⁷Tyr²⁸Pro²⁹Arg³²Thr-27-37 hAmy); (1-7 hAmy)(¹¹Arg-8-15sCT)(²⁷Tyr²⁸Pro²⁹Arg³²Thr-27-37 hAmy); (1-7 hAmy)(¹¹Arg-8-14 sCT)(²⁷Tyr²⁸Pro²⁹Arg³²Thr-27-37 hAmy); (1-7 hAmy)(¹¹,¹⁸Lys(For))-8-27 sCT)(33-37 hAmy); (⁶D-Thr-1-7 hAmy)(¹¹,¹⁸Arg)-8-27 sCT)(33-37 hAmy); (Acetyl-1-7 hAmy)(¹¹,¹⁸Lys(PEG5000-8-27 sCT)(33-37 hAmy); (Acetyl-¹Ala-1-7 hAmy)(¹¹Lys(PEG5000)¹⁸Arg-8-27 sCT)(33-37 hAmy); (Acetyl-¹Ala-1-7 hAmy)(¹¹Arg¹⁸Lys(PEG5000)-8-27 sCT)(33-37 hAmy); (1-7 hAmy)(¹¹,¹⁸Arg-8-21 sCT)(¹⁸-27 sCT)(33-37 hAmy); (1-7 hAmy)(¹¹,¹⁸Arg-8-21 sCT)(¹⁸Leu-18-27 sCT)(33-37 hAmy); (1-7hAmy)(8-27sCT)(33-37hAmy); (⁵Ser-1-7hAmy)(¹¹,¹⁸Arg-8-27sCT)(33-37hAmy); (1-12hAmy)(¹⁸Arg-13-27sCT)(33-37hAmy); (1-12hAmy)(¹⁸Arg-13-24sCT)(30-37hAmy); (⁵Ser¹⁵Glu¹⁸Arg-1-18hAmy)(19-24sCT)(30-37hAmy); (6Hse-1-7hAmy)(¹¹,¹⁸Arg-8-27sCT)(33-37hAmy); (⁶Ahb-1-7hAmy)(¹¹,¹⁸Arg-8-27sCT)(33-37hAmy); (6Ahp-1-7hAmy)(¹¹,¹⁸Arg-8-27sCT)(33-37hAmy); ⁶Thr(OPO₃H₂)-1-7hAmy)(¹¹,¹⁸Arg-8-27sCT)(33-37 hAmy); (⁷Ala¹¹,¹⁸Arg-5-27 sCT)(33-37 hAmy); (1-7 hAmy)(¹¹,¹⁸Orn-8-27 sCT)(33-37 hAmy); (1-7 hAmy)(¹¹,¹⁸Cit-8-27 sCT)(33-37 hAmy); (1-7 hAmy)(¹¹,¹⁸homoLys-8-27 sCT)(33-37 hAmy); (L-Octylglycine-1-7hAmy)(¹,¹⁸Arg-8-27sCT)(33-37hAmy); (N-3,6-dioxaoctanoyl-1-7-hAmy)(¹¹,¹⁸Arg-8-27sCT)(33-37hAmy); (cyclo (1-7)-¹Asp⁷Lys¹¹,¹⁸Arg-1-27sCT)(33-37 hAmy); (cyclo(2-7)-2Asp⁷Lys-1-7 hAmy)(¹¹,¹⁸Arg-8-27 sCT)(33-37 hAmy); (cyclo 2-7 hAmy)(¹¹,¹⁸Arg-8-27 sCT)(33-37 hAmy); (1-7hAmy)(¹¹,¹⁸Arg-8-27sCT)(33-37hAmy-9Anc); (1-7hAmy)(¹¹,¹⁸Arg-8-27sCT)(33-37hAmy-Loctylglycine); (N-isocaproyl-1-7-hAmy)(¹¹,¹⁸Arg-8-27sCT)(33-37hAmy); (1-7 hAmy)(¹¹,¹⁸homoArg-8-27 sCT)(33-37 hAmy); (¹Phe-1-7hAmy)(¹¹,¹⁸Arg-8-27sCT)(33-37hAmy); (1-7 hAmy)(¹¹,¹⁸Arg-8-24sCT)(³²Thr-30-37 hAmy); (1-7 hAmy)(¹¹,¹⁸Arg-8-27 sCt)(33-37 hAmylin); (¹⁵Glu¹⁸Arg-1-18hAmy)(19-24 sCT)(30-37hAmy); (¹³Ala¹⁴Asp¹⁵Phe-1-18hAmy)(19-23sCT)(30-37hAmy); and (2-18 hAmy)(19-23 sCT)(30-36 hAmy).

Other useful amylin agonists may include analogs of comprising an amino acid sequence of amylinomimetic-formula IV: Xaa1-Xaa2-Xaa3-Leu-Xaa4-Glu-Leu-Xaa5-Xaa6-Leu-Gln-Thr-Tyr-Pro-Arg-Thr-Asn-Xaa7-Z3[SEQ ID NO 22] wherein:

(a) Xaa1 is (i) a group having two amino acid residues selected from the group consisting of Leu-Leu, Val-Leu, Ile-Leu, tert-Leu-Leu, Nle-Leu, and Ala-Thr, and N-acylated derivatives thereof; or is (ii) the group Z1-Ser-Thr-Z2-Val-Leu [SEQ ID NO: 23] wherein Z1 is an amino acid residue selected from the group consisting of Leu, Val, Ile, tert-Leu, Nva, Abu, and Nle or an N-acylated derivative thereof or Z1 is an alkanoyl group; and Z2 is an amino acid residue selected from the group consisting of Ala, Ser, Cys, and Thr;

(b) Xaa2 is an amino acid residue selected from the group consisting Gly, Glu, Asn or Aib;

(c) Xaa3 is an amino acid residue selected from the group consisting of Arg, Orn, Lys, and epsilon-amidated derivatives thereof;

(d) Xaa4 is a group having two or more amino acid residues selected from the group consisting of Ser-Gln, Thr-Gln, Ala-Asn, and Thr-Asn;

(e) Xaa5 is an amino acid residue selected from the group consisting of His, Aib, Ile, Leu, and Val;

(f) Xaa6 is an amino acid residue selected from the group consisting of Arg, Orn, and Lys and epsilon-amidated derivates thereof;

(g) Xaa7 is a group having six amino acid residues selected from the group consisting of
(i) Thr-Gly-Ser-Asn-Thr-Tyr {SEQ ID NO: 24];
(ii) Thr-Gly-Ser-Gly-Thr-Pro {SEQ ID NO: 25];
(iii) Val-Gly-Ser-Asn-Thr-Tyr [SEQ ID NO: 26];
(iv) Val-Gly-Ser-Gly-Thr-Pro [SEQ ID NO: 27]; and
(h) Z3 is OH or NH2.

Peptides useful in the invention, like those above, can be in the acid or amide form.

Derivatives of the agonists and analogs are also included within the scope of this invention in which the stereochemistry of individual amino acids may be inverted from (L)/S to (D)/R at one or more specific sites. Also included within the scope of this invention are the agonists and analogs modified by glycosylation of Asn, Ser and/or Thr residues. Compounds useful in the methods of the invention may also be biologically active fragments of the peptides (native, agonist, analog, and derivative) herein described.

Agonist and analogs of amylin that contain less peptide character are included within the scope of this invention. Such peptide mimetics may include, for example, one or more of the following substitutions for —CO—NH— amide bonds: depsipeptides (—CO—O—), iminomethylenes (—CH₂—NH—), trans-alkenes (—CH=CH—), beta-enaminonitriles (—C(=CH—CN)—NH—), thioamides (—CS—NH—), thiomethylenes (—S—CH₂— or —CH₂—S—), methylenes (—CH₂—C₂—) and retro-amides (—NH—CO—).

Compounds of this invention form salts with various inorganic and organic acids and bases. Such salts include salts prepared with organic and inorganic acids, for example, HCl, HBr, H₂SO₄, H₃PO₄, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). Acetate, hydrochloride, and trifluoroacetate salts are useful.

Amylin agonists useful in the invention may also include fragments of amylin and its analogs as described above as well as those described in EP 289287, the contents of which are herein incorporated by reference. Amylin agonists analogs may also be compounds having at least 60, 65, 70, 75, 80, 85, 90, 95, or 99% amino acid sequence identity to SEQ ID NO:1, or any of the amylin analogs specifically described herein having amylin activity. Amylin agonists also include small molecules and non-peptide molecules, for example those based on small molecule chemistry.

"Amylin activity" as used herein may include the activities known in the art or as described herein, particularly of interest is a glucoregulatory activity. It is contemplated that in certain embodiments, amylin agonists, useful in certain methods of the invention, may not include AFP-6, calcitonins and/or calcitonin-gene-related peptides (CGRPs). For example, in certain embodiments, AFP-6, calcitonins and/or CGRPs may be excluded from the scope of amylin agonist in the treatment of the metabolic diseases and conditions herein. Similarly, in certain embodiments, amylin agonists, useful in methods of the invention, may not include their analogs.

Amylin agonist analogs also include insertions, deletions, extensions, truncations, and/or substitutions in at least one or more amino acid positions of human amylin or any of the amylin analogs specifically described herein. The number of amino acid insertions, deletions, or substitutions may be at least 5, 10, 15, 20, 25, or 30. Insertions, extensions, or substitutions may be with other natural amino acids, synthetic amino acids, peptidomimetics, or other chemical compounds.

In general, amylin agonists or amylin agonist analogs are recognized as referring to compounds which, by directly or indirectly interacting or binding with one or more receptors, mimics an action of amylin. They may also be referred to as amylinomimetics.

In one embodiment, the present invention is directed to the use of amylin or amylin agonists that bind to or act at an amylin and/or calcitonin receptor. It has been reported that the biological actions of amylin family peptide hormones are generally mediated via binding to two closely related type II G protein-coupled receptors (GPCRs), the calcitonin receptor (CTR) (of which there are multiple forms known in the art) and the calcitonin receptor like receptor (CRLR). Cloning and functional studies have shown that CGRP, calcitonin, adrenomedullin, and amylin interact with different combinations of CTR or the CRLR and the receptor activity modifying protein (RAMP). Many cells express multiple RAMPs. It is believed that co-expression of RAMPs and either the CTR or CRLR is required to generate functional receptors for calcitonin, CGRP, ADM, and amylin. The RAMP family comprises three members (RAMP1, -2, and -3), which share less then 30% sequence identity, but have a common topological organization. Co-expression of CRLR and RAMP1 leads to the formation of a receptor for CGRP. Co-expression of CRLR and RAMP2 leads to the formation of a receptor for ADM. Co-expression of CRLR and RAMP3 leads to the formation of a receptor for ADM and CGRP. Co-expression of hCTR2 and RAMP1 leads to the formation of a receptor for amylin and CGRP. Co-expression of hCTR2 and RAMP3 leads to the formation of a receptor for amylin.

Activity as amylin agonists and/or analogs can be confirmed and quantified by performing various screening assays, including the nucleus accumbens receptor binding assay, the soleus muscle assay, a gastric emptying assay, by the ability to induce hypocalcemia, by reducing postprandial hyperglycemia in mammals, or by beneficially effecting a marker or symptom of a metabolic disease and condition described herein. Methods of testing compounds for amylin activity are known in the art. Exemplary screening methods and assays for testing amylin agonists are described in U.S. Pat. Nos. 5,264,372 and 5,686,411, which are incorporated herein by reference.

The receptor binding assay is a competition assay that measures the ability of compounds to bind specifically to membrane-bound amylin receptors. A useful source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand, are analyzed by computer using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson and Rodbard, Anal. Biochem. 107:220-239 (1980).

Assays of biological activity of amylin agonists/analogs in the soleus muscle may be performed using previously described methods (Leighton, B. and Cooper, Nature, 335: 632-635 (1988); Cooper, et al., Proc. Natl. Acad. Sci. USA 85:7763-7766 (1988)), in which amylin agonist activity may be assessed by measuring the inhibition of insulin-stimulated glycogen synthesis. In brief, an exemplary method includes soleus muscle strips prepared from 12-h fasted male Wistar rats. The tendons of the muscles are ligated before attachment to stainless steel clips. Muscle strips are pre-incubated in Erlenmeyer flasks containing 3.5 ml Krebs-Ringer bicarbonate buffer, 7 mM N-1-hydroxyethyl-peperazine-N'-2-ethanesulphonic acid, pH 7.4, and 5.5 mM pyruvate. Flasks are sealed and gassed continuously with $O_2$ and $CO_2$ in the ratio 19:1 (v/v). After pre-incubation of muscles in this medium for 30 min at 37° C. in an oscillating water bath, the muscles strips are transferred to similar vials containing identical medium (except pyruvate) with added [U-$^{14}$C] glucose (0.5 µCi/ml) and insulin (100 µU/ml). The flasks are sealed and re-gassed for an initial 15 min in a 1-h incubation. At the end of the incubation period, muscles are blotted and rapidly frozen in liquid $N_2$. The concentration of lactate in the incubation medium can be determined spectrophotometrically and [U-$^{14}$C] glucose incorporation in glycogen measured.

Methods of measuring the rate of gastric emptying are disclosed in, for example, Young et al. In a phenol red method, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Amylin agonist compounds may exhibit activity in the receptor binding assay on the order of less than about 1 to 5 nM, preferably less than about 1 nM and in one embodiment less than about 50 pM. In the soleus muscle assay, amylin agonist compounds may show $EC_{50}$ values on the order of less than about 1 to 10 micromolar. In the gastric emptying assays, agonist compounds may show $ED_{50}$ values on the order of less than 100 µg/rat.

In one exemplary method of making the compounds, compounds of the invention may be prepared using standard solid-phase peptide synthesis techniques and preferably an automated or semiautomated peptide synthesizer. Typically, using such techniques, a alpha-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being useful herein. Other methods of synthesizing or expressing amylin and amylin agonists and purifying them are known to the skilled artisan.

D. Pharmaceutical Compositions of the Invention

IC or amylinomimetics may be formulated as pharmaceutical compositions for use in conjunction with the methods of the present invention. These compounds may be administered alone or in combination with pharmaceutically acceptable carriers or excipients, in either as single or multiple doses. The pharmaceutical compositions may be formulated with pharmaceutically acceptable excipients such as carriers, solvents, stabilizers, adjuvants, diluents, etc., depending upon the particular mode of administration and dosage form. Formulations can be made using conventional techniques such as those disclosed in Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2 S (1988). The pharmaceutical compositions should generally be formulated to achieve a physiologically compatible pH, and may range from a pH of about 3 to a pH of about 11, or from about pH 3 to about pH 7, depending on the formulation and route of administration. In alternative embodiments, the pH may be adjusted to a range from about pH 5.0 to about pH 8.0.

In an embodiment, a pharmaceutical composition of the invention comprises an effective amount of at least one IC and/or amylinomimetic, together with one or more pharmaceutically acceptable excipients. Optionally, a pharmaceutical composition may include a second active ingredient useful in the prevention or treatment of metabolic disease or condition described herein.

The pharmaceutical compositions may be formulated for administration in any manner known in the art. By way of example, when formulated for oral administration or parenteral administration, the pharmaceutical composition is most typically a solid, liquid solution, emulsion or suspension, while inhaleable formulations for pulmonary or nasal administration are generally liquids or powders. A pharmaceutical composition may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as an IC or amylinomimetic. The term refers to any pharmaceutical excipient that may be administered without undue toxicity. Pharmaceutically acceptable excipients are determined in part by the particular composition being administered, as well as by the particular method used to administer the composition. Accordingly, there exist a wide variety of suitable formulations of pharmaceutical compositions for use in the methods of the present invention (see, e.g. Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

More particularly, when intended for oral use, e.g., tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, the pharmaceutical composition of the invention may be formulated as a suspension comprising an IC or amylinomimetic in admixture with at least one pharmaceutically acceptable excipient suitable for the manufacture of a suspension. In yet another embodiment, an IC or amylinomimetic may be formulated as dispersible powder and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical composition of the present invention may also be in the form of an oil-in-water emulsion. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

In another embodiment, the pharmaceutical composition of the invention may be formulated as a sterile injectable preparation, such as a sterile injectable aqueous emulsion or oleaginous suspension. This emulsion or suspension may be formulated according to the known art using those suitable dispersing or wetting agents and suspending agents such as those that have been mentioned above. In another embodiment, the sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Certain IC or amylinomimetics may be substantially insoluble in water and sparingly soluble in most pharmaceutically acceptable protic solvents and in vegetable oils. However, the compounds may be soluble in medium chain fatty acids (e.g., caprylic and capric acids) or triglycerides and have high solubility in propylene glycol esters of medium chain fatty acids. Also contemplated for use in the methods of the invention are compositions, which have been modified by substitutions or additions of chemical or biochemical moieties which make them more suitable for delivery (e.g., increase solubility, bioactivity, palatability, decrease adverse reactions, etc.), for example by esterification, glycation, PEGylation, etc.

An IC or amylinomimetic may also be formulated for oral administration in a self-emulsifying drug delivery system (SEDDS). Lipid-based formulations such as SEDDS are particularly suitable for low solubility compounds, and can generally enhance the oral bioavailability of such compounds.

In an alternative embodiment, cyclodextrins may be added as aqueous solubility enhancers. Cyclodextrins include hydroxypropyl, hydroxyethyl, glucosyl, maltosyl and maltotriosyl derivatives of alpha-, beta-, and gamma-cyclodextrin. In one embodiment a cyclodextrin solubility enhancer is hydroxypropyl-beta-cyclodextrin (HPBC), which may be added to any of the above-described compositions to further improve the aqueous solubility characteristics of a GLP-1 molecule or agonist thereof. In one embodiment, the composition comprises 0.1% to 20% hydroxypropyl-beta-cyclodextrin, and in one embodiment 1% to 15% hydroxypropyl-beta-cyclodextrin, and in one embodiment from 2.5% to 10% hydroxypropyl-beta-cyclodextrin. The amount of solubility enhancer employed will depend on the amount of IC or amylinomimetic in the composition.

Dosage and administration are adjusted to provide sufficient levels of the active agent(s) in a pharmaceutical composition or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Whether an administration is acute or chronic may also be considered in determining dosage. Long-acting pharmaceutical compositions may be administered every 3 to 4 days, every week, or once every two weeks depending on half-life and clearance rate of the particular formulation. In one embodiment, IC or amylinomimetics used in the methods of the present invention are formulated for sustained release.

Exemplary treatment regimens include, but are not limited to, administration via injection to achieve a dose of from about 0.1 µg/kg to about 0.5 µg/kg or from about 0.005 µg/kg to about 0.2 µg/kg of the IC or amylinomimetic. Other exemplary treatment regimens include, but are not limited to, administration via injection to achieve a dose of from about 1 µg/day to about 1 mg/day, from about 100 ug/day to 800 ug/day, from about 400 ug/day to about 600 ug/day, or from about 500 µg/day to about 12,000 µg/day of the IC or amylinomimetic in a single or divided dose.

Still other exemplary treatment regimens include, but are not limited to, pulmonary administration to achieve a dose from about 100 ug/day to 800 ug/day, from about 400 ug/day to about 600 ug/day or 100 µg/day to about 12,000 µg/day of the IC or amylinomimetic in a single or divided dose; nasal administration to achieve a dose from about 100 ug/day to 800 ug/day, from about 400 ug/day to about 600 ug/day or from about 10 µg/day to about 12,000 µg/day of the IC or amylinomimetic in a single or divided dose; and buccal administration to achieve a dose from about 100 ug/day to 800 ug/day, from about 400 ug/day to about 600 ug/day or from about 100 µg/day to about 12,000 µg/day of the IC or amylinomimetic in a single or divided dose.

More specifically, pharmaceutical formulations contemplated for use in the methods of the invention may comprise approximately 0.01 to 6.0% (w/v), preferably 0.05 to 1.0%, of the compound, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl-, ethyl-, propyl- and butyl-parabens and phenol. Such a preservative is generally included if the formulated peptide is to be included in a multiple use product.

In a particular embodiment of the present invention, a pharmaceutical formulation of the present invention may contain a range of concentrations of the compound, e.g., between about 0.01% to about 98% w/w, or between about 1 to about 98% w/v, or in some embodiments between 80% and 90% w/v, or in some embodiments between about 0.01% to about 50% w/v, or and in one embodiment between about 10% to about 25% w/v in this embodiment. A sufficient amount of water for injection may be used to obtain the desired concentration of solution.

Additional tonicifying agents such as sodium chloride, as well as other known excipients, may also be present, if desired. In one embodiment however, if such excipients maintain the overall tonicity of the formulations. An excipient may be included in the presently described formulations at various concentrations. For example, an excipient may be included in the concentration range from about 0.02% to about 20% w/w, preferably between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form.

The pharmaceutical formulations may be composed in various forms, e.g., solid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the present peptide formulations, for example, water or an aqueous/organic solvent mixture or suspension.

The stability of a peptide formulation of the present invention can be enhanced by maintaining the pH of the formulation in the range of about 3.0 to about 7.0 when in liquid form. In one embodiment the pH of the formulation can be maintained in the range of about 3.5 to 5.0, or about 3.5 to 6.5, and even from about 3.7 to 4.3, or about 3.8 to 4.2. A particularly useful pH may be about 4.0.

A buffer usable in the practice of the present invention is an acetate buffer (for example at a final formulation concentration of from about 1.5, e.g., 1.5 to about 60 mM), phosphate buffer (for example at a final formulation concentration of from about 1.5, e.g., 1.5, to about 30 mM) or glutamate buffer (for example at a final formulation concentration of from about 1.5, e.g., 1.5 to about 60 mM). Acetate is particularly usable at a final formulation concentration of from about 5 to about 30 mM.

A stabilizer may be included in the present formulation but, and importantly, is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic subject, i.e., the carbohydrate is not metabolized to form unacceptably large concentrations of glucose in the blood. Such carbohydrates are well known in the art as suitable for diabetics. Sucrose and fructose are suitable for use with the compound in non-diabetic subjects (e.g., treating obesity).

If a stabilizer is included, the compound can be stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol and sucrose are useful polyhydric alcohol. Another useful feature of the lyophilized formulations of the present invention is the maintenance of the tonicity of the lyophilized formulations described herein with the same formulation component that serves to maintain their stability. Mannitol is a useful polyhydric alcohol for this purpose. Sucrose and trehalose are also useful.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Anti-microbial agents should be evaluated to ensure compatibility with all other components of the formula, and their activity should be evaluated in the total formula to ensure that a particular agent that is effective in one formulation is not ineffective in another. It is not uncommon to find that a particular anti-microbial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), in one embodiment the range for each preservative, alone or in combination with others, is: benzyl alcohol (0.1-1.0%), or m-cresol (0.1-0.6%), or phenol (0.1-0.8%) or combination of methyl (0.05-0.25%) and ethyl- or propyl- or butyl-(0.005%-0.03%) parabens. The parabens are lower alkyl esters of parahydroxybenzoic acid.

A detailed description of each preservative is set forth in "Remington's Pharmaceutical Sciences" as well as Pharmaceutical Dosage Forms: Parenteral Medications, Vol. 1, 1992, Avis et al.

Pramlintide, human [25,28,29]Pro-amylin, does not have a tendency to adsorb onto the glass in a glass container when in a liquid form, therefore, a surfactant is not required to further stabilize the pharmaceutical formulation. However, with regard to compounds Which do have such a tendency when in liquid final, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-Cholamidopropyl) dimethylammonio]propanesulfonic acid), BRIJ® (e.g., Brij 35, which is (polyoxyethylene(23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations preferably may be isotonic or substantially isotonic.

In one embodiment a vehicle for parenteral products is water. Water of suitable quality for parenteral administration can be prepared either by distillation or by reverse osmosis. Water for injection is the aqueous vehicle in some embodiments for use in the pharmaceutical injectable formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass. The biological and chemical properties of the compound may be stabilized by formulation and lyophilization in a Wheaton Type I-33 borosilicate serum vial to a final concentration of 0.1 mg/ml and 10 mg/ml of the compound in the presence of 5% mannitol, and 0.02% Tween 80.

In order to permit introduction of a needle from a hypodermic syringe into a multiple-dose vial and provide for resealing as soon as the needle is withdrawn, the open end of each vial is in some embodiments sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. The inventors have also discovered that these stoppers pass the stopper integrity test when tested using subject use patterns, e.g., the stopper can withstand at least about 100 injections. Alternatively, the peptide can be lyophilized in vials, syringes or cartridges for subsequent reconstitution. Liquid formulations of the present invention can be filled into one or two chambered cartridges, or one or two chamber syringes, and can be a "pen" type delivery device.

Each of the components of the pharmaceutical formulation described above is known in the art and is described in Pharmaceutical Dosage Forms: Parenteral Medications, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the method of sterilization for liquid formulations in some embodiments of the present invention. The sterile filtration involves filtration through 0.45 µm and 0.22 µm (1 or 2) which may be connected in series. After filtration, the solution is filled into appropriate vials or containers.

The liquid pharmaceutical formulations of the present invention are intended for parenteral administration. Suitable routes of administration include intramuscular, intravenous, subcutaneous, intradermal, intraarticular, intrathecal and the like. The subcutaneous route of administration is useful. Mucosal delivery is also useful. These routes include, but are not limited to, oral, nasal, sublingual, pulmonary and buccal routes which may include administration of the peptide in liquid, semi-solid or solid form. Administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The compounds may be provided in dosage unit form containing an amount of the compound with or without insulin or glucose (or a source of glucose) that will be effective in one or multiple doses to treat or help in treating the disease or disorder described herein and/or unwanted side effects of the disease or disorder treatment/medication as described herein. As will be recognized by those in the field, an effective amount of therapeutic agent will vary with many factors including the age and weight of the subject, the subject's physical condition, the condition to be treated, and other factors.

However, typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. Also contemplated are other dose ranges such as 0.1 microgram to 1 milligram of the compound per dose. Thus, exemplary doses may be 30, 60, 120, 240, or 360 ug of the compound per dose. The doses per day may be delivered in discrete unit doses or provided continuously in a 12 or 24 hour period (as by a long acting release formulation), or any portion of that 24 hour period. The number of doses per day may be from 1 to about 4 doses per day, although it can be more. Continuous delivery can be in the form of continuous infusions. Exemplary doses and infusion rates include from 0.005 nmol/kg to about 20 nmol/kg per discrete dose or from about 0.01/pmol/kg/min to about 10 µmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 ug to about 8 mg per day, whereas total dose/delivery of the pharmaceutical composition given s.c may be about 6 ug to about 16 or 24 mg per day.

In another embodiment the IC and/or amylinomimetic is provided in a long-acting (or sustained) release formulation. In one such embodiment superior release profiles (such as those characterized by a ratio of $C_{max}$ to $C_{ave}$ of about 3 or less) can be achieved with a formulation containing few components by controlling the coacervating agent to polymer solvent ratio, such as silicone oil to polymer solvent ratio, in the manufacturing process, thereby achieving a low pore volume. Further it has been found that a superior desired release profile can be achieved by controlling the coacervation process, such as the length of time of addition of coacervating agent such as silicone oil, the length of the hold period after addition, and the length of the transfer to a quench agent. It has also been found that superior low pore volume sustained release compositions, such as microparticles, can be achieved by controlling inner emulsion droplet size. Further, it has been found that controlling particle size and particle size distribution further provides and contributes to superior desired release profiles (such as characterized by a Cmax to Cave ratio of about 3 or less) and a more consistent lot-to-lot profile. In one embodiment a sustained release composition can comprise as few components as a biocompatible polymer, the IC and/or amylinomimetic agent, and optionally a sugar. The polypeptide and sugar are preferably dispersed in the polymer. The polypeptide and sugar can be dispersed separately or, preferably, together. The sustained release composition provides a desirable and consistent release profile. In a particular embodiment, the profile is characterized as having a ratio of $C_{max}$ to $C_{ave}$ of about 3 or less. In one embodiment, the biologically active polypeptide is an antidiabetic or glucoregulatory polypeptide, such as GLP-1, GLP-2, exendin-3, exendin-4 or an analog, derivative or agonist thereof. The sugar is can include sucrose, mannitol or a combination thereof.

Additionally or alternatively, the sustained release composition comprises a biocompatible polymer, the IC and/or amylinomimetic agent and optionally a sugar, wherein the composition (e.g., microsphere) has a total pore volume of about 0.1 mL/g or less. In a specific embodiment, the total pore volume can be determined using mercury intrusion porosimetry.

Additionally or alternatively, the sustained release composition consists essentially of or, alternatively consists of, a biocompatible polymer, exendin-4 at a concentration of about 1 to 5% w/w and sucrose or mannitol at a concentration of about 1 to 5% w/w. More particularly the agent is at 2 to 3%. More particularly the sugar is at 2%. The biocompatible polymer is typically a poly lactide coglycolide polymer.

The sustained release composition (e.g. microsphere) can be formed by combining an aqueous phase comprising water, the agent(s) as described herein, and optionally a sugar with an oil phase comprising a biocompatible polymer and a solvent for the polymer; forming a water-in-oil emulsion by, for example, sonicating or homogenizing, the mixture; adding silicone oil to the mixture to form embryonic microparticles; transferring the embryonic microparticles to a quench solvent to harden the microparticles; collecting the hardened microparticles; and drying the hardened microparticles. In a particular embodiment, the silicone oil is added in an amount sufficient to achieve a silicone oil to polymer solvent ratio of about 1.5:1. Additionally or alternatively, the polymer is present in the oil phase at about 10% w/v or less.

The agent, e.g. exendin-4, can be present in the composition described herein at a concentration of about 0.01% to about 10% w/w based on the total weight of the final composition. In addition, the sugar, e.g. sucrose, can be present in a concentration of about 0.01% to about 5% w/w of the final weight of the composition.

As discussed herein the sustained release composition can be administered to a human, or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray).

The use of a sugar in the sustained release compositions improves the bioavailability of the incorporated agent(s) and minimizes loss of activity due to instability and/or chemical interactions between the polypeptide and other components contained or used in formulating the sustained release composition, while maintaining an excellent release profile.

In one embodiment the composition contains active agent exendin-4 at about 5%, sugar at about 2% and biopolymer. In another embodiment the composition contains active agent exendin-4 at about 3%, sugar at about 2% and biopolymer In a further such embodiment the composition contains a PLGA polymer. In yet a further embodiment the composition contains a PLG 4A polymer, which comprises about a 50 mole percent DL lactide to 50 mole percent glycolide ratio, with an uncapped free carboxylic acid end group ("4A" designation). In yet a further embodiment the composition is formed as a microparticle having a particle size, particle size distribution, and total pore volume as described herein. In an even further embodiment the total pore volume is less than about 0.1 mL/g, mean particle size DV50 can be about 50 microns with a distribution of a lower limit DV10 of about 30 microns and an upper limit DV90 of about 90 microns. In yet a further embodiment, the microparticles are formed, obtained by or obtainable by the processes described herein. In one such embodiment the process is a water/oil/oil ("W/O/O") process wherein the inner emulsion size is as described herein. In addition, the process can include a silicone oil coacervate, which can be at about a 1.5 to 1 ratio with polymer solvent. Further the process can include controlling of the coacervation step as described herein, and even further where a transfer of coacervate to the inner emulsion occurs at about 3 minutes or less, a hold step of about 1 minute or less, and a rapid transfer step over a period of less than about 3 minutest to a quench/hardening solvent. In a further embodiment the solvent is a dual solvent, preferably a heptane/ethanol mix.

In a further embodiment the compositions can be further formulated to a form suitable for nasal delivery or for injection through a needle into a host. An injectable composition can comprise microparticle compositions as described herein in an aqueous injection vehicle of appropriate viscosity. The aqueous injection vehicle can have a viscosity of at least 20 cp at 20° C., and further can have a viscosity greater than 50 cp and less than 60 cp at 20° C. The microparticles can be suspended in the injection vehicle at a concentration of greater than about 30 mg/ml to form a suspension, the fluid phase of the suspension having a viscosity of at least 20 cp at 20° C. The composition may also comprise a viscosity enhancing agent, a density enhancing agent, a tonicity enhancing agent, and/or a wetting agent. The viscosity of the injection vehicle provides injectability of the composition through a needle ranging in diameter from about 18-23 gauge, and in one embodiment about 18-25 gauge needle, and in one embodiment about a 25 gauge needle.

In one embodiment suitable for passage thru a 23 gauge needle, the injection vehicle comprises sodium carboxymethylcellulose at 3.0% (w/v), sodium chloride at 0.9% (w/v), and Polysorbate 20, NF (Tween 20) at 0.1% (v/v) or optionally at 0.5%, in water. The solution is optionally buffered. In a further embodiment, an exenatide-containing microparticles as described above are suspended in an injection vehicle of sodium carboxymethylcellulose at 3.0% (w/v), sodium chloride at 0.9% (w/v), and Polysorbate 20, NF (Tween 20) at 0.1% (v/v) or optionally at 0.5%, in water. In a further embodiment the concentration of suspended exenatide-microparticles is greater than about 30 mg/ml. Typically about 100 to 200 mg dry microparticles is suspended per mL of vehicle.

Polymers suitable to form the sustained release composition are biocompatible polymers which can be either biodegradable or non-biodegradable polymers or blends or copolymers thereof. A polymer is biocompatible if the polymer and any degradation products of the polymer are non-toxic to the recipient and also possess no significant deleterious or untoward effects on the recipient's body, such as a substantial immunological reaction at the injection site. Biodegradable, as defined herein, means the composition will degrade or erode in vivo to form smaller units or chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, end group chemistry and rate of dissolution of polymer in solvent. Typically, an acceptable range of molecular weight is of about 2,000 Daltons to about 2,000,000 Daltons. In one embodiment, the polymer is biodegradable polymer or copolymer. In a more useful embodiment, the polymer is a poly(lactide-co-glycolide) (hereinafter "PLG") with a lactide:glycolide ratio of about 1:1 and a molecular weight of about 10,000 Daltons to about 90,000 Daltons. In an even more useful embodiment, the molecular weight of the PLG used in the present invention has a molecular weight of about 30,000 Daltons to about 70,000 Daltons such as about 50,000 to about 60,000 Daltons.

The PLGs can possess acid end groups or blocked end groups, such as can be obtained by esterifying the acid. Excellent results were obtained with a PLG with an acid end group.

Polymers can also be selected based upon the polymer's inherent viscosity. Suitable inherent viscosities include about 0.06 to 1.0 dL/g, such as about 0.2 to 0.6 dL/g, and in one embodiment between about 0.3 to 0.5 dL/g. In one embodiment polymers are chosen that will degrade in 3 to 4 weeks. Suitable polymers can be purchased from Alkermes, Inc. under the tradename Medisorb®, such as those sold as 5050 DL 3A or 5050 DL 4A. Boehringer Ingelheim Resomer® PLGs may also be used, such as Resomer® RG503 and 503H.

Examples of further specific PLG polymers suitable for use are: Polymer 2A: Poly(lactide-co-glycolide); 50:50 lactide:glycolide ratio; 12.3 kD Mol. Wt.; IV=0.15 (dL/g); and Polymer 4A: Poly(lactide-co-glycolide); 50:50 lactide:glycolide ratio; Mol. Wt. 45-64 kD; IV=0.45-0.47 (dL/g).

It is known in the art (see, for example, Peptide Acylation by Poly(alpha-Hydroxy Esters) by Lucke et al., Pharmaceutical Research, Vol. 19, No. 2, p. 175-181, February 2002) that proteins and peptides which are incorporated in PLG matrices can be undesirably altered (e.g., degraded or chemically modified) as a result of interaction with degradation products of the PLG or impurities remaining after preparation of the polymer. As such, the PLG polymers used in the preparation of the majority of microparticle formulations described herein can be purified prior to preparation of the sustained release compositions using art recognized purification methods. A useful purification scheme will remove will remove or reduce residual building blocks, e.g. lactic acid, glycolic acid, lactide, glycolide, used to form the polymer to a level that reduces or minimizes an impurity caused by reaction, e.g. transesterification, condensation, of the residual building block with the peptide drug.

The sustained release composition can be formed into many shapes such as a film, a pellet, a cylinder, a disc or a microparticle. A microparticle, as defined herein, comprises a polymer component having a diameter of less than about one millimeter and having biologically active polypeptide dispersed or dissolved therein. A microparticle can have a spherical, non-spherical or irregular shape. Typically, the microparticle will be of a size suitable for injection. A typical size range for microparticles is 1000 microns or less. In a particular embodiment, the microparticle ranges from about one to about 180 microns in diameter. In yet further embodiments, superior release profiles are obtained when microparticles range from about 1 to 100 microns, from about 30 to 90 microns, from about 50 to 70 microns, and even further the mean particle size can be from about 50 to 60 microns. In one embodiment the mean particle size is not less than or is equal to about 50, 60 or 70 microns, and preferably less than about 80, 90, or 100 microns. At larger particles sizes, particles are preferably substantially non-aggregated to allow passage through a 23 gauge needle, and in one embodiment a 25 gauge needle. In yet another embodiment consistent and superior release profiles are obtained by controlling particle size distribution. In one embodiment a mean particle size is about 50 microns and the lower and upper range of particles are about 30 and 90 microns, respectively. Distribution of microparticles can be described using a mean diameter of the volume. Mean diameter of the volume distribution represents the center of gravity of the distribution and is a type of "average particle size." In one embodiment a composition has a mean diameter of the volume distribution of about 50 to 70 microns, about 50 to 60 microns or about 50, 60 or 70 microns, with a Distribution of Volume (DV) of less than or about 5%, 10%, or 15% at 30 microns and a DV of greater than or about 80%, 85%, 90% or 95% at 90 microns. In one embodiment a composition has a mean diameter of the volume distribution of about 60 microns, with a Distribution of Volume (DV) of less than or about 10% at 30 microns and a DV of greater than or about 90% at 90 microns.

In other embodiments additional excipients can be added to the formulations of the claimed invention as is well known in the art. However, an excellent release profile can be achieved with the simple formulations described herein. Such additional excipients can increase or decrease the rate of release of the agent, and/or promote its stability or another desirable property of the agent. Ingredients which can substantially increase the rate of release include pore forming agents and excipients which facilitate polymer degradation. For example, the rate of polymer hydrolysis is increased in non-neutral pH. Therefore, an acidic or a basic excipient such as an inorganic acid or inorganic base can be added to the polymer solution, used to form the microparticles, to alter the polymer erosion rate. Ingredients which can substantially decrease the rate of release include excipients that decrease the water solubility of the agent.

Yet another embodiment of the described sustained release formulations consists essentially of the biocompatible polymer, the agent and the sugar. By "consists essentially of" is meant the absence of ingredients which substantially increase the rate of release of the active agent from the formulation. Examples of additional excipients which would not be expected to substantially increase or decrease the rate of release of the agent include additional active agents and inert ingredients.

In yet another embodiment, the formulation consists of the biocompatible polymer, the agent and the sugar. By "consists of" is meant the absence of components or ingredients other than those listed and residual levels of starting materials, solvents, etc. from the process.

Alternatively or additionally, the sustained release composition has low porosity. In such embodiments, the sustained release composition comprises a biocompatible polymer, a biologically active polypeptide and a sugar wherein the composition has a total pore volume of about 0.1 mL/g or less. In addition the total pore volume can be from 0.0 to 0.1 mL/g and from 0.01 to less than 0.1 mL/g. It has been found that this very small total pore volume leads to a small initial burst (release) of agent, and further that it promotes a slower and/or longer sustained release profile than conventional formulations, and allows shifting of a Cmax to a later time in a profile. In a specific embodiment, the total pore volume is determined using mercury intrusion porosimetry, e.g., as described in more detail below.

In another embodiment when the sustained release compositions have a low porosity as described herein, which serves to both reduce initial release and to provide longer sustained release with a desirable Cmax to Cave ratio, additional excipients can be present. Such agents preferably have little or no substantial effect on release rate. Such excipients can include those that provide or enhance agent stability, either during manufacturing, storage or release. Suitable stabilizers include, for example, carbohydrates, amino acids, fatty acids and surfactants and are known to those skilled in the art. Further, stabilizers include "antioxidants" such as methionine, vitamin C, vitamin E and maleic acid. The antioxidant can be present as part of a stabilized aqueous formulation or added into the polymer phase. Further a pH buffer can be added. Buffers are solutions containing either a weak acid and a related salt of the acid, or a weak base and a salt of the base. Buffers can maintain a desired pH to stabilize the formulation during any step of manufacturing, storage or release. For example, the buffer can be a monobasic phosphate salt or dibasic phosphate salt or combinations thereof or a volatile buffer such as ammonium bicarbonate. Other buffers include but are not limited to acetate, citrate, succinate and amino acids such as glycine, arginine and histidine. The buffer can be present in the formulation from about 0% to about 10% of the total weight, and preferably less than about 10, 15, 20, 25 or 30 mM. In view of the surprisingly new physical aspects of the microparticles and the novel methods of manufacture as described herein, it is believed that the invention provides novel microparticles and processes even when excipients are present that affect rate of release. The novel properties of the microparticles can counter or reduce undesired release effects of a needed excipient (such as a stabilizing salt). In another embodiment excipients are present at levels that substantially affect the rate of release to further enhance a desired release profile.

As discussed herein, sustained release compositions can be administered according to methods generally known in the art. The composition of this invention can be administered to a subject (e.g., a human in need of the agent) or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), orally, by needle-free injection (see for example U.S. Pat. Nos. 5,312,335 and 5,630,796, which are incorporated herein by reference) or in situ delivery (e.g., by enema or aerosol spray). The sustained release composition can be administered using any dosing schedule which achieves the desired therapeutic levels for the desired period of time. For example, the sustained release composition can be administered and the subject monitored until levels of the drug being delivered return to baseline. Following a return to baseline, the sustained release composition can be administered again. Alternatively, the subsequent administration of the sustained release composition can occur prior to achieving baseline levels in the subject.

A sustained release of biologically active polypeptide can be a release of the polypeptide from the sustained release composition which occurs over a period which is longer than that period during which a biologically significant amount of the polypeptide would be available following direct administration of a solution of the polypeptide. In one embodiment a sustained release can be a release which occurs over a period of at least about 12 hours or 24 hours or any hour increment thereof. In yet another embodiment the sustained release is at least about one week, such as at least about two weeks, at least about three weeks or at least about four weeks. The sustained release can be a continuous or a discontinuous release, with relatively constant or varying rates of release. The continuity of release and level of release can be affected by the type of polymer composition used (e.g., monomer ratios, molecular weight, block composition, and varying combinations of polymers), polypeptide loading, and/or selection of excipients to produce the desired effect. Sustained release compositions and methods to make them can be found in, for example, PCT/US2005/012989 filed Apr. 15, 2005, which is incorporated herein in its entirety D. Combination Therapy In another aspect of the invention, it is also possible to combine an IC or amylinomimetic useful in the methods of the present invention, with one or more other active ingredients useful in the prevention of a metabolic disease or disorder as described herein. For example, an IC or amylinomimetic may be combined with one or more other compounds (even another IC or amylinomimetic), in a unitary dosage form, or in separate dosage forms intended for simultaneous or sequential administration to a subject in need of treatment.

When administered sequentially, the combination may be administered in two or more administrations. In an alternative embodiment, it is possible to administer one or more IC or amylinomimetics and one or more additional active ingredients by different routes. The skilled artisan will also recognize that a variety of active ingredients may be administered in combination with IC or amylinomimetic that may act to augment or synergistically enhance the treatment, prevention, amelioration, attenuation, or delay of a metabolic disease or disorder as described herein.

According to the methods herein, an IC or amylinomimetic may be: (1) co-formulated and administered or delivered simultaneously in a combined formulation; (2) delivered by alternation or in parallel as separate formulations; or (3) by any other combination therapy regimen known in the art. When delivered in alternation therapy, the methods may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In order that the invention described herein may be more fully understood, the following examples are set forth. It should be understood that these examples are for illustrative purposes only and are not to be considered as limiting this invention in any manner.

EXAMPLES

Example 1

Treatment with a Glucoregulatory Molecule Exendin, Ameliorates a Metabolic Disease as Described Herein In three placebo-controlled, 30-week, phase 3 clinical trials and a cohort followed in open label extensions (n=393, 62% male, age 56+/−10 years, HbA1C of 8.3+/−1.0%, BMI of 33.7+/−5.7 kg/m$^2$; mean+/−SD), exenatide (at 5 or 10 microgram BID SC) improved glycemic control and reduced body weight in subjects with type 2 diabetes unable to achieve glycemic control with metformin, sulphonylurea, or both.

Patients. Main inclusion criteria for the three 30-week trials have been detailed elsewhere (Buse et al., Diabetes Care 27:2628-2635 (2004); DeFronzo et al., Diabetes Care 28:1092-1100 (2005); Kendall et al., Diabetes Care 28:1083-1091 (2005)). Briefly, patients were to be between 16 and 75 years of age with T2DM treated for at least 3 months prior to screening with greater than or equal to 1500 mg/day MET (metformin), or at least the maximally-effective dose of an SFU (sulfonylurea), or a combination of MET and SFU. Additional inclusion criteria were an HbA$_{1c}$ between 7.1% and 11.0%, inclusive, fasting plasma glucose concentration (FPG) <240 mg/dL, and body mass index (BMI) of 27 to 45 kg/m$^2$. To enroll in the open-label, uncontrolled extensions of the 30-week studies, subjects had to complete the antecedent 30-week placebo-controlled trial.

Study Design and Endpoints. The initial studies were stratified, balanced, randomized, double-blind, placebo-controlled, parallel-group clinical studies designed to evaluate glycemic control, as assessed by HbA$_{1c}$, and safety in T2DM patients. In one study, subjects were treated with maximally effective MET doses (greater than or equal to 1500 mg/day), in the second study subjects were treated with maximally effective doses of an SFU, and in the third study subjects were treated with a combination of MET and an SFU (Buse et al., 2004; DeFronzo et al., 2005; Kendall et al., 2005). SFU regimens are described in further detail in published accounts of these trials (Buse et al., 2004; DeFronzo et al., 2005; Kendall et al., 2005). Subjects were randomized to receive placebo, 5 µg exenatide, or 10 µg exenatide BID. Study medication was self-injected subcutaneously in the abdomen within 15 minutes before meals in the morning and evening. Subjects who completed the 30-week studies had the option to continue in open-label extensions, in which all subjects received 5 µg exenatide BID for 4 weeks, followed by 10 µg exenatide BID thereafter.

Figure 2:
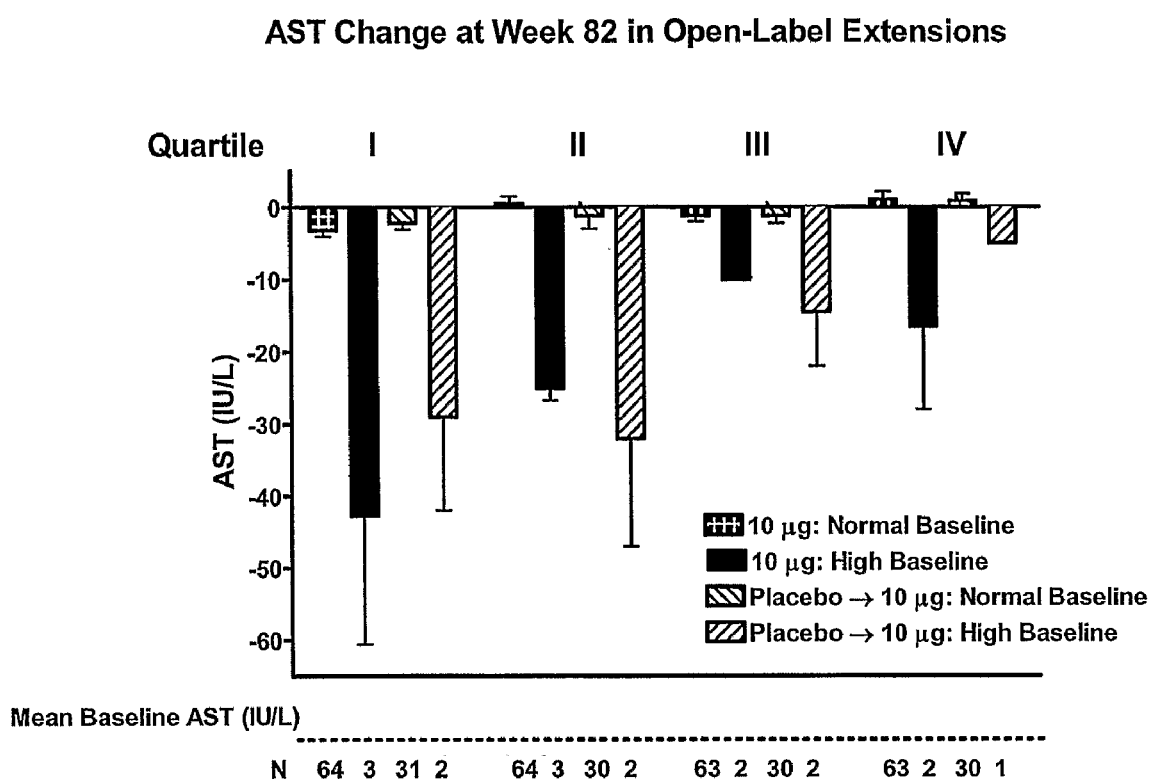
FIG. 2 depicts the effect of an IC on the change in aspartate aminotransferase (AST) level at week 82 in an open-label extension study.
Figure 3:
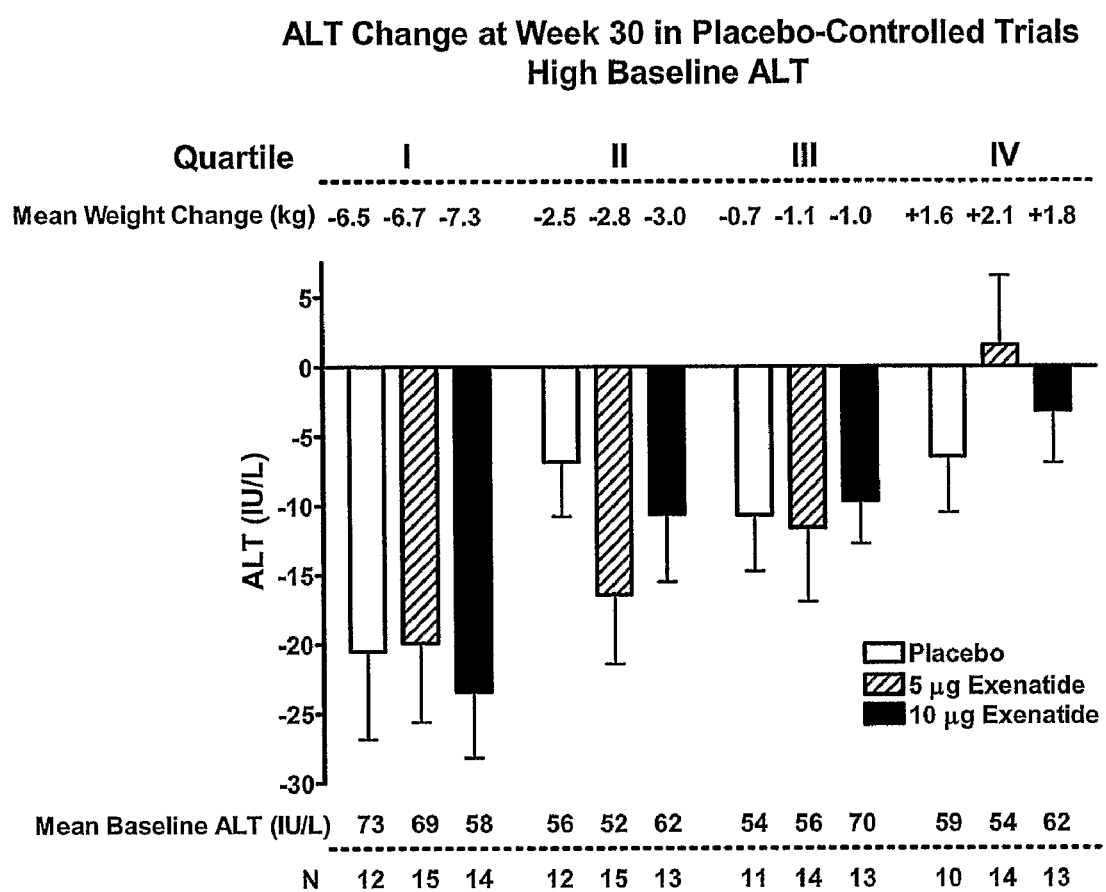
FIG. 3 depicts the effect of an IC on the change in alanine aminotransferase (ALT) level at week 30 in placebo-controlled trials, in subjects initially having a high baseline ALT level.
Figure 4:
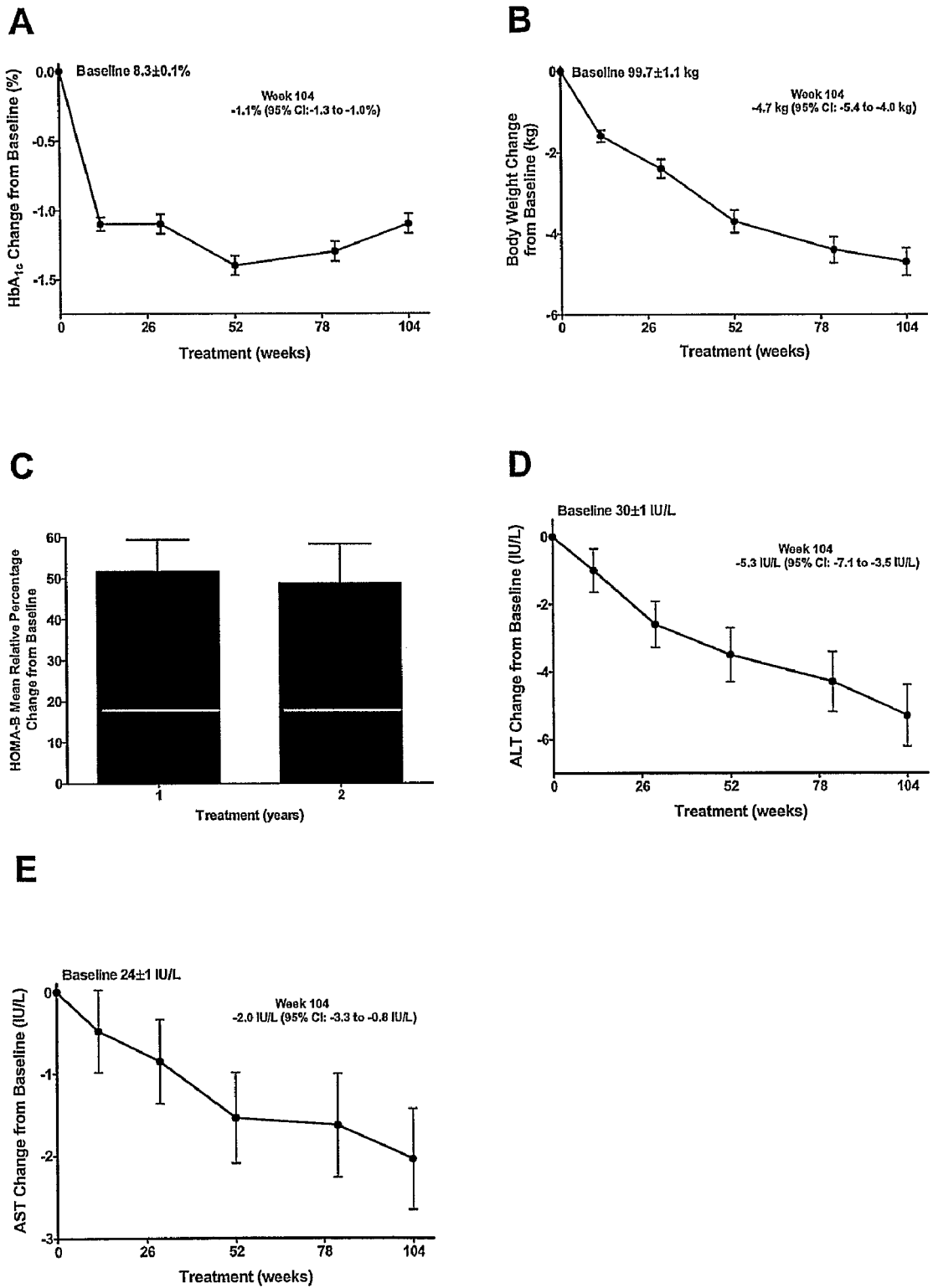
FIG. 4. Exenatide effects on metabolic parameters in T2DM patients inadequately controlled by MET, SFU, or combined MET/SFU therapy. (A) Exenatide elicited sustained reduction in $HbA_{1c}$ ($p<0.05$). (B) Exenatide treatment was associated with progressive weight reduction ($p<0.05$). (C) HOMA-B increased with exenatide treatment ($p<0.05$). (D) Exenatide reduced ALT ($p<0.05$). (E) Exenatide reduced AST ($p<0.05$). Subjects were randomized to the placebo, 5 μg exenatide, or 10 μg exenatide treatment arms during the initial 30-week placebo-controlled studies before all were transitioned to open-label exenatide treatment. All subjects had achieved a minimum of 2-years of exenatide exposure for this analysis. Mean±SEM. N=283 (A, B, D, E) or N=112 (C).

A post hoc interim analysis of the liver function marker ALT (alanine aminotransferase) and AST (aspartate aminotransferase) was performed on the cohort followed for 82 weeks (30 weeks in the placebo-controlled trials plus 52 weeks in the open-label extensions) with a subanalysis by body weight change quartiles. (A quartile for a data set is one of three data points that divide the set of data into four parts, each containing a quarter of the data. The first point marks the lower quartile boundary at the 25th percentile. The second marks the middle quartile (or midpoint of the data set), the median or the 50th percentile. The last marks the upper quartile (or 75th percentile) of a frequency distribution.) The baseline ALT thresholds used to stratify subjects to normal (n=343, ALT 25+/−1 IU/L) versus elevated (n=50, ALT 58+/−2 IU/L) were </=37 IU/L for females and </=48 IU/L for males. The results of the analysis are summarized in FIGS. 1-3.

Subjects with normal baseline ALT who were treated with exenatide for 82 weeks (n=230) had minimal ALT changes: −1+/−U/L from baseline ALT 25+/−1 IU/L and baseline weight 99.1+/−1.4 kg. In contrast there was an overall lowering towards more physiological ALT levels in the 82-week exenatide-treated, elevated-ALT subgroup; −20+/−4 IU/L from baseline ALT 58+/−3 IU/L and baseline weight 104.4+/−3.5 kg (n=35), with a pattern of greater responses in subjects who lost more weight (greatest weight loss quartile): exenatide group (n=9): −35+/−8 IU/L and −12.8+/−1.0 kg. A similar trend was observed in subjects with normal baseline ALT in the greatest weight loss quartile exenatide group (n=58): −4+/−1 IU/L and −11.8+/−0.7 kg. An alternative analysis, grouping subjects by normal baseline ALT values of </=19 IU/L for females and </=30 IU/L for males (Prati et al., Ann. Intern. Med. 137(1):1-10 (2002)), gave similar results. At week 82 subjects in the high baseline ALT/highest weight loss quartile had ALT reductions of −18+/−IU/L with weight reductions of −13.7+/−1.2 kg (combined exenatide groups, n−32).

Using elevated serum ALT and AST levels as a biochemical marker of NAFLD and NASH, reductions in ALT were noted in subjects treated with exenatide for 82 weeks. While not to be bound by theory, the beneficial effect on liver function in subjects with type 2 diabetes appears to be associated with weight loss, in part elicited by improved glycemic control.

Example 2

Treatment with Exendin Ameliorates a Metabolic Disease—Further Analysis

The study in Example 1 was continued to 104 weeks. FIGS. 4-8 present an analysis of data from the 104-week study. Results are consistent with the 82-week analysis of Example 1.

In this interim analysis, the objectives were to evaluate the change from baseline for $HbA_{1c}$, body weight, and hepatic biomarkers plus safety. The 2-year completer cohort was defined as all subjects who had the opportunity to achieve 2-years of exenatide exposure, irrespective of their treatment arm in the 30-week placebo-controlled trials. Plasma/serum analytes, $HbA_{1c}$, and safety were measured as previously described (Buse et al., Diabetes Care 27:2628-2635 (2004); DeFronzo et al., Diabetes Care 28:1092-1100 (2005); Kendall et al., Diabetes Care 28:1083-1091 (2005)). No samples were collected for measurement of serum lipid concentrations. All safety analyses were performed using the intent-to-treat (ITT) population, defined as all patients who received at least one injection of exenatide starting from the beginning of the open-label extension studies and who enrolled with timing such that they could achieve 2 years of exenatide treatment prior to the analysis cut-off date. The intensity of hypoglycemic episodes was defined as mild, moderate or severe. For mild or moderate hypoglycemia, patients reported symptoms consistent with hypoglycemia that may have been documented by a blood glucose concentration value (<60 mg/dL), and did not require the assistance of another person. For severe hypoglycemia, patients required the assistance of another person to obtain treatment for their hypoglycemia, including food, drink, intravenous glucose or intramuscular glucagon.

Statistical Analysis. Randomization was stratified according to screening $HbA_{1c}$ values (<9.0% and ≧9.0%) to achieve a balanced distribution of subjects. Missing endpoint results were imputed from scheduled or unscheduled post-baseline visits using the last observation carried forward (LOCF) method. Additional information on statistical methods can be found in the publications of the 30-week trials (Buse et al. 2004; DeFronzo et al. 2005; Kendall et al., 2005). A post hoc interim analysis was performed, with subanalyses by Week 104 weight change quartiles or $HbA_{1c}$ change quartiles. In some analyses, patients were stratified by normal baseline ALT values ≦19 IU/L for females and ≦30 IU/L for males (Prati et al., Ann. Intern. Med. 137:1-9 (2002)). In some analyses, subjects were stratified by baseline age. Results are given as mean±SEM unless otherwise indicated.

Results. Subjects. As noted above, T2dm patients not achieving glycemic control with MET and/or SFU were enrolled in 30-wk, placebo-controlled, phase 3 trials followed by open-label extensions. Demographics and baseline metabolic parameters are given in Table 1. Of the 2-year completers, 39% were being treated with ACE-inhibitors, 37% were being treated with HMG CoA reductase inhibitors (statins), and 39% were being treated with acetylsalicylic acid (aspirin).

TABLE 1

Demographics and baseline characteristics.

| | 2-Year Completers (n = 283) | Intent-to-Treat (n = 521) |
|---|---|---|
| Sex (%): Male/Female | 63/38 | 59/41 |
| Age (y) | 57 ± 10 | 55 ± 10 |
| Race (%): Caucasian/Black/Hispanic/Other | 81/11/7/2 | 74/11/12/3 |
| Duration of Diabetes (y) | 8 ± 6 | 8 ± 6 |
| Baseline $HbA_{1c}$ (%) | 8.3 ± 1.0 | 8.4 ± 1.1 |
| Baseline Body Weight (kg) | 100 ± 19 | 99 ± 20 |
| Baseline BMI (kg/m$^2$) | 34 ± 6 | 34 ± 6 |
| Fasting Plasma Glucose (mg/dL) | 174 ± 45 | 179 ± 49 |

Percentages may add up to less or more than 100 due to rounding. Mean ± SD.

Metabolic Changes. At Week 104 (FIG. 4), subjects completing 2 years of exenatide treatment (n=283) had reduced $HbA_{1c}$ (−1.1±0.1%; 95% CI: −1.3 to −1.0%; p<0.0001), FPG (−25.2±2.8 mg/dL; 95% CI (confidence interval): −31 to −20 mg/dL; p<0.0001), body weight (−4.7±0.3 kg; 95% CI: −5.4 to −4.0 kg; p<0.0001), and BMI (−1.6±0.1 kg/m$^2$; 95% CI: −1.8 to −1.4 kg/m$^2$; p<0.0001) from baseline. The reductions in $HbA_{1c}$ and FPG were evident as early as Week 12 (−1.1±0.1% and −25.1±2.4 mg/dL, respectively), indicating a sustained glycemic effect. Weight change was −1.6±0.1 kg at Week 12 and continued to progressively decrease over the observation period; 81% of subjects lost weight over 2 years of exenatide treatment. Similar outcomes were observed for a more conservative analysis using the ITT population. Changes from baseline to Week 104 in the ITT population were $HbA_{1c}$: −0.8±0.1%, FPG: −16±2 mg/dL, and weight: −3.6±0.2 kg.

In the 2-year completer population overall, 50% of subjects achieved $HbA_{1c}$ of less than or equal to 7% and 31% achieved $HbA_{1c}$ less than or equal to 6.5%. In the 213 subjects with baseline $HbA_{1c}$<9% (mean 7.8%), $HbA_{1c}$ change was −0.9±0.1%. In the 70 subjects with baseline $HbA_{1c}$≧9% (mean 9.7%), $HbA_{1c}$ change was −2.0±0.2%. Conversely, $HbA_{1c}$ reductions were similar across different baseline BMI stratifications: −1.2±0.1% for baseline BMI<30 kg/m$^2$; −1.1±0.1% for baseline BMI≧30 and <40 kg/m$^2$; −1.2±0.2% for baseline BMI≧40 kg/m$^2$.

In a subgroup of the 2-year completer population in whom data were collected for analyses (N=112), HOMA-B (Homeostasis Model Assessment of beta cell function) improved significantly (p<0.01 for baseline vs. Week 104; percentage change in FIG. 4C), accompanied by a modest improvement in HOMA-S (Homeostasis Model Assessment Insulin Sensitivity) (8.3% change in median HOMA-S; p<0.01 for baseline vs. Week 104).

To determine whether there were age-specific differences in the response to exenatide treatment, change in $HbA_{1c}$, FPG, and body weight were examined by baseline age <45 years (n=26), 45-54 years (n=91), 55-64 years (n=97), or greater than or equal to 65 years (n=69). Reductions were not age-dependent: $HbA_{1c}$ change was −1.1±0.2%, −1.0±0.1%, −1.3±0.1%, and −1.2±0.1%, respectively; FPG change was −19.8±7.8 mg/dL, −20.5±5.5 mg/dL, −29.7±5.0 mg/dL, and −27.3±4.7 mg/dL, respectively; weight change was −3.6±1.0 kg, −4.6±0.7 kg, −4.9±0.6 kg, and −4.9±0.6 kg, respectively.

Hepatic Injury Biomarkers. In the 2-year completer population, mean ALT and AST declined progressively (FIGS. 4D&E; p<0.05). Week 104 weight change was mildly correlated with baseline ALT (r=−0.09) or ALT change (r=0.31) for the overall group. The correlation between $HbA_{1c}$ change and ALT change (r=0.19) was also low. Similarly, weight change and ALT change were minimally correlated in the elevated baseline ALT group (r=0.29), with an r=0.25 correlation between $HbA_{1c}$ change and ALT change in the same population. But, when the changes in body weight, ALT, and $HbA_{1c}$ for the entire 2-year completer population were stratified by Week 104 weight change quartiles (FIG. 5A-D), the 25% of subjects who lost the most weight were shown to have also had the greatest reductions in ALT and $HbA_{1c}$. In contrast, stratification by baseline $HbA_{1c}$ was uninformative (FIG. 5E-H).

Figure 6:
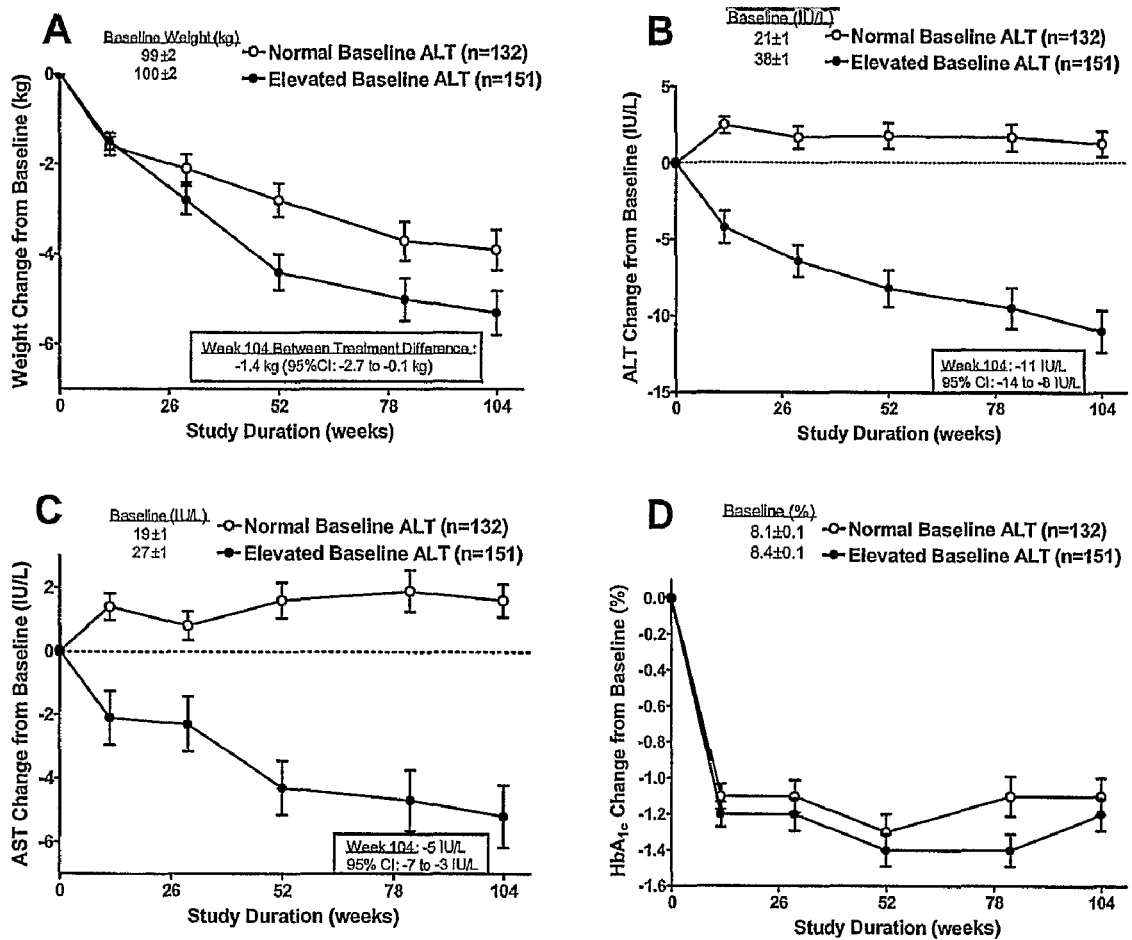
FIG. 6. Body weight, ALT, AST, and $HbA_{1c}$ over 2 years of exenatide treatment stratified by baseline ALT (Female ≦19 IU/L; Male ≦30 IU/L).
Figure 8:
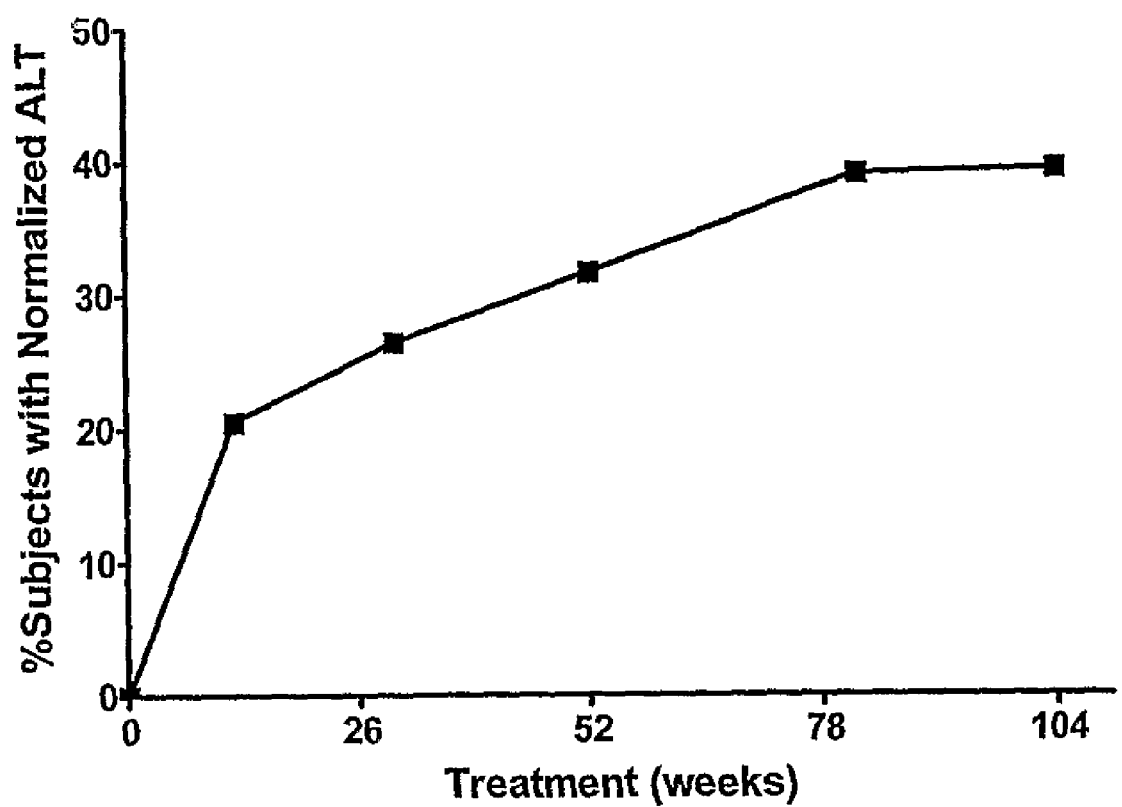
FIG. 8. Normalization of ALT among patients with elevated baseline ALT. Normal ALT range: Female ≦19 IU/L; Male ≦30 IU/L. N=151

When stratified by baseline ALT, a more refined clinical picture emerged. As shown in FIG. 6, exenatide treatment improved ALT (p<0.001 at Week 104) and AST (p<0.001 at Week 104) in subjects with elevated baseline ALT, but had little or no effect on ALT and AST in subjects with normal ALT at baseline. Subjects with elevated ALT at baseline (baseline weight 100±2 kg) lost more weight than subjects with normal ALT at baseline (baseline weight 99±2 kg;

p=0.04 at Week 104). The majority of subjects with normal ALT at baseline lost weight and had sustained $HbA_{1c}$ reduction with long-term exenatide treatment, but had minimal changes in ALT or AST. In contrast, among subjects with elevated ALT at baseline, the 25% who lost the most weight also had the greatest $HbA_{1c}$ reduction coupled with the greatest ALT reduction (FIG. 7 A-D). The remaining 75% of subjects with elevated ALT at baseline had equivalent ALT reductions independent of weight and $HbA_{1c}$ change. In contrast, a similar relationship was not observed for ALT and $HbA_{1c}$ after stratifying the same data by Week 104 $HbA_{1c}$ change (FIG. 7E-H). Overall, 39% of subjects with elevated baseline ALT had normalization of ALT after 2 years of exenatide treatment (FIG. 8).

Clinical Laboratory Findings and Safety. Chronic exenatide therapy was generally well-tolerated, with mild-to-moderate nausea the most common side-effect. The increase in nausea seen during the 10-week interval of Weeks 31 to 40 may be due in part to unblinding, as patient expectation may increase nausea reporting.

These data further demonstrate that IC therapy, e.g., exenatide therapy, for 2 years resulted in sustained improvements in glycemic control, blood pressure (data not shown), and hepatic injury biomarkers, coupled with progressive body weight reductions, in T2DM patients not achieving adequate glycemic control with MET, SFU, or MET/SFU. The sustained nature of these changes may in part reflect exenatide's effects on measures of β-cell secretory function, as evidenced by the improvement in HOMA-B reported here and the favorable changes in the proinsulin-to-insulin ratio previously reported (Buse et al., 2004; Kendall et al., 2005). To address the possibility of self-selection, we determined $HbA_{1c}$ and weight changes for the ITT population. The trends for $HbA_{1c}$ and weight reductions in the ITT population were similar to those observed in the completer cohort, although smaller in magnitude. These data argue against any significant self-selection bias confounding the interpretation of these results.

Exenatide provided sustained and significant reductions in $HbA_{1c}$, with 50% of patients with baseline $HbA_{1c} > 7\%$ achieving an $HbA_{1c}$ less than or equal to 7%. Patients with baseline $HbA_{1c}$ greater than or equal to 9% had $HbA_{1c}$ reductions of 2%. Taken together, these observations are important indicators of the clinical impact of exenatide on glycemic control in T2DM patients. To place these results in context, in the only published head-to-head comparator trial to date (Heine et al., Annals Int. Med. 143:559-569 (2005)), exenatide or insulin glargine treatment each produced $HbA_{1c}$ reductions of ~1.1%. However, in this study designed to test exenatide noninferiority to insulin glargine, exenatide treatment was associated with significantly fewer episodes of nocturnal hypoglycemia and produced ~2.3 kg weight reduction compared with ~1.8 kg weight gain in the insulin glargine treatment arm.

Exenatide was associated with progressive reductions in body weight, with 81% of patients losing weight. These reductions in body weight are especially notable, because no specific diet or exercise counseling or caloric restriction were required by the study protocol. In addition, there was no apparent plateau for exenatide's weight reduction effects, even after 2 years of exenatide exposure. This is in sharp contrast to the weight gain ordinarily seen with most other antidiabetic agents as glycemia improves (Yki-Järvinen et al., Diabetes Care 24:758-767 (2001; Purnell et al., Treat. Endocrinol. 2:33-47 (2003; Makimattila et al., Diabetologia 42:406-412 (1999)). The reductions in body weight with exenatide treatment are consistent with exenatide's known ability to reduce food intake (Szayna et al., Endocrinology 141:1936-1941 (2000); Edwards et al., Am. J. Physiol. Endocrinol. Metab. 281:E155 E161 (2001)). This weight loss can be an important benefit in the diabetic population, as it can improve glycemic control, decrease mortality rate and improve cardiovascular risk profiles (Maggio et al., Endocrinol. Metab. Clin. North Am. 32:805-822 (2003); Bray et al., J. Clin. Endocrinol. Metab. 89:2583-2589 (2004); Williamson et al., Diabetes Care 23:1499-1504 (2000)).

At 82 weeks of IC treatment of Example 1, significant improvements in important cardiovascular risk factors: diastolic blood pressure, HDL-C, and triglycerides, were observed. The greatest improvements in cardiovascular risk factors were observed in patients who had the greatest weight reductions. Patients in weight change quartile 1, who had a mean weight reduction of 11.9 kg, had the largest mean changes in systolic blood pressure (−3.9 mm Hg), diastolic blood pressure (−4.4 mm Hg), HDL-C (+7.3 mg/dL), and triglycerides (−93 mg/dL). Although serum lipid concentrations were not measured after 2 years of exenatide treatment in this Example 2, both diastolic and systolic blood pressure showed sustained reductions. These improvements in multiple cardiovascular risk factors have patient benefits beyond glycemic control.

No medications are currently approved for the treatment of NAFLD (Yki-Järvinen et al., Curr. Molec. Med. 5:287-295 (2005); American Gastroenterological Association, Medical position statement: Nonalcoholic fatty liver disease. Gastroenterology 123:1702-1704 (2002); Angulo et al., Exp. Opinion. 4:611-623 (2003)). Preliminary data have been reported suggesting some reversal of liver damage by metformin, TZDs, gemfibrozil, and other agents (Yki-Järvinen et al., Curr. Molec. Med. 5:287-295 (2005); Angulo et al., Exp. Opinion. 4:611-623 (2003)). However, gradual weight loss remains the recommended therapy. NAFLD is the most common cause of elevated ALT and AST (Yki-Järvinen et al., Curr. Molec. Med. 5:287-295 (2005); Angulo et al., Exp. Opinion. 4:611-623 (2003)). Because NAFLD can only be definitively diagnosed by histological examination of hepatic tissue, we cannot confirm the presence of NAFLD at baseline in our exenatide-treated cohort. However, in patients with type 2 diabetes, NAFLD is the most common cause of ALT elevations and a reduction in ALT is likely to reflect a decrease in liver inflammation. Here we report that improvements in the liver injury biomarkers ALT and AST were associated with 2 years of exenatide therapy. Further, the 25% of patients who lost the most weight had the largest reductions in ALT and AST, with 39% of patients who had elevated ALT at baseline achieving a normal ALT value with exenatide treatment. In contrast, stratification by 2-year $HbA_{1c}$ change did not demonstrate a similar relationship between ALT and $HbA_{1c}$. These initial correlation and quartile analyses for change in body weight and $HbA_{1c}$ seem to indicate that weight changes are a more predominant driving factor in the reduction of ALT than changes in glycemia. While not to be bound by theory, exenatide may improve NAFLD through mechanisms that are partially weight-dependent and partially weight-independent. Exenatide may potentially act on the liver via effects on the pancreatic β-cell cell (ambient glycemia) and hepatic lipid metabolism.

Two year data indicate that exenatide elicits sustained improvements in glycemic control, β-cell function, blood pressure, and hepatic injury biomarkers, coupled with progressive weight reduction.

Thus glucoregulatory therapy, e.g. IC exenatide therapy, provides treatment of metabolic liver disease such as non alcoholic fatty liver disease (NAFLD) or non alcoholic steatosis hepatitis (NASH). The therapy is evident by the observed improvement in biochemical markers of liver function, specifically ALT and AST.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

The invention claimed is:

1. A method for treating nonalcoholic steatohepatitis in a human in need thereof comprising subcutaneously administering to the human a therapeutically effective amount of exendin-4 to treat the nonalcoholic steatohepatitis in the human.

2. The method of claim 1, further comprising administering a therapeutically effective amount of a dipeptidyl peptidase-IV inhibitor, metformin, a sulfonylurea, or a combination of two or more thereof.

3. A method for treating nonalcoholic steatohepatitis in a subject in need thereof comprising administering to the subject a therapeutically effective amount of exendin-4 to treat the nonalcoholic steatohepatitis in the subject.

4. The method of claim 3, wherein the therapeutically effective amount is an amount that maintains an average plasma concentration of exendin-4 of at least 10 pg/ml for at least 12 hours.

5. The method of claim 3, wherein the exendin-4 is parenterally administered to the subject.

6. The method of claim 3, wherein the subject is a human.

7. The method of claim 3, wherein the exendin-4 is administered to the subject by subcutaneous injection.

8. The method of claim 3, further comprising administering a therapeutically effective amount of a dipeptidyl peptidase-IV inhibitor, metformin, a sulfonylurea, or a combination of two or more thereof.

9. A method for treating nonalcoholic fatty liver disease in a subject in need thereof comprising administering to the subject a therapeutically effective amount of exendin-4 to treat the nonalcoholic fatty liver disease in the subject.

10. The method of claim 9, wherein the therapeutically effective amount is an amount that maintains an average plasma concentration of exendin-4 of at least 10 pg/ml for at least 12 hours.

11. The method of claim 9, wherein the exendin-4 is parenterally administered to the subject.

12. The method of claim 9, wherein the subject is a human.

13. The method of claim 9, wherein the exendin-4 is administered to the subject by subcutaneous injection.

14. The method of claim 9, further comprising administering a therapeutically effective amount of a dipeptidyl peptidase-IV inhibitor, metformin, a sulfonylurea, or a combination of two or more thereof.

15. A method for treating nonalcoholic fatty liver disease in a human in need thereof comprising subcutaneously administering to the human a therapeutically effective amount of exendin-4 to treat the nonalcoholic fatty liver disease in the human.

16. The method of claim 15, further comprising administering a therapeutically effective amount of a dipeptidyl peptidase-IV inhibitor, metformin, a sulfonylurea, or a combination of two or more thereof.

* * * * *

UNITED STATES PATENT AND TRADEMARK OFFICE
CERTIFICATE OF CORRECTION

PATENT NO. : 8,389,472 B2  Page 1 of 1
APPLICATION NO. : 12/063712
DATED : March 5, 2013
INVENTOR(S) : Baron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1336 days.

Signed and Sealed this
First Day of September, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,389,472 B2 | Page 1 of 1 |
| APPLICATION NO. | : 12/063712 | |
| DATED | : March 5, 2013 | |
| INVENTOR(S) | : Baron et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 965 days.

Signed and Sealed this
Twenty-eighth Day of June, 2016

Michelle K. Lee
*Director of the United States Patent and Trademark Office*